(12) United States Patent
Casares Lagar et al.

(10) Patent No.: US 11,560,407 B2
(45) Date of Patent: Jan. 24, 2023

(54) FOXP3-BINDING PEPTIDES AND USES THEREOF

(71) Applicant: FUNDACIÓN PARA LA INVESTIGACIÓN MÉDICA APLICADA, Pamplona (ES)

(72) Inventors: Inés Noelia Casares Lagar, Pamplona (ES); Juan José Lasarte Sagastibelza, Pamplona (ES); Teresa Lozano Moreda, Pamplona (ES); Julen Oyarzabal Santamarina, Pamplona (ES); Maria Obdulia Rabal Gracia, Pamplona (ES)

(73) Assignee: FUNDACIÓN PARA LA INVESTIGACIÓN MÉDICA APLICADA, Pamplona (ES)

(*) Notice: Subject to any disclaimer, the term of this patent is extended or adjusted under 35 U.S.C. 154(b) by 164 days.

(21) Appl. No.: 16/853,397

(22) Filed: Apr. 20, 2020

(65) Prior Publication Data
US 2020/0317733 A1 Oct. 8, 2020

Related U.S. Application Data

(62) Division of application No. 16/343,394, filed as application No. PCT/EP2017/076690 on Oct. 19, 2017, now Pat. No. 10,654,896.

(30) Foreign Application Priority Data

Oct. 26, 2016 (EP) ..................... 16195686

(51) Int. Cl.
*C12N 15/11* (2006.01)
*C07K 7/08* (2006.01)
(Continued)

(52) U.S. Cl.
CPC .............. *C07K 7/08* (2013.01); *A61K 38/12* (2013.01); *A61P 35/00* (2018.01); *C07K 7/50* (2013.01);
(Continued)

(58) Field of Classification Search
None
See application file for complete search history.

(56) References Cited

FOREIGN PATENT DOCUMENTS

| EP | 2223998 A1 | 9/2010 |
|---|---|---|
| WO | WO 2009/065982 A1 | 5/2009 |
| WO | WO 2015/124715 A1 | 8/2015 |

OTHER PUBLICATIONS

Alberts, B. et al; Molecular Biology of the Cell (2002) ISBN 0-8153-3218-1.*

Cao, Wei et al; "Prediction of n-myristoylation modification of proteins bysvm." Bioinformation (2011) 6(5) p204-206.*
Scott, Charles P. et al; "Structural requirements forteh biosynthesis of bacbone cyclic peptide libraries." Chem. Biol. (2001) 6 p801-815.*
International Search Report and Written Opinion dated Jan. 10, 2018 for PCT/EP2017/076690, 17 pages.
Adessi, et al. "Converting a peptide into a drug: Strategies to improve stability and bioavailability", Current Medicinal Chemistry, May 1, 2001, vol. 9, No. 9, pp. 963-978, XP009061547, ISSN: 8929-8673, DOI: 10.2174/0929867024606731, figure 1.
(Continued)

*Primary Examiner* — Fred H Reynolds
(74) *Attorney, Agent, or Firm* — Squire Patton Boggs (US) LLP

(57) ABSTRACT

The present invention provides peptides of general formula (I) and salts thereof, wherein: $R_1$ and $R_2$, taken together, form a birradical linker; and $R_2'$ is hydrogen; or, alternatively, $R_1$ is selected from hydrogen, —C(=O)—CH$_2$—NH—C(=O)—(C$_1$-C$_5$)alkyl, and —C(=O)—(C$_1$-C$_{20}$)alkyl; one of $R_2$ and $R_2'$ is hydrogen and the other is selected from —C(=O)NR$_3$R$_4$, and —C(=O)OH; and $R_3$ and $R_4$ are same or different and are selected from hydrogen and (C$_1$-C$_{10}$)alkyl.
These peptides are highly efficient in binding and inhibiting FoxP3, being efficient in inhibiting and blocking Treg cell functionality, which make them useful in the treatment of cancer.
The present invention also provides constructs comprising the peptide of formula (I) as well as combinations comprising the peptide of formula (I), the construct or both.

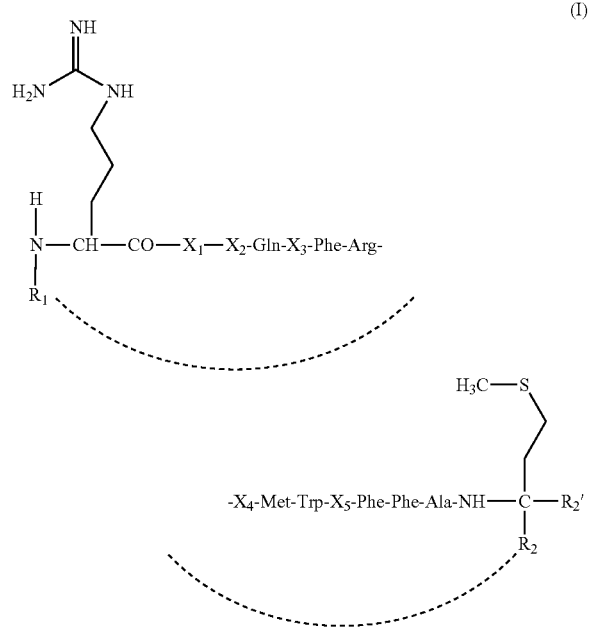

(I)

10 Claims, 5 Drawing Sheets
Specification includes a Sequence Listing.

(51) Int. Cl.
*A61P 35/00* (2006.01)
*C07K 7/50* (2006.01)
*C07K 7/64* (2006.01)
*C07K 14/47* (2006.01)
*A61K 38/12* (2006.01)
*A61K 38/00* (2006.01)

(52) U.S. Cl.
CPC ............ *C07K 7/64* (2013.01); *C07K 14/4702* (2013.01); *C07K 14/4713* (2013.01); *C12N 15/11* (2013.01); *A61K 38/00* (2013.01); *C07K 2319/10* (2013.01)

(56) References Cited

OTHER PUBLICATIONS

Altschul, et al., "Basic local alignment search tool", J. Mol. Biol. 1990, vol. 215, pp. 403-410.
Casares, et al., "A peptideinhibitor of FOXP3 impairs regulatory T cell activity and improves vaccine efficacy in mice", The Journal of Immunology 2010, vol. 185, No. 9, pp. 5150-5159.
Copolovici, et al., "Cell-penetrating peptides: design, synthesis, and applications", ACS Nano 2014, vol. 8, No. 3, pp. 1972-1994.
Ford, et al., "Protein transduction: an alternative to genetic intervention?", Gene Therapy 2001, vol. 8, pp. 1-4.
Frassanito, et al., "Myeloma cells act as tolergenic antigen-presenting cells and induce regulatory T cells in vitro", European Journal of Haematology 2015, vol. 95, pp. 65-74.
Higgins, et al., "Clustal V: improved software for multiple sequence alignment", CABIOS 1992, vol. 8, No. 2., pp. 189-191.
Huibregtse, et al., "Induction of Ovalbumin-specific tolerance by oral administration of *Lactococcus lactis* SECRETING Ovalbumin", Gastroenterology 2007, vol. 133, pp. 517-528.
Joosten, et al., "Human CD4 and CD8 regulatory T cells in infectious diseases and vaccination", Human Immunology 2008, vol. 69, pp. 760-770.
Khalil, et al., "The new era of cancer immunotherapy: manipulating T-cell activity to overcome malignancy", Advances in Cancer Research 2015, vol. 127, pp. 759-767.
Lozano, et al., "Searching for Achilles heel of FOXP3", Frontiers in Oncology, Dec. 3, 2013, vol. 3, Article 294, pp. 1-9.
Lozano, et al., "Targeting inhibition of Foxp3 by a CD28 2'-Fluro oligonucleotide aptamer conjugated to P60-peptide enhances active cancer", Biomaterials Mar. 8, 2016, vol. 91, pp. 73-80.
Ono, et al., "FOXP3 controls regulatory T-cell function by interacting with AML1/Runx1", Nature Apr. 5, 2007, vol. 446, pp. 685-689.
Sambrook, et al., "Molecular Cloning, a laboratory manual", 4$^{th}$ ed. Cold Spring Harbor Laboratory Press NY, 2012, vol. 1-3, Chapter 3 from vol. 1: "Cloning and Transformation with Plasmid Vectors".
Schmidt, et al., "Liposome-based adjuvants for subunit vaccines: formulation strategies for subunit antigens and immunostimulators", Pharmaceutics Mar. 2016, vol. 10, vol. 8, No. 1, pp. 1-22.
Song, et al., "Structural and biological features of FOXP3 dimerization relevant to regulatory T cell function", Cell Reports Jun. 2012, vol. 1, No. 6, pp. 665-675.
Szylberg, et al., "The role of foxp3 in human cancers", Anticancer Research 2016, vol. 36, pp. 3789-3794.
Williams, et al., "Maintenance of the Foxp3-dependent developmental program in mature regulatory T cells requires continued expression of Foxp3", Nature Immunology 2007, vol. 8, pp. 277-284.

* cited by examiner

Scheme III

FOXP3-BINDING PEPTIDES AND USES THEREOF

This application is a divisional of U.S. patent application Ser. No. 16/343,394, filed on Apr. 18, 2019, which claims the benefit of European Patent Application EP 16195686.7 filed Oct. 26, 2016.

The present invention refers to peptides capable of binding FoxP3 and to pharmaceutical salts thereof. These peptides are able to regulate/block Treg cells, which find application in the treatment of diseases wherein a regulation of Treg cell activity is needed, such as infectious or neoplastic diseases.

BACKGROUND ART

Immunotherapy is very promising for the treatment of patients with cancer. The numerous clinical protocols carried out which have used therapies based on cytokines, infusions of effector T cells or vaccination protocols have demonstrated that cancer immunotherapy is generally safe. However, although the induction of immune response after the treatment has been observed in these clinical protocols, most of the patients are incapable of developing an effective antitumor response. The demonstration of the presence of Treg lymphocytes in the tumor tissue or the lymph nodes of patients with melanoma, lung cancer, ovarian cancer, pancreatic cancer and breast cancer as well as in hepatocarcinomas (Nishikawa H. et al., "Regulatory T cells in tumor immunity", Int. J. Cancer, 2010, vol. 127, pages 759-767) and the description that tumor tissue secretes chemokines which specifically attract this subpopulation towards tumor tissue, indicate that the access of Treg lymphocytes to the tumor is a dynamic process and that it exerts an immunosuppressive effect facilitating the progression of the disease.

The regulatory T cells (Treg cells or Tregs), formerly known as suppressor T cells, are a subpopulation of T cells which modulate the immune system, maintain tolerance to self-antigens, and prevent autoimmune disease. Treg cells are immunosuppressive and generally suppress or down-regulate induction and proliferation of effector T cells. Treg cells express the biomarkers CD4, FOXP3, and CD25 and are thought to be derived from the same lineage as naïve CD4 cells.

The presence of Treg in the tumor as well as in peripheral nodes could explain the low efficacy of the immunotherapy protocols. In the same way, in infectious diseases, the control exerted by Treg lymphocytes can limit the magnitude of the effector T responses and cause the failure in the control of the infection. It has thus been described that some viruses such as hepatitis B virus, hepatitis C virus and HIV (Joosten S. A. et al., "Human CD4 and CD8 regulatory T cells in infectious diseases and vaccination", Hum. Immunol., 2008, vol. 69(11), pages 760-70) can use Treg lymphocytes to block the antiviral immune response and thus allow the establishment of the persistent chronic infection. Due to all this, it is believed that the modulation of the action of Treg lymphocytes can be essential in the development of immunotherapies against cancer or against infectious diseases.

In this regard, methods for inhibiting the activity of Treg lymphocytes have been disclosed in the prior art, in an attempt to regulate their negative effect on the immune system. Some of these methods involve the elimination of Treg cells, by means of using depleting antibodies or by means of blocking the cytokines that they produce and which may be responsible for their activities (TGF-β, IL-10). The methods which are based on the depletion of the regulatory T cells have the drawback that they eliminate the cells and involve risks of causing autoimmune diseases.

In an attempt to find alternative immunotherapies, FOXP3 (forkhead box P3), also known as scurfin, attracted the interest of the scientists. This protein is member of the FOX protein family, and appears to function as a master regulator of the regulatory pathway in the development and function of regulatory T cells. Moreover, in addition to naturally occurring Treg which are generated in the thymus, FoxP3 expression can be induced in the periphery in CD4+ CD25− T cells through TCR crosslinking, leading to attenuation of effector functions in the stimulated cells (proliferation and cytokine production) (Reviewed in Lozano T. et al., "Searching for the Achilles Heel of FOXP3", Front. Oncol., 2013, vol. 3, page 294). The immune-suppressive tumour microenvironment, affects antigen presentation to tumor-specific T cells and may result in suboptimal T-cell activation and T-cell tolerance. In this regard, expression of FoxP3 after suboptimal TCR stimulation of CD4+ in the presence of immunosuppressive cytokines TGF-β, IL-6 or IL-10 and other metabolites may have an important role governing the functionality of transferred lymphocytes favouring T-cell-tolerization. It has become evident that Foxp3 can be transiently expressed in activated human or murine CD4+ T cells acquiring some features of Treg cells (Reviewed in Lozano T. et al., 2013, supra). But, such induced FoxP3 expression may not be restricted to CD4 T cells. Indeed there are increasing reports on the existence/induction of CD8+ FoxP3+ T cells in cancer and chronic infections (Frassanito M. A. et al. "Myeloma cells act as tolerogenic antigen-presenting cells and induce regulatory T cells in vitro", Eur J Haematol., 2015, vol. 95(1), pages 65-74). These findings suggest that FoxP3 may serve to shut off T cell activation, acting as a broad regulator of immune response, and thus, FoxP3 can be considered as a potential therapeutic target.

The molecular basis of FOXP3 function has been poorly understood. It has been described that the transcription factor scurfin (FOXP3, expression product of the foxp3 gene) (Williams L. M. and Rudensky A. Y., "Maintenance of the Foxp3-dependent developmental program in mature regulatory T cells requires continued expression of Foxp3", Nat. Immunol., 2007, vol. 8, pages 277-84) is essential for the activity of Treg lymphocytes, such that its presence determines the suppressive activity of these cells. The cDNA sequences encoding murine and human scurfin have been the object of U.S. Pat. No. 6,414,129 which furthermore describes that the modulation of the expression of scurfin can have therapeutic effects in various diseases; said patent also mentions the use of synthetic peptides, among other molecules, to regulate the expression of the foxp3 gene but does not mention anything about the possibility of inhibiting the activity of the already expressed scurfin.

FOXP3 capacity to bind DNA is critical for its functionality and it is known that FOXP3-DNA interactions are assisted by other cofactors and by multimerization. Growing numbers of transcription factors that interact with FOXP3 are being identified and some have been implicated in the Treg cell-specific gene expression program (Reviewed in Lozano T. et al., 2013, supra). FOXP3 has various distinguishable functional domains: (i) a N-terminal domain (from aa 1 to 193, with two proline-rich regions), (ii) a zinc finger (aa 200-223) and a leucine zipper-like motif (aa 240-261) (ZL domain) located in the centre of the protein and (iii) the highly conserved carboxy terminal forkhead domain (FKH; from aa 338 to 421) responsible for binding to DNA. It has been described that the intermediate region is implicated in FOXP3 dimerization, which is required for its function as a transcriptional regulator (Reviewed in Lozano T. et al., 2013, supra). Also, the physical interaction of this region with the transcription factor AML1 (acute myeloid leukaemia 1)/Runx1 (Runt-related transcription factor 1), suppresses IL-2 and IFN-γ production, upregulates Treg-associated molecules, controls anergy of the cell and exerts Treg suppressive activity (Reviewed in Lozano T. et al., 2013, supra) Thus, those strategies able to inhibit FOXP3 dimerization, its interaction with AML1 or to modify the FOXP3 interactome might have important consequences on Treg activity and thus could be exploited as therapeutic agents in cancer.

In a previous work, it was identified the 15-mer synthetic peptide of sequence SEQ ID NO: 1 (hereinafter also referred "p60")

```
                                            (SEQ ID NO: 1)
ArgAspPheGlnSerPheArgLysMetTrpProPhePheAlaMet
``` which entered the cells, bound to FOXP3 and inhibited murine and human-derived Treg, improving effector T-cell stimulation in vitro and in vivo (Casares N. et al., "A peptide inhibitor of FOXP3 impairs regulatory T cell activity and improves vaccine efficacy in mice", J. Immunol., 2010, vol. 185(9), pages 5150-5159).

In spite of the efforts made in the field of immunotherapy, there is still the need of providing compounds with an improved efficiency in regulating or blocking Treg cells.

SUMMARY OF THE INVENTION

The present inventors have found that by chemically modifying one or both of the free amino and carboxy groups of p60 sequence peptide (SEQ ID NO: 1):

```
                                            (SEQ ID NO: 1)
ArgAspPheGlnSerPheArgLysMetTrpProPhePheAlaMet
``` a surprisingly improvement in the binding to FoxP3 is achieved.

As it is shown below, when the free amino and carboxy groups of the peptide of sequence SEQ ID NO: 1 were modified to form a staple, in particular a head-to-tail staple, there was an increase in the binding to FoxP3 of about 500% with respect to the unmodified p60, and when the free amino and carboxy groups of the peptide of sequence SEQ ID NO: 1 were derivatized by acetylation and amidation, respectively, an increase in the binding to FoxP3 of about 200% was achieved with respect to unmodified p60.

The present inventors have also identified amino acid positions in p60 peptide sequence that are critical for regulating and substantially improving both the binding to FoxP3 and the regulation/blocking of the immunosuppressive activity of Treg lymphocytes.

As it is shown below, when one or more of the amino acids found in p60 at positions 2, 3, 5, 8, and 11 (the numbering starting from N(t) residue of SEQ ID NO: 1) were replaced by another, there was a remarkable increase in the binding to FOXP3, which reached up to a 460%.

The present inventors have also found that the peptides of the invention provide an increase in FoxP3 inhibition of up to about a 50%, when compared to p60.

Although there is no intention to be bound by any theory, it is believed that the peptides of the invention, due to their small size, can be introduced in the cells to block the action of FoxP3.

The remarkable improvement shown by the peptides of the invention, both in binding and inhibiting FoxP3, was indicative that they could inhibit Treg activity. This was further experimentally confirmed by the inventors: as shown below the peptides of the invention tested in inhibition Treg assays, inhibited Treg activity, this inhibition being up to 3-fold higher than the inhibition achieved with p60. Therefore, it can be confirmed that the peptides of the invention efficiently block the immunosuppressive activity of Treg lymphocytes, either transiently or temporarily, and substantially improve p60 effect on Treg cells.

In view to the above, it is clear that the improvement provided by the peptides of the present invention is so remarkable that, from the point of view of administration, a substantial lower amount of these peptides can be needed to get the desired therapeutic effect when compared to p60.

In view of the above, the peptides reported by the present inventors mean a great advance in the field of immunotherapy in general, and of cancer or infectious diseases therapies, in particular.

Thus, in a first aspect the present invention provides a peptide, capable of binding FoxP3 and of inhibiting FoxP3, or a pharmaceutically salt thereof, the peptide being selected from the group consisting of:

(a) a peptide of formula (I):

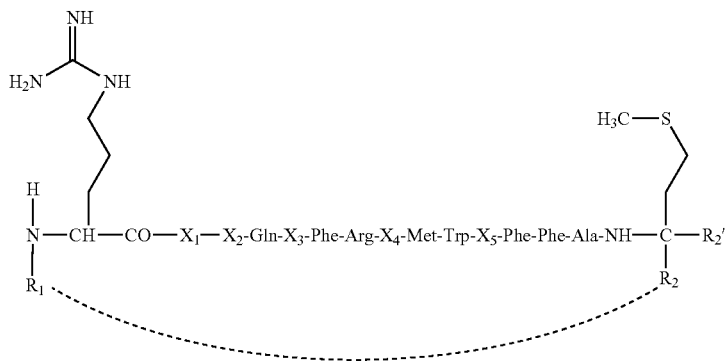

wherein:
$R_1$ and $R_2$, taken together, form a birradical linker; and $R_2'$ is hydrogen;
the linker birradical formed by $R_1$ and $R_2$ being bound to the amino terminal group of the amino acid residue at position 1 and the alpha carbon of the amino acid residue at position 15, and being selected from the group consisting of: C(=O), $(C_1$-$C_{10})$alkyl-$NR_5$—C(=O), $(C_2$-$C_{10})$alkenyl-$NR_6$—C(=O), $(C_2$-$C_{10})$alkynyl-$NR_7$—C(=O), $(C_1$-$C_{10})$alkyl-$NR_8$—C(=O)—$(C_1$-$C_{10})$alkyl-$NR_9$C(=O), $(C_1$-$C_{10})$alkyl-C(=O)—$(C_1$-$C_{10})$alkyl-$NR_{10}$—C(=O), $(C_1$-$C_{10})$alkyl-O—$(C_1$-$C_{10})$alkyl-$NR_{11}$-C(=O), $(C_1$-$C_{10})$alkyl-C(=O)—$NR_{12}$—$(C_1$-$C_{10})$alkyl-$NR_{13}$C(=O), $(C_1$-$C_{10})$alkyl-$NR_{14}R_{15}$—$(C_1$-$C_{10})$alkyl-$NR_{16}$—C(=O), $(C_1$-$C_{10})$alkyl-C(=O)—O—$(C_1$-$C_{10})$alkyl-$NR_{17}$—C(=O), $(C_1$-$C_{10})$alkyl-O—C(=O)—$(C_1$-$C_{10})$alkyl-$NR_{18}$—C(=O), $(C_1$-$C_{10})$alkyl-C(=O), $(C_2$-$C_{10})$alkenyl-C(=O), $(C_2$-$C_{10})$alkynyl-C(=O), $(C_1$-$C_{10})$alkyl-O—$(C_1$-$C_{10})$alkyl-C(=O), $(C_1$-$C_{10})$alkyl-C(=O)—$(C_1$-$C_{10})$alkyl-C(=O), $(C_1$-$C_{10})$alkyl-O—C(=O)—$(C_1$-$C_{10})$alkyl-C(=O), $(C_1$-$C_{10})$alkyl-C(=O)—O—$(C_1$-$C_{10})$alkyl-C(=O), $(C_1$-$C_{10})$alkyl-$NR_{19}R_{20}$—$(C_1$-$C_{10})$alkyl-C(=O), $(C_1$-$C_{10})$alkyl-$NR_{21}$—C(=O)—$(C_1$-$C_{10})$alkyl-C(=O), $(C_1$-$C_{10})$alkyl-C(=O)—$NR_{22}$—$(C_1$-$C_{10})$alkyl-C(=O), and or, alternatively, $R_1$ is a monoradical selected from the group consisting of hydrogen, —C(=O)—$CH_2$—NH—C(=O)—$(C_1$-$C_5)$alkyl, and —C(=O)—$(C_1$-$C_{20})$alkyl;

one of $R_2$ and $R_2'$ is a hydrogen radical and the other is a monoradical selected from the group consisting of —C(=O)$NR_3R_4$, and —C(=O)OH;

$R_3$ and $R_4$ are monoradicals the same or different and are selected from the group consisting of: hydrogen and $(C_1$-$C_{10})$alkyl; and $R_5$ to $R_{22}$ are monoradicals selected from the group consisting of: hydrogen, $(C_1$-$C_{10})$alkyl, $(C_2$-$C_{10})$alkenyl, and $(C_2$-$C_{10})$alkynyl;

the $(C_1$-$C_{10})$alkyl, $(C_2$-$C_{10})$alkenyl, and $(C_2$-$C_{10})$alkynyl being non-substituted or substituted, wherein "substituted $(C_1$-$C_{10})$alkyl" means that the $(C_1$-$C_{10})$alkyl is substituted by one or more radicals selected from the group consisting of: halogen, —$OR_{23}$, —$NO_2$, —$NR_{24}R_{25}$, —$SR_{26}$, —$SO_2R_{27}$, —$CO_2R_{28}$, $(C_1$-$C_{10})$alkyl, $(C_1$-$C_{10})$alkyl-O—, and a $(C_3$-$C_6)$cycloakyl, being $R_{23}$ to $R_{28}$ monoradicals, the same or different, and selected from the group consisting of: —H, $(C_1$-$C_{10})$alkyl, $(C_2$-$C_{10})$alkenyl, and $(C_2$-$C_{10})$alkynyl;

"substituted $(C_2$-$C_{10})$alkenyl" means that the $(C_2$-$C_{10})$alkenyl is substituted by one or more radicals selected from the group consisting of: halogen, —$OR_{29}$, —$NO_2$, —$NR_{30}R_{31}$, —$SR_{32}$, —$SO_2R_{33}$, —$CO_2R_{34}$, $(C_1$-$C_{10})$alkyl, $(C_1$-$C_{10})$alkyl-O—, and a $(C_3$-$C_6)$cycloakyl, being $R_{29}$ to $R_{34}$ monoradicals, the same or different, and selected from the group consisting of: —H, $(C_1$-$C_{10})$alkyl, $(C_2$-$C_{10})$alkenyl, and $(C_2$-$C_{10})$alkynyl;

"substituted $(C_2$-$C_{10})$alkynyl" means that the $(C_2$-$C_{10})$alkynyl is substituted by one or more radicals selected from the group consisting of: halogen, —$OR_{35}$, —$NO_2$, —$NR_{36}R_{37}$, —$SR_{38}$, —$SO_2R_{39}$, —$CO_2R_{40}$, $(C_1$-$C_{10})$alkyl, $(C_1$-$C_{10})$alkyl-O—, and a $(C_3$-$C_6)$cycloakyl, being $R_{35}$ to $R_{40}$ monoradicals, the same or different, and selected from the group consisting of: —H, $(C_1$-$C_{10})$alkyl, $(C_2$-$C_{10})$alkenyl, and $(C_2$-$C_{10})$alkynyl;

provided that:

(i) when $R_1$ and $R_2$ form a birradical linker as defined above or, alternatively, when $R_1$ is —C(=O)—$(C_1$-$C_{20})$alkyl or —C(=O)—$CH_2$—NH—C(=O)—$(C_1$-$C_5)$alkyl; or, alternatively, when $R_2'$ is —C(=O)$NR_3R_4$; or, alternatively, when $R_1$ is —C(=O)—$(C_1$-$C_{20})$alkyl or —C(=O)—$CH_2$—NH—C(=O)—$(C_1$-$C_5)$alkyl, and $R_2'$ is —C(=O)$NR_3R_4$; then $X_1$ to $X_5$ represent amino acid residues, the same or different; and (ii) when $R_1$ is hydrogen, one of $R_2$ and $R_2'$ is hydrogen and the other —C(=O)H, then $X_1$ to $X_5$ represent amino acid residues, the same or different, wherein at least one of $X_1$ to $X_5$ is selected from the group consisting of:

$X_1$ is an amino acid other than L-Asp;
$X_2$ is an amino acid other than L-Phe;
$X_3$ is an amino acid other than L-Ser;
$X_4$ is an amino acid other than L-Lys; and
$X_5$ is an amino acid other than L-Pro;

(b) a peptide having at least 80% of sequence identity with peptide of formula (I) which maintains the ability to bind FoxP3 and inhibit FoxP3 activity in vitro and/or in vivo; and (c) a fragment of the peptide defined in (a) or in (b), wherein said fragment comprises a portion of at least 11 consecutive amino acids of the peptide defined in (a) or in (b), and maintains the ability to bind FoxP3 and inhibit FoxP3 activity in vitro and/or in vivo, wherein when said fragment has a —$NH_2$ radical as N-terminal end, and a —COOH radical as C-terminal end, then it comprises at least one of the amino acid residues $X_1$ to $X_5$ identified in the peptide of formula (I), said at least one residue being selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; and $X_5$ is an amino acid other than L-Pro.

In a second aspect, the present invention provides a construct comprising: (i) a peptide as defined in the first aspect of the invention; and (ii) a cell-penetrating agent with capacity to internalize a peptide in a cell In a third aspect, the present invention provides a combination comprising:

(a) a peptide as defined in the first aspect of the invention, or alternatively, a construct as defined in the second aspect of the invention, or alternatively both the peptide as defined in the first aspect of the invention and a construct as defined in the second aspect of the invention; and (b) one or more immunomodulatory compounds.

In a fourth aspect, the present invention provides a veterinary or pharmaceutical composition comprising a therapeutically effective amount of a peptide as defined in the first aspect of the invention, or of a construct as defined in the second aspect of the invention, or of a combination as defined in the third aspect of the invention, together with at least one veterinary or pharmaceutically acceptable excipient.

As it has been stated above, the present inventors provide data supporting the inhibitory effect of the peptides of the invention on Treg cells.

Due to the role of Treg lymphocytes in a number of biological processes and to the fact that FoxP3 is essential for their immunosuppressive activity, the use of the peptides of the invention opens up a window for a potential development of a new family of drugs that are potentially useful in the treatment of neoplastic diseases and of infectious diseases.

As mentioned above, the inhibition of the biological activity of FoxP3 allows the peptides of the invention to transiently or temporarily regulate or block the immunosuppressive activity of Treg lymphocytes. Therefore therapies can be developed for the treatment of neoplastic diseases or of infectious diseases in which the action of said Treg lymphocytes is furthermore selectively and transiently controlled such that the risk of induction of autoimmunity as a result of their elimination is reduced.

Therefore, the peptides of the invention, as well as the constructs, combinations and compositions of the invention, can be used in the treatment of a pathology in which it is suitable or necessary to transiently or temporarily regulate or block the immunosuppressive activity of Treg lymphocytes, as occurs in the case of neoplastic diseases or of infectious diseases in which the Treg lymphocytes can have an immunosuppressive role, preventing the correct activation of an effective immune response.

Thus, in a fifth aspect the present invention provides the peptide as defined in the first aspect of the invention, or the construct as defined in the second aspect of the invention, or the combination as defined in the third aspect of the invention, or the veterinary or pharmaceutical composition as defined in the fourth aspect of the invention for use as a medicament.

As it is shown below, the peptides of the invention efficiently prevent the growth of tumor cells (see FIGS. 1 to 3).

Therefore, in a sixth aspect, the present invention provides a peptide as defined in the first aspect of the invention, or alternatively a construct as defined in the second aspect of the invention, or alternatively a combination as defined in the third aspect of the invention, or alternatively a pharmaceutical or veterinary composition as defined in the fourth aspect of the invention, for use in the treatment or prevention of a neoplastic disease. Alternatively, this aspect can be also formulated as the use of a peptide as defined in the first aspect of the invention, or alternatively of a construct as defined in the second aspect of the invention, or alternatively of a combination as defined in the third aspect of the invention, or alternatively of a pharmaceutical or veterinary composition as defined in the fourth aspect of the invention for the manufacture of a medicament for the treatment or prevention of a neoplastic disease. Alternatively, the sixth aspect of the invention can also be formulated as a method for the treatment or prevention of a neoplastic disease, the method comprising the step of administering a therapeutically effective amount of a peptide as defined in the first aspect of the invention or, alternatively, of a construct as defined in the second aspect of the invention or of, alternatively, a combination as defined in the third aspect of the invention or, alternatively, of a pharmaceutical or veterinary composition as defined in the fourth aspect of the invention, in a subject in need thereof.

In a seventh aspect the present invention provides a peptide as defined in the first aspect of the invention or a construct as defined in the second aspect of the invention for use in the treatment or prevention of cancer, wherein the treatment or prevention further comprises the administration of one or more immunomodulatory compounds.

In an eighth aspect the present invention provides a nucleic acid encoding a peptide as defined in the first aspect of the invention or a construct as defined in the second aspect of the invention when the cell-penetrating agent is a cell-penetrating peptide; in an ninth aspect the present invention provides a vector comprising the nucleic acid of the eighth aspect of the invention; in a tenth aspect the present invention provides an in vitro process for producing a peptide as defined in the first aspect of the invention or a construct as defined in the second aspect of the invention when the cell-penetrating agent is a cell-penetrating peptide, comprising growing a host cell comprising a nucleic acid as defined in the eighth aspect of the invention under conditions allowing the production of the peptide or construct and, if desired, recovering said peptide or said construct; and, in an eleventh aspect, the present invention provides the use of a nucleic acid of the eighth aspect of the invention in the in vitro preparation of vectors and cells for the treatment of a neoplastic disease.

It is also part of the invention, in a twelfth aspect, a peptide of formula (I) as defined in the first aspect of the invention, wherein $X_1$ represents a D-amino acid or, alternatively, $X_1$ is a non-conservative amino acid with respect to L-Asp, the non-conservative amino acid being selected from non-polar, neutral polar and basic polar amino acid residues.

It is also part of the invention, in a thirteenth aspect, a peptide of formula (I) as defined in the first aspect of the invention, wherein $X_2$ represents a D-amino acid or, alternatively, $X_2$ represents a non-conservative amino acid with respect to L-Phe, the non-conservative amino acid being selected from a neutral polar amino acid, an acidic polar amino acid and a basic polar amino acid.

It is also part of the invention, in a fourteenth aspect, a peptide of formula (I) as defined in the first aspect of the invention, wherein $X_3$ represents a D-amino acid or, alternatively, $X_3$ represents a non-conservative amino acid with respect to L-Ser, the non-conservative amino acid being selected from non-polar, acidic polar and basic polar amino acid residues.

It is also part of the invention, in a fifteenth aspect, a peptide of formula (I) as defined in the first aspect of the invention, wherein $X_4$ represents a D-amino acid or, alternatively, $X_4$ represents a L-basic polar amino acid.

It is also part of the invention, in a sixteenth aspect, a peptide of formula (I) as defined in the first aspect of the invention, wherein $X_5$ represents a D-amino acid or, alternatively, $X_5$ represents a non-conservative amino acid with respect to L-Pro, the non-conservative amino acid being selected from a neutral polar amino acid and a basic polar amino acid.

It is also part of the invention, in a seventeenth aspect, a peptide of formula (I) as defined in the first aspect of the invention, wherein $X_1$ and $X_3$ are the same or different and represent a D- or L-non-polar amino acid.

It is also part of the invention, in a eighteenth aspect, a peptide of formula (I) as defined in the first aspect of the invention, wherein $X_1$ represents a non-conservative amino acid with respect to L-Asp and $X_5$ represents a non-polar amino acid residue.

It is also part of the invention, in a nineteenth aspect, a peptide of formula (I) as defined in the first aspect of the invention, wherein two or more of $X_1$, $X_3$, and $X_5$ are non-conservative amino acids with respect to L-Asp, L-Ser, and L-Pro, respectively.

It is also part of the invention, in a twentieth aspect, a peptide of formula (I) as defined in the first aspect of the invention, wherein $X_1$, and $X_3$ represent non-conservative amino acids with respect to L-Asp, and L-Ser respectively, and $X_5$ represents a non-polar amino acid residue.

Finally, the following aspects, related to the peptides defined in the above aspects twelve to twenty, are also part of the invention: (a) constructs comprising a peptide as defined in any one of the aspects twelve to twenty and a cell penetrating peptide; (b) combinations comprising any one of the peptides as defined in any one of the aspects twelve to twenty, or alternatively a construct as defined in (a), and one or more immunomodulatory compounds; (c) pharmaceutical or veterinary compositions comprising any one of the peptides as defined in any one of the aspects twelve to twenty, any one of the constructs as defined in (a) or a combination as defined in (b), together with at least one veterinary or pharmaceutically acceptable excipient; (d) the therapeutic use, either as a medicament or in the treatment or prevention of a neoplastic disease of any one of the peptides as defined in any one of the aspects twelve to twenty, any one of the constructs as defined in (a), any combination as defined in (b), or any pharmaceutical or veterinary composition as defined in (c); (e) a peptide as defined in any one of the aspects twelve to twenty or a construct as defined in (a), for use in the treatment or prevention of cancer, wherein the treatment or prevention further comprises the administration of one or more immunomodulatory compounds; (f) a nucleic acid encoding any one of the peptides as defined in any one of the aspects twelve to twenty or a construct as defined in (a), wherein the cell-penetrating agent is a cell-penetrating peptide; (g) a vector comprising the nucleic acid of (f); an in vitro process for producing a peptide as defined in any one of the aspects twelve to twenty, or a construct as defined in (a), wherein the cell penetrating agent is a cell penetrating peptide, comprising growing a host cell comprising a nucleic acid as defined in (f) under conditions allowing the production of the peptide or construct and, if desired, recovering said peptide or said construct; and, (h) the use of a nucleic acid of (f) in the in vitro preparation of vectors and cells for the treatment of a neoplastic disease.

DETAILED DESCRIPTION OF THE INVENTION

Figure 1:
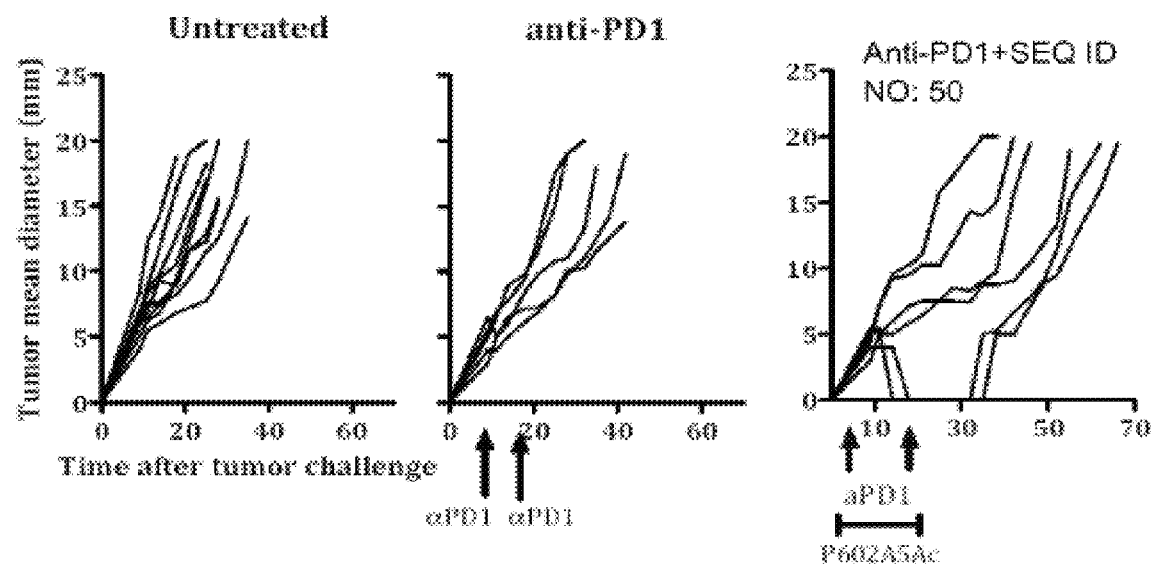
FIG. 1 each curve represents tumor mean diameter for an individual mouse injected with Hepa 129 cells, when receiving antibodies anti-PD1, antibodies anti-PD1+the peptide of sequence SEQ ID NO: 50 or nothing.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The present invention provides, in a first aspect, a peptide of formula (I) or a pharmaceutically or veterinary salt thereof.

In the present invention, the term "amino acid" refers to a molecule containing both an amino group and a carboxyl group. Amino acids can be classified by the side chain group. There are basically four different classes of amino acids determined by different side chains: (1) non-polar, (2) polar and neutral, (3) acidic and polar, (4) basic and polar.

Non-polar amino acids have side chains which are hydrocarbon alkyl groups (alkane branches) or aromatic (benzene rings) or heteroaromatic (e.g. indole ring). Illustrative non-limitative examples of common non-polar amino acids are Ala, Val, Leu, Ile, Pro, Trp, Gly, Phe, and Met.

Polar-neutral amino acids have polar but not charged groups at neutral pH in the side chain (such as hydroxyl, amide or thiol groups). Illustrative non-limitative examples of polar neutral amino acids are Ser, Thr, Cys, Tyr, Asn, and Gln.

Acid amino acids (hereinafter also referred as "acid and polar amino acid") have acidic side chains at neutral pH. These are aspartic acid or aspartate (Asp) and glutamic acid or glutamate (Glu), among others. Their side chains have carboxylic acid groups whose pKa's are low enough to lose protons, becoming negatively charged in the process.

Basic amino acids (hereinafter also referred as "basic and polar amino acid") have side chains containing nitrogen and resemble ammonia which is a base (such as amines, guanidines, or imidazole). Their pKa's are high enough that they tend to bind protons, gaining a positive charge in the process. Illustrative non-limitative examples of basic amino acids are Lys, Arg, and His.

In some embodiments the present invention refers to "a polar amino acid" in general, without specifying the charge (i.e., without specifying neutral, acid or basic polar amino acid). In those embodiments, the expression "a polar amino acid" encompasses any amino acid falling in the categories of polar-neutral, acid and basic amino acids.

Suitable amino acids include, without limitation, alpha amino acids, such as the L-isomers of alpha-amino acids of the 20 common naturally occurring alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; natural beta-amino acids (e.g., beta-alanine); and unnatural amino acids.

The term "unnatural amino acid" comprises D-isomers of the 20 common naturally occurring alpha-amino acids or amino acids of formula (A)

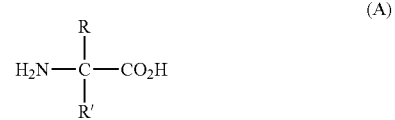

(A)

wherein R and R' have the meaning provided in Table 1 below. Further illustrative non-limitative examples of unnatural amino acids are summarized in Table 2:

TABLE 1

| Exemplary unnatural alpha-amino acids | Suitable amino acid side chains | |
|---|---|---|
| | R | R' |
| D-Alanine | —H | —$CH_3$ |
| D-Arginine | —H | —$CH_2CH_2CH_2$—NHC(=NH)$NH_2$ |
| D-Asparagine | —H | —$CH_2$C(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2$C(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2$Ph |
| D-Proline | —H | -2-(pyrrolidine) |
| D-Serine | —H | —$CH_2OH$ |
| D-Threonine | —H | —$CH_2$CH(OH)($CH_3$) |
| D-Tryptophan | —H | —$CH_2$-3-(1H-indole) |
| D-Tyrosine | —H | —$CH_2$-(p-hydroxyphenyl) |
| D-Valine | —H | -isopropyl |
| Di-vinyl | —CH=$CH_2$ | —CH=$CH_2$ |
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2$C(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2$C(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |

TABLE 2

| Aad | 2-Aminoadipic acid |
|---|---|
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4 Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| aIle | allo-Isoleucine |
| Nva | Norvaline |
| Nle | Norleucine |
| Orn | Ornithine |

Each one of the amino acids forming the peptide of the invention can have, independently from the others, L- or D-configuration. In one embodiment of the first aspect of the invention, optionally in combination with any one of the embodiments provided below, the amino acid residue at the amine-terminal end N(t) and/or the amino acid residue at the carboxyl-terminal end C(t) has D-configuration.

Amino acids used in the preparation of the peptides of the present invention may be prepared by organic synthesis, or obtained by other routes, such as, for example, degradation of or isolation from a natural source.

The expression "wherein at least one of $X_1$ to $X_5$ is selected from the group consisting of the list: $X_1$ is an amino acid other than L-Asp; $X_2$ is an amino acid other than L-Phe; $X_3$ is an amino acid other than L-Ser; $X_4$ is an amino acid other than L-Lys; and $X_5$ is an amino acid other than L-Pro" encompasses that when one of the amino acids $X_1$ to $X_5$ is selected from the list, the other four X radicals mean any amino acid as defined herein above; that when two of the amino acids $X_1$ to $X_5$ are selected from the list, the other three X radicals mean any amino acid as defined herein above; that when three of the amino acids $X_1$ to $X_5$ are selected from the list, the other two X radicals mean any amino acid as defined herein above; and that when four of the amino acids $X_1$ to $X_5$ are selected from the list, the X radical remaining means any amino acids as defined herein above.

In the present invention, the expression "an amino acid other than" refers either to the corresponding D-amino acid or to a different amino acid, of the same or different polarity nature. For example, when reference is made to "an amino acid other than L-Asp", the amino acid can be D-Asp or an amino acid falling in the same or different category of polarity.

When reference is made in the present invention to a "non-conservative" amino acid with respect to a particular amino acid, reference is made to amino acids falling in categories of different polarity nature with respect to the amino acid of reference. That is, the replacement of a particular L-amino acid by the same one with D-configuration does not represent a non-conservative change. Illustrative non-limitative examples of non-conservative amino acid changes are: (a) a polar amino acid (either neutral or charged polar amino acid) by a nonpolar amino acid (such as Ala, Val, Leu, Ile, and Pro); (b) a charged polar amino acid (either basic o acid) by a nonpolar or polar-neutral amino acid; (c) an acid polar amino acid by a nonpolar, polar-neutral, or basic charged amino acids; and (d) a basic polar amino acid by a nonpolar, polar-neutral, or acidic charged amino acids, among others.

In the first aspect of the invention it is encompassed a peptide having at least 80% of sequence identity with peptide of formula (I) which maintains the ability to bind FoxP3 and inhibit FoxP3 activity in vitro and/or in vivo.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In one embodiment, the sequence of the first aspect of the invention has an identity of 80%, 81%, 82%, 83%, 84%, 85%, 86%, 87%, 88%, 89%, 90%, 91%, 92%, 93%, 94%, or 95%, with respect to the sequence of formula (I) and maintains the ability to bind FoxP3 and inhibit FoxP3 activity in vitro and/or in vivo.

In the first aspect of the invention it is also encompassed a fragment of the peptide defined in (a) or in (b), wherein said fragment comprises a portion of at least 11 consecutive amino acids of the peptide defined in (a) or in (b).

The term "fragment", as used in the present description, relates to a peptide comprising a portion of at least 11 consecutive amino acids of the peptide of general formula (I) defined in section a), or of the variant defined in section b), i.e., a sequence of at least 11 contiguous amino acids comprised within the amino acid sequence of general formula (I) mentioned in said section a), or of the variant defined in section b), maintaining the capacity to bind to scurfin and inhibit FoxP3 activity in vitro and/or in vivo. In a particular embodiment, the peptide of the invention is a fragment which differs from the peptide of general formula (I) defined in a), or from the variant defined in b), in the deletion of one or more contiguous amino acids in the C(t). In another embodiment, optionally in combination with any one of the embodiments provided below, the peptide of the invention is a fragment as defined in (c), which comprises 13 or 14 contiguous amino acids of the amino acid sequence of general formula (I) mentioned in section a), or of the variant defined in section b). In another embodiment, optionally in combination with any one of the embodiments provided below, the peptide of the invention is a fragment which comprises 13 or 14 contiguous amino acids of the amino acid sequence of general formula (I) mentioned in section a), or of the variant defined in section b), the one or two amino acids from the whole sequence of formula (I) being deleted from the carboxyl-terminal end. In any of these embodiments, the 11-, 12-, 13- or 14-amino acid fragment can comprise modified N- and/or C-terminal end(s), either by the inclusion of a head-to-tail linker or by the chemical derivatization of the N-terminal end by alkylation and/or of the C-terminal end by amidation, as it has been explained above. Alternatively, the fragment can have free N- and/or C-terminal ends (i.e., in the form of —NH$_2$ and —COOH). In this last embodiment, the fragment will then include at least one of the residues identified in the peptide of formula (I) as "X$_1$" to "X$_5$", wherein said at least one residue is selected from the group consisting of: X$_1$ is an amino acid other than L-Asp; X$_2$ is an amino acid other than L-Phe; X$_3$ is an amino acid other than L-Ser; X$_4$ is an amino acid other than L-Lys; and X$_5$ is an amino acid other than L-Pro.

The peptide of the invention is characterized by its capacity to bind FoxP3, and advantageously, by its capacity to inhibit the biological activity of FoxP3. The capacity of a peptide to bind to FoxP3 can be determined by means of any suitable method which allows determining the binding between two molecules (e.g., by means of an affinity assay), said method comprising putting FoxP3 in contact with the peptide to be assayed under conditions allowing the binding of said peptide to FoxP3 and evaluating the binding between the peptide and FoxP3. In a particular embodiment, said affinity assay can be carried out using the surface plasmon resonance (SPR) technique or similar techniques using radioactively labeled FoxP3, or, alternatively, radioactively labelling the peptide to be assayed. This type of affinity assay generally comprises putting FoxP3, e.g., immobilized in the wells of a plate, in contact with the peptide the capacity to bind to FoxP3 of which is to be known, and, after incubating for a suitable time period, analysing the binding of the peptide to FoxP3. The peptides with low affinity for FoxP3 are eliminated by means of washings whereas the peptides with higher affinity remain bound to FoxP3 and can be released by breaking the molecular interactions between both molecules, which can be carried out by lowering the pH, for example.

The peptide of the invention is advantageously characterized not only by its capacity to bind to FoxP3 but also by its capacity to inhibit the biological activity of FoxP3 and, as a result, indirectly regulate or block, transiently or temporarily, the immunosuppressive activity of Treg lymphocytes. The present inventors have found that the peptides bind to the intermediate region of FOXP3 and inhibit FOXP3 homodimerization and FOXP3-AML1 heterodimerization. The capacity of a peptide to inhibit the biological activity of FoxP3 can be analysed, in vitro, by any suitable method illustrating such effect. The particular assays used in the present invention is based on determining the FoxP3/RunX1 heterodimerization (as disclosed in Ono M. et al., "Foxp3 controls regulatory T-cell function by interacting with AML1/Runx1", Nature, vol. 446(7136), pages 685-689) as well as FoxP3/FoxP3 homodimerization (as disclosed in Son X. et al., "Structural and biological features of FOXP3 dimerization relevant to regulatory T cell function", Cell Rep., vol. 1(6), pages 665-75) which are recognized as valid tests to determine the inhibitory effect of the peptides of the invention on FoxP3. In both disclosures were reported that disrupting the target interaction (either FoxP3-RunX1 or FoxP3-FoxP3), Treg activity was negatively affected, being reduced or even suppressed. Thus, peptide's Treg inhibition activity can be predicted by determining the binding ability of the tested peptide to FoxP3. Following these protocols the present inventors found that there was a significant correlation between peptide ability to inhibit Treg activity and their capacity to bind FOXP3 (in SPR assays) ($p<0.001$), or inhibit FOXP3 homodimerization ($p=0.0062$) or FOXP3-AML1 heterodimerization ($p<0.05$).

Likewise, the pharmaceutically acceptable salts of the peptide of the invention are within the scope of this invention. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate. Likewise, the term "veterinary acceptable salt" means suitable for use in a non-human animal.

In the present invention the term "alkyl", "alkenyl", and "alkynyl" encompasses both lineal and branched hydrocarbon chains.

Illustrative non-limitative examples of "alkyl" are: methyl (C1), ethyl (C2), propyl (C3), isopropyl (C3), isobutyl (C4), sec-butyl (C4), tert-butyl (C4), pentyl (C5), hexyl, (C6), heptyl (C7), octyl (C9), nonyl (C9), and decyl (C10), among others.

Illustrative non-limitative examples of "alkenyl" are: ethenyl (C2), propen-1-yl (C3), propen-2-yl (C3), buten-1-yl (C4) and hexen-1-yl (C6), among others.

Illustrative non-limitative examples of "alkynyl" are: ethynyl (C2), 1-propynyl (C3), 2-propynyl (C3) and 1-hexynyl ($C_6$), among others.

The term "halogen" refers to the group in the periodic table consisting of five chemically related elements: fluorine (F), chlorine (Cl), bromine (Br), iodine (I), and astatine (At).

As it is shown below, when the peptide of formula (I) comprises a staple of the type head-to-tail, it is achieved a substantial improvement in the peptide stability, in comparison to the peptide without the staple.

Therefore, in one embodiment of the first aspect of the invention, optionally in combination with any one of the embodiments provided above or below, $R_1$ and $R_2$ form a linker birradical as defined above.

In another embodiment of the first aspect of the invention, optionally in combination with any one of the embodiments provided above or below, the peptide is one, wherein:

$R_1$ is —C(=O)—CH$_2$—NH—C(=O)—(C$_1$-C$_5$)alkyl or —C(=O)—(C$_1$-C$_{20}$)alkyl; and one of $R_2$ and $R_2'$ is hydrogen and the other is —COOH; or alternatively $R_1$ is hydrogen;

one of $R_2$ and $R_2'$ is hydrogen and the other is —C(=O)NR$_3$R$_4$; and $R_3$ and $R_4$ are as defined in the first aspect of the invention; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)NR$_3$R$_4$; and $R_3$ and $R_4$ are as defined in the first aspect of the invention.

In another embodiment of the first aspect of the invention, optionally in combination with any one of the embodiments provided above or below, the peptide is one, wherein:

$R_1$ is —C(=O)—CH$_2$—NH—C(=O)—(C$_1$-C$_5$)alkyl; and one of $R_2$ and $R_2'$ is hydrogen and the other is —COOH; or alternatively $R_1$ is hydrogen;

one of $R_2$ and $R_2'$ is hydrogen and the other is —C(=O)NR$_3$R$_4$; and $R_3$ and $R_4$ are as defined in in the first aspect of the invention; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$; and $R_3$ and $R_4$ are as defined in the first aspect of the invention.

In another embodiment of the first aspect of the invention, optionally in combination with any one of the embodiments provided above or below, the peptide of formula (I) is one wherein $R_1$ and $R_2$ form a linker birradical as defined in the first aspect of the invention and:

(i) $X_1$ is L-Asp, $X_2$ is L-Phe, $X_3$ is L-Ser, $X_4$ is L-Lys, and $X_5$ is L-Pro; or, alternatively, (ii) at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X's amino acids represent any amino acid.

In another embodiment of the first aspect of the invention, optionally in combination with any one of the embodiments provided above or below, the peptide of formula (I) is one wherein $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention; and:

(i) $X_1$ is L-Asp, $X_2$ is L-Phe, $X_3$ is L-Ser, $X_4$ is L-Lys, and $X_5$ is L-Pro; or, alternatively, (ii) at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X's amino acids represent any amino acid.

In another embodiment of the first aspect of the invention, optionally in combination with any one of the embodiments provided above or below, one of $X_1$ to $X_5$ is selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; $X_5$ is an amino acid other than L-Pro; and the other X radicals represent any amino acid. In another embodiment, optionally in combination with any one of the embodiments provided above or below, $X_1$ is an amino acid other than L-Asp and $X_2$ to $X_5$ means any amino acid. In another embodiment, $X_3$ is an amino acid other than L-Ser, and $X_1$, $X_2$, $X_4$, and $X_5$ represent any amino acid. In another embodiment, optionally in combination with any one of the embodiments provided above or below, $X_5$ represents an amino acid other than L-Pro, and $X_1$ to $X_4$ represent any amino acid.

In another embodiment of the first aspect of the invention, optionally in combination with any one of the embodiments provided above or below, two of $X_1$ to $X_5$ are selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; $X_5$ is an amino acid other than L-Pro; and the other X radicals represent any amino acid. In another embodiment of the first aspect of the invention, optionally in combination with any one of the embodiments provided above or below, $X_1$ is an amino acid other than L-Asp, $X_3$ is an amino acid other than L-Ser, and $X_2$, $X_4$ and $X_5$ represent any amino acid. In another embodiment, optionally in combination with any one of the embodiments provided above or below, $X_1$ is an amino acid other than L-Asp, $X_5$ is an amino acid other L-Pro, and $X_2$, $X_3$, and $X_4$ represent any amino acid.

In another embodiment of the first aspect of the invention, three of $X_1$ to $X_5$ are selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; $X_5$ is an amino acid other than L-Pro; and the other X radicals represent any amino acid. In one embodiment, $X_1$ is an amino acid other than L-Asp; $X_3$ is an amino acid other than L-Ser; $X_5$ is an amino acid other than L-Pro; and $X_2$ and $X_4$ represent any amino acid.

The present inventors have found that when the peptide of the invention comprises both a linker birradical and at least one mutation in at least one of the positions $X_1$ to $X_5$ (i.e., at least one of $X_1$ to $X_5$ is selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; $X_5$ is an amino acid other than L-Pro), a synergistic effect in the binding to FoxP3 is achieved. As it is shown below, by mutating, for example, positions 2 and 5 of the native p60 sequence (e.g., sequence SEQ ID NO: 42) an increase of about 400% in the binding to FoxP3 was achieved with respect to SEQ ID NO: 1. When native p60 sequence were cycled such as the amino and carboxy terminal groups were forming a head-to-tail linker (i.e., sequence SEQ ID NO: 49), there was an increase of about 500% in binding to FoxP3 with respect to SEQ ID NO: 1. But when, p60 peptide was modified to include both, the two mutations (at positions 2 and 5) and the cyclization, such as the amino and carboxy terminal groups were forming a head-to-tail linker (i.e., sequence SEQ ID NO: 50), the binding to FoxP3 was increased more than 2100% with respect to p60 sequence. That is, the combination of a staple and one or more mutations (amino acid substitutions) at any one of the positions $X_1$ to $X_5$ confers a remarkable improvement in the binding to FoxP3. These data further supports the critical role of the head-to-tail staples in improving the efficiency of p60 peptide.

Thus, in one embodiment of the first aspect of the invention, optionally in combination with any one of the embodiments provided above or below, the peptide is one of formula (I) wherein $R_1$ and $R_2$ form a birradical linker as defined in the first aspect of the invention, and at least one of $X_1$ to $X_5$ is selected from the group consisting of: $X_1$ is an amino acid other than L-Asp; $X_2$ is an amino acid other than L-Phe; $X_3$ is an amino acid other than L-Ser; $X_4$ is an amino acid other than L-Lys; $X_5$ is an amino acid other than L-Pro; and the remaining X's radicals represent any amino acid.

In another embodiment of the first aspect of the invention, optionally in combination with any one of the embodiments provided above or below, the peptide is one of formula (I) wherein $R_1$ is $—C(═O)—CH_2—NH—C(═O)—(C_1\text{-}C_5)$ alkyl or $—C(═O)—(C_1\text{-}C_{20})$alkyl; one of $R_2$ and $R_2'$ is hydrogen and the other is —COOH; at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X radicals represent any amino acid.

In another embodiment of the first aspect of the invention, optionally in combination with any one of the embodiments provided above or below, the peptide is one of formula (I) wherein $R_1$ is $—C(═O)—CH_2—NH—C(═O)—(C_1\text{-}C_5)$ alkyl; one of $R_2$ and $R_2'$ is hydrogen and the other is —COOH; at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X radicals represent any amino acid.

In another embodiment of the first aspect of the invention, optionally in combination with any one of the embodiments provided above or below, the peptide is one of formula (I) wherein $R_1$ is hydrogen; one of $R_2$ and $R_2'$ is hydrogen and the other is $—C(═O)NR_3R_4$, wherein $R_3$ and $R_4$ are as defined in the first aspect of the invention; and at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X radicals represent any amino acid.

In another embodiment of the first aspect of the invention, optionally in combination with any one of the embodiments provided above or below, the peptide is one of formula (I) wherein $R_1$ is $—C(═O)—CH_2—NH—C(═O)—(C_1\text{-}C_5)$ alkyl or $—C(═O)—(C_1\text{-}C_{20})$alkyl; one of $R_2$ and $R_2'$ is hydrogen and the other is $—C(═O)NR_3R_4$, wherein $R_3$ and $R_4$ are as defined in the first aspect of the invention; and at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X radicals represent any amino acid.

In another embodiment of the first aspect of the invention, optionally in combination with any one of the embodiments provided above or below, the peptide is one of formula (I) wherein $R_1$ is $—C(═O)—CH_2—NH—C(═O)—(C_1\text{-}C_5)$ alkyl; one of $R_2$ and $R_2'$ is hydrogen and the other is $—C(═O)NR_3R_4$, wherein $R_3$ and $R_4$ are as defined in the first aspect of the invention; and at least one of $X_1$ to $X_5$ is selected from the group consisting of: $X_1$ is an amino acid other than L-Asp, $X_2$ is an amino acid other than L-Phe, $X_3$ is an amino acid other than L-Ser, $X_4$ is an amino acid other than L-Lys, and $X_5$ is an amino acid other than L-Pro; and the remaining X radicals represent any amino acid.

The present inventors have surprisingly found that a substantial improvement in FoxP3 binding occurs when at least one of $X_1$ to $X_5$ is a D-amino acid. In particular, it was found that when in the peptide of the invention $X_1$ was a D-Asp residue (instead of a L-Asp residue, which is the one at position 2 in p60 sequence), there was a 2-fold increase in FoxP3 binding.

Thus, in one embodiment of the first aspect of the invention, optionally in combination with any one of the embodiments provided above or below, at least one of $X_1$ to $X_5$ is a D-amino acid. In another embodiment of the first aspect of the invention, optionally in combination with any one of the embodiments provided above or below, one, two or three of $X_1$ to $X_5$ is/are D-amino acids.

The present inventors have also surprisingly found that when the substitution of amino acids at positions 2, 3, 5, 8, and 11, is for a non-conservative amino acid, the improvement in the ability to bind to FoxP3 is even higher when compared to other conservative substitutions.

Thus, in another embodiment of the first aspect of the invention, optionally in combination with any one of the embodiments provided above or below, at least one of the amino acids $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ and $R_2$ form a birradical linker as defined in the first aspect of the invention, and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is —C(═O)—$CH_2$—NH—C(═O)—($C_1$-$C_5$) alkyl or —C(═O)—($C_1$-$C_{20}$)alkyl; one of $R_2$ and $R_2$' is hydrogen and the other is —COOH; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is —C(═O)—$CH_2$—NH—C(═O)—($C_1$-$C_5$) alkyl; one of $R_2$ and $R_2$' is hydrogen and the other is —COOH; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is hydrogen; one of $R_2$ and $R_2$' is hydrogen and the other is —C(═O)$NR_3R_4$, wherein $R_3$ and $R_4$ are as defined in the first aspect of the invention; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is —C(═O)—$CH_2$—NH—C(═O)—($C_1$-$C_5$) alkyl or —C(═O)—($C_1$-$C_{20}$)alkyl; one of $R_2$ and $R_2$' is hydrogen and the other is —C(═O)$NR_3R_4$, wherein $R_3$ and $R_4$ are as defined in the first aspect of the invention; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is —C(═O)—$CH_2$—NH—C(═O)—($C_1$-$C_5$) alkyl; one of $R_2$ and $R_2$' is hydrogen and the other is —C(═O)$NR_3R_4$, wherein $R_3$ and $R_4$ are as defined in the first aspect of the invention; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one of formula (I) wherein $R_1$ is hydrogen; one of $R_2$ and $R_2$' is hydrogen and the other is —C(═O)OH; and at least one of $X_1$ to $X_5$ is selected from the group consisting of: $X_1$ is an amino acid which is non-conservative with respect to L-Asp; $X_2$ is an amino acid which is non-conservative with respect to L-Phe; $X_3$ is an amino acid which is non-conservative with respect to L-Ser; $X_4$ is an amino acid which is non-conservative with respect to L-Lys; and $X_5$ is an amino acid which is non-conservative with respect to L-Pro.

In another embodiment of the first aspect of the invention, optionally in combination with any one of the embodiments provided above or below, the peptide is one wherein one of $X_1$ to $X_5$ is a non-conservative amino acid residue as defined above.

In another embodiment of the first aspect of the invention, optionally in combination with any one of the embodiments provided above or below, the peptide is one wherein $R_1$ and $R_2$ form a linker birradical as defined above, and one of $X_1$ to $X_5$ is a non-conservative amino acid residue as defined above.

In another embodiment of the first aspect of the invention, optionally in combination with any one of the embodiments provided above or below, the peptide is one of formula (I) wherein:

$R_1$ is hydrogen;

one of $R_2$ and $R_2'$ is hydrogen and the other is —C(=O)$NR_3R_4$;

$R_3$ and $R_4$ are as defined in the first aspect of the invention;

one of $X_1$ to $X_5$ is a non-conservative amino acid residue as defined above; and the remaining X radicals represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

one of $X_1$ to $X_5$ is a non-conservative amino acid residue as defined above; and the remaining X radicals represent any amino acid; or, alternatively, $R_1$ is hydrogen;

one of $R_2$ and $R_2'$ is hydrogen and the other is —C(=O)OH;

one of $X_1$ to $X_5$ is a non-conservative amino acid residue as defined above; and the remaining X radicals represent any amino acid.

In another embodiment of the first aspect of the invention, optionally in combination with any one of the embodiments provided above or below, the peptide is one wherein $R_1$ is —C(=O)—CH$_2$—NH—C(=O)—(C$_1$-C$_5$)alkyl, or —C(=O)—(C$_1$-C$_{20}$)alkyl, one of $R_2$ and $R_2'$ is hydrogen and the other is —C(=O)NR$_3$R$_4$, $R_3$ and $R_4$ are as defined in the first aspect of the invention, and one of $X_1$ to $X_5$ is a non-conservative amino acid residue as defined above.

In another embodiment of the first aspect of the invention, optionally in combination with any one of the embodiments provided above or below, the peptide is one wherein $R_1$ is —C(=O)—CH$_2$—NH—C(=O)—(C$_1$-C$_5$)alkyl, one of $R_2$ and $R_2'$ is hydrogen and the other is —C(=O)NR$_3$R$_4$, $R_3$ and $R_4$ are as defined in the first aspect of the invention, and one of $X_1$ to $X_5$ is a non-conservative amino acid residue.

In another embodiment of the first aspect of the invention, optionally in combination with any one of the embodiments provided above or below, the peptide of formula (I) is one wherein just one of $X_1$ to $X_5$ is a non-conservative amino acid residue and the other X's radicals are conservative amino acid residues.

In another embodiment of the first aspect of the invention, optionally in combination with any one of the embodiments provided above or below, $X_1$ is an amino acid which is non-conservative with respect to L-Asp, and $X_2$ to $X_5$ represent any amino acid.

In another embodiment of the first aspect of the invention, optionally in combination with any one of the embodiments provided above or below, when $R_1$ is H; one of $R_2$ and $R_2'$ is hydrogen and the other is —C(=O)OH; $X_2$ represents L-Phe; $X_3$ represents L-Ser, $X_4$ represents L-Lys; $X_5$ represents L-Pro; and $X_1$ represents a non-polar amino acid, then $X_1$ is selected from: Gly, Val, Leu, Ile, Pro, Phe, Trp, Met (either with D- or L-configuration).

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is the only non-conservative amino acid residue selected from Ala, Ser, Tyr, Trp, Asn and Lys, in any configuration, L- or D-; and $X_2$ to $X_5$ represent conservative amino acids with respect to L-Phe, L-Ser, L-Lys, and L-Pro, respectively. In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is the only non-conservative amino acid residue and it is selected from D-Ala, L- or D-Ser, L- or D-Tyr, L- or D-Trp, L- or D-Asn and L- or D-Lys; and $X_2$ to $X_5$ represent conservative amino acids with respect to L-Phe, L-Ser, L-Lys, and L-Pro, respectively. In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is the only non-conservative amino acid residue and it is selected from L- or D-Ser, L- or D-Tyr, L- or D-Trp, L- or D-Asn and L- or D-Lys; and $X_2$ to $X_5$ represent conservative amino acids with respect to L-Phe, L-Ser, L-Lys, and L-Pro, respectively.

In another embodiment of the first aspect of the invention, optionally in combination with any one of the embodiments provided above or below, $X_3$ is an amino acid which is non-conservative with respect to L-Ser and $X_1$, $X_2$, $X_4$ and $X_5$ represent any amino acid. In another embodiment of the first aspect of the invention, optionally in combination with any one of the embodiments provided above or below, $X_3$ is the only non-conservative amino acid residue; and $X_1$, $X_2$, $X_4$ and $X_5$ represent conservative amino acid residues with respect L-Asp, L-Phe, L-Lys and L-Pro, respectively.

In another embodiment of the first aspect of the invention, optionally in combination with any one of the embodiments provided above or below, $X_5$ is an amino acid which is non-conservative with respect to L-Pro and $X_1$ to $X_4$ represent any amino acid. In another embodiment of the first aspect of the invention, optionally in combination with any one of the embodiments provided above or below, $X_5$ is the only non-conservative amino acid residue; and $X_1$ to $X_4$ represent conservative amino acid residues with respect to L-Asp, L-Phe, L-Ser, and L-Lys, respectively.

In another embodiment of the first aspect of the invention, optionally in combination with any one of the embodiments provided above or below, the peptide of formula (I) is one wherein $R_1$ and $R_2$ form a linker birradical as defined in the first aspect of the invention, $X_1$ is an amino acid which is non-conservative with respect to L-Asp, and $X_2$ to $X_5$ represent any amino acid.

In another embodiment of the first aspect of the invention, optionally in combination with any one of the embodiments provided above or below, the peptide of formula (I) is one wherein $R_1$ and $R_2$ form a linker birradical as defined in the first aspect of the invention, $X_3$ is an amino acid which is non-conservative with respect to L-Ser and $X_1$, $X_2$, $X_4$ and $X_5$ represent any amino acid.

In another embodiment of the first aspect of the invention, optionally in combination with any one of the embodiments provided above or below, the peptide of formula (I) is one wherein $R_1$ and $R_2$ form a linker birradical as defined in the first aspect of the invention, $X_5$ is an amino acid which is non-conservative with respect to L-Pro and $X_1$ to $X_4$ represent any amino acid.

In another embodiment of the first aspect of the invention, optionally in combination with any one of the embodiments provided above or below, the peptide is one of formula (I) wherein:

$R_1$ is hydrogen;

one of $R_2$ and $R_2'$ is hydrogen and the other is —C(=O)$NR_3R_4$;

$R_3$ and $R_4$ are as defined in the first aspect of the invention;

$X_1$ is an amino acid which is non-conservative with respect to L-Asp; and $X_2$ to $X_5$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp; and $X_2$ to $X_5$ represent any amino acid; or, alternatively, $R_1$ is hydrogen;

one of $R_2$ and $R_2'$ is hydrogen and the other is —C(=O)OH;

$X_1$ is an amino acid which is non-conservative with respect to L-Asp, and $X_2$ to $X_5$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp; and, $X_2$ to $X_5$ represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp, and $X_2$ to $X_5$ represent any amino acid.

In another embodiment of the first aspect of the invention, optionally in combination with any one of the embodiments provided above or below, the peptide is one of formula (I) wherein:

$R_1$ is hydrogen;

one of $R_2$ and $R_2'$ is hydrogen and the other is —C(=O)NR$_3$R$_4$;

$R_3$ and $R_4$ are as defined in the first aspect of the invention;

$X_3$ is an amino acid which is non-conservative with respect to L-Ser; and $X_1$, $X_2$, and $X_4$ to $X_5$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_3$ is an amino acid which is non-conservative with respect to L-Ser; and $X_1$, $X_2$, and $X_4$ to $X_5$ represent any amino acid; or, alternatively, $R_1$ is hydrogen;

one of $R_2$ and $R_2'$ is hydrogen and the other is —C(=O)OH;

$X_3$ is an amino acid which is non-conservative with respect to L-Ser; and $X_1$, $X_2$, and $X_4$ to $X_5$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_3$ is an amino acid which is non-conservative with respect to L-Ser; and $X_1$, $X_2$, and $X_4$ to $X_5$ represent any amino acid; or, alternatively, $R_1$ is —C(=O)—CH$_2$—NH—C(=O)—(C$_1$-C$_5$)alkyl, one of $R_2$ and $R_2'$ is hydrogen and the other is —C(=O)NR$_3$R$_4$;

$R_3$ and $R_4$ are as defined in the first aspect of the invention, $X_3$ is an amino acid which is non-conservative with respect to L-Ser; and $X_1$, $X_2$, $X_4$ and $X_5$ represent any amino acid.

In another embodiment of the first aspect of the invention, optionally in combination with any one of the embodiments provided above or below, the peptide is one of formula (I) wherein:

$R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_5$ is an amino acid which is non-conservative with respect to L-Pro; and $X_1$ to $X_4$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_5$ is an amino acid which is non-conservative with respect to L-Pro; and $X_1$ to $X_4$ represent any amino acid; or, alternatively, $R_1$ is hydrogen;

one of $R_2$ and $R_2'$ is hydrogen and the other is —C(=O)OH;

$X_5$ is an amino acid which is non-conservative with respect to L-Pro; and $X_1$ to $X_4$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_5$ is an amino acid which is non-conservative with respect to L-Pro; and $X_1$ to $X_4$ represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined in the first aspect of the invention;

$X_5$ is an amino acid which is non-conservative with respect to L-Pro; and $X_1$ to $X_4$ represent any amino acid.

In another embodiment of the first aspect of the invention, optionally in combination with any one of the embodiments provided above or below, the peptide is one wherein two of $X_1$ to $X_5$ are non-conservative amino acid residues as defined above.

In another embodiment of the first aspect of the invention, optionally in combination with any one of the embodiments provided above or below, the peptide is one wherein $R_1$ and $R_2$ form a birradical linker as defined in the first aspect of the invention, and two of $X_1$ to $X_5$ are non-conservative amino acid residues as defined above.

In another embodiment of the first aspect of the invention, optionally in combination with any one of the embodiments provided above or below, the peptide is one wherein:

$R_1$ is hydrogen;

one of $R_2$ and $R_2'$ is hydrogen and the other is —C(=O) $NR_3R_4$, wherein $R_3$ and $R_4$ are as defined in the first aspect of the invention;

two of $X_1$ to $X_5$ are non-conservative amino acid residues as defined above, and the other X's radicals represent any amino acid; or, alternatively, $R_1$ is —C(=O)—$CH_2$—NH—C(=O)—($C_1$-$C_5$)alkyl or —C(=O)—($C_1$-$C_{20}$)alkyl;

one of $R_2$ and $R_2'$ is hydrogen and the other is —C(=O) OH;

two of $X_1$ to $X_5$ are non-conservative amino acid residues as defined above, and the other X's radicals represent any amino acid; or alternatively, $R_1$ is hydrogen;

one of $R_2$ and $R_2'$ is hydrogen and the other is —C(=O) OH;

two of $X_1$ to $X_5$ are non-conservative amino acid residues as defined above, and the other X's radicals represent any amino acid; or, alternatively, $R_1$ is —C(=O)—$CH_2$—NH—C(=O)—($C_1$-$C_5$)alkyl, or —C(=O)—($C_1$-$C_{20}$)alkyl;

one of $R_2$ and $R_2'$ is hydrogen and the other is —C(=O) $NR_3R_4$;

$R_3$ and $R_4$ are as defined in the first aspect of the invention;

two of $X_1$ to $X_5$ are non-conservative amino acid residues as defined above, and the other X's radicals represent any amino acid; or, alternatively.

$R_1$ is —C(=O)—$CH_2$—NH—C(=O)—($C_1$-$C_5$)alkyl;

one of $R_2$ and $R_2'$ is hydrogen and the other is —C(=O) $NR_3R_4$;

$R_3$ and $R_4$ are as defined above;

and two of $X_1$ to $X_5$ are non-conservative amino acid residues as defined above.

In another embodiment of the first aspect of the invention, optionally in combination with any one of the embodiments provided above or below, $X_1$ is an amino acid which is non-conservative with respect to L-Asp; $X_3$ is an amino acid which is non-conservative with respect to L-Ser; and the remaining $X_2$, $X_4$, and $X_5$ represent any amino acid.

In another embodiment of the first aspect of the invention, optionally in combination with any one of the embodiments provided above or below, $X_1$ is an amino acid which is non-conservative with respect to L-Asp; $X_3$ is an amino acid which is non-conservative with respect to L-Ser; and the remaining $X_2$, $X_4$, and $X_5$ represent conservative amino acids with respect L-Phe, L-Lys, and L-Pro, respectively.

In another embodiment of the first aspect of the invention, optionally in combination with any one of the embodiments provided above or below, when $R_1$ is H; one of $R_2$ and $R_2'$ is hydrogen and the other is —C(=O)OH; $X_2$ represents L-Phe; k represents L-Lys; $X_5$ represents L-Pro; and both $X_1$ and $X_3$ represent the same non-polar amino acid with the same configuration, then $X_1$ and $X_3$ are selected from the group consisting of: D- or L-Gly, D- or L-Val, D- or L-Leu, D- or L-Ile, D- or L-Phe, D- or L-Pro, D- or L-Trp, D- and L-Met.

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is an amino acid which is non-conservative with respect to L-Asp; $X_3$ is selected from D- or L-Gly, D- or L-Val, D- or L-Leu, D- or L-Ile, D- or L-Phe, D- or L-Pro, D- or L-Trp, D- or L-Met, an acid amino acid and a basic amino acid; and the remaining $X_2$, $X_4$, and $X_5$ represent conservative amino acids with respect L-Phe, L-Lys, and L-Pro, respectively.

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is selected from D- or L-Gly, D- or L-Val, D- or L-Leu, D- or L-Ile, D- or L-Phe, D- or L-Pro, D- or L-Trp, D- or L-Met, a polar-neutral amino acid and a basic amino acid; $X_3$ is an amino acid which is non-conservative with respect L-Ser; and the remaining $X_2$, $X_4$, and $X_5$ represent any amino acid.

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is selected from D- or L-Gly, D- or L-Val, D- or L-Leu, D- or L-Ile, D- or L-Phe, D- or L-Pro, D- or L-Trp, D- or L-Met, a polar-neutral amino acid and a basic amino acid; $X_3$ is an amino acid which is non-conservative with respect L-Ser; and the remaining $X_2$, $X_4$, and $X_5$ represent conservative amino acids with respect L-Phe, L-Lys, and L-Pro, respectively.

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is an amino acid which is non-conservative with respect to L-Asp; $X_3$ is selected from D- or L-Gly, D- or L-Val, D- or L-Leu, D- or L-Ile, D- or L-Phe, D- or L-Pro, D- or L-Trp, D- or L-Met, an acid and a basic amino acid; and the remaining $X_2$, $X_4$, and $X_5$ represent any amino acid.

In another embodiment of the first aspect of the invention, optionally in combination with any one of the embodiments provided above or below, the peptide of formula (I) is one wherein $R_1$ is H; one of $R_2$ and $R_2'$ is hydrogen and the other is —C(=O)OH; $X_1$ is an amino acid which is non-conservative with respect to L-Asp; $X_3$ is selected from D- or L-Gly, D- or L-Val, D- or L-Leu, D- or L-Ile, D- or L-Phe, D- or L-Pro, D- or L-Trp, D- or L-Met, an acid and a basic amino acid; and the remaining $X_2$, $X_4$, and $X_5$ represent conservative amino acids with respect L-Phe, L-Lys, and L-Pro, respectively.

In another embodiment of the first aspect of the invention, optionally in combination with any one of the embodiments provided above or below, the peptide is one wherein:

$R_1$ and $R_2$ form a birradical linker as defined above;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid; or, alternatively, $R_1$ is hydrogen;

one of $R_2$ and $R_2'$ is hydrogen and the other is —C(=O) $NR_3R_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid; or, alternatively, $R_1$ is —C(=O)—$CH_2$—NH—C(=O)—($C_1$-$C_5$)alkyl or —C(=O)—($C_1$-$C_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid; or, alternatively, $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser; and the remaining $X_2$, $X_4$, and $X_5$ represent any amino acid.

In another embodiment of the first aspect of the invention, optionally in combination with any one of the embodiments provided above or below, the peptide is one wherein:

$R_1$ and $R_2$ form a birradical linker as defined above;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively; or, alternatively, $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser; and the remaining $X_2$, $X_4$, and $X_5$ represent conservative changes with respect to L-Phe, L-Lys and L-Pro, respectively.

In another embodiment of the first aspect of the invention, optionally in combination with any one of the embodiments provided above or below, $X_1$ is an amino acid which is non-conservative with respect to L-Asp; $X_3$ is an amino acid which is non-conservative with respect to L-Ser; and $X_5$ is a non-polar amino acid or a basic polar amino acid.

In another embodiment of the first aspect of the invention, optionally in combination with any one of the embodiments provided above or below, the peptide is one wherein:

$R_1$ and $R_2$ form a birradical linker as defined above;

$X_1$ is an amino acid which is non-conservative with respect to L-Asp;

$X_3$ is an amino acid which is non-conservative with respect to L-Ser;

$X_5$ is a non-polar amino acid or a basic polar amino acid; and $X_2$ and $X_4$ represent any amino acid; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a non-polar amino acid or a basic polar amino acid; and $X_2$ and $X_4$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)H;

$X_1$ is an amino acid which is non-conservative with respect to L-Asp;

$X_3$ is an amino acid which is non-conservative with respect to L-Ser;

$X_5$ is a non-polar amino acid or a basic polar amino acid; and $X_2$ and $X_4$ represent any amino acid; or, alternatively, $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is a non-polar amino acid or a basic polar amino acid; and $X_2$ and $X_4$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a non-polar amino acid or a basic polar amino acid; and $X_2$ and $X_4$ represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser; and $X_5$ is a non-polar amino acid or a basic or acidic polar amino acid.

In one embodiment of the first aspect of the invention, optionally in combination with any one of the embodiments provided above or below, when $R_1$ and $R_2$ form a —C(=O)— linker, $R_2'$ is hydrogen; $X_1$, $X_3$, and $X_5$ represent the same non-polar amino acid with the same configuration; $X_2$ is L-Phe; and $X_4$ is L-Lys; then $X_1$, $X_3$ and $X_5$ are selected from the group consisting of: Gly, Val, Leu, Ile, Pro, Phe, Trp and Met (either with L- or D-configuration).

In another embodiment of the first aspect of the invention, optionally in combination with any one of the embodiments provided above or below, the peptide is one wherein three of $X_1$ to $X_5$ are non-conservative amino acid residues as defined above.

In another embodiment of the first aspect of the invention, optionally in combination with any one of the embodiments provided above or below, the peptide is one wherein:

$R_1$ and $R_2$ form a birradical linker as defined above;

three of $X_1$ to $X_5$ are non-conservative amino acid residues as defined above; and the remaining X's radicals represent any amino acid; or, alternatively, $R_1$ is hydrogen;

one of $R_2$ and $R_2'$ is hydrogen and the other is —C(=O)NR$_3$R$_4$;

$R_3$ and $R_4$ are as defined in the first aspect of the invention;

three of $X_1$ to $X_5$ are non-conservative amino acid residues as defined above; and the remaining X's radicals represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

three of $X_1$ to $X_5$ are non-conservative amino acid residues as defined above; and the remaining X's radicals represent any amino acid; or, alternatively, $R_1$ is hydrogen;

one of $R_2$ and $R_2'$ is hydrogen and the other is —C(=O)OH;

three of $X_1$ to $X_5$ are non-conservative amino acid residues as defined above; and the remaining X's radicals represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

three of $X_1$ to $X_5$ are non-conservative amino acid residues as defined above; and the remaining X's radicals represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above; and three of $X_1$ to $X_5$ are non-conservative amino acid residues as defined above.

In another embodiment of the first aspect of the invention, optionally in combination with any one of the embodiments provided above or below, $X_1$ is an amino acid which is non-conservative with respect to L-Asp; $X_3$ is an amino acid which is non-conservative with respect to L-Ser; and $X_5$ is an amino acid which is non-conservative with respect to L-Pro.

In another embodiment of the first aspect of the invention, optionally in combination with any one of the embodiments provided above or below, wherein:

$R_1$ and $R_2$ form a birradical linker as defined above;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid; or, alternatively $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent any amino acid.

In another embodiment of the first aspect of the invention, optionally in combination with any one of the embodiments provided above or below, wherein:

$R_1$ and $R_2$ form a birradical linker as defined above;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively; or, alternatively $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl;

one of $R_2$ and $R_2'$ is hydrogen and the other is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser;

$X_5$ is an amino acid which is non-conservative with respect to L-Pro; and $X_2$ and $X_4$ represent conservative amino acids with respect to L-Phe and L-Lys, respectively.

In another embodiment of the first aspect of the invention, optionally in combination with any one of the embodiments provided above or below, $X_1$ is an amino acid which is non-conservative with respect to L-Asp; $X_3$ is an amino acid which is non-conservative with respect to L-Ser; and $X_5$ is a nonpolar amino acid.

In another embodiment of the first aspect of the invention, optionally in combination with any one of the embodiments provided above or below, wherein:

$R_1$ and $R_2$ form a birradical linker as defined above;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid; or, alternatively, $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid; or, alternatively, $R_1$ is —C(=O)—CH$_2$—NH—C(=O)—(C$_1$-C$_5$)alkyl;

one of $R_2$ and $R_2'$ is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent any amino acid.

In another embodiment of the first aspect of the invention, optionally in combination with any one of the embodiments provided above or below, wherein:

$R_1$ and $R_2$ form a birradical linker as defined above;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O)NR$_3$R$_4$, wherein $R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl or —C(=O)—(C$_1$-C$_{20}$)alkyl;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O)OH;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl, or —C(=O)—(C$_1$-C$_{20}$)alkyl;

one of $R_2$ and $R_2'$ is hydrogen and the other is —C(=O)NR$_3$R$_4$;

$R_3$ and $R_4$ are as defined in the first aspect of the invention;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively; or, alternatively, $R_1$ is —C(=O)—CH$_2$—NH—C(=O)—(C$_1$-C$_5$)alkyl;

one of $R_2$ and $R_2'$ is —C(=O)NR$_3$R$_4$;

$R_3$ and $R_4$ are as defined above;

$X_1$ is an amino acid which is non-conservative with respect to L-Asp;

$X_3$ is an amino acid which is non-conservative with respect to L-Ser;

$X_5$ is a nonpolar amino acid; and $X_2$ and $X_4$ represent conservative amino acids with respect to L-Phe and L-Lys, respectively. In another embodiment of the first aspect of the invention, $R_1$ is hydrogen;

one of $R_2$ and $R_2'$ is hydrogen and the other is —C(=O)OH;

$X_1$ is selected from a non-polar amino acid, a polar neutral amino acid and a basic amino acid;

$X_3$ is an amino acid selected from an acid and a basic amino acid;

$X_5$ is a nonpolar amino acid; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O)OH;

$X_1$ is selected from a polar neutral amino acid and a basic amino acid;

$X_3$ is an amino acid selected from a non-polar, an acid and a basic amino acid;

$X_5$ is a nonpolar amino acid; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O)OH;

$X_1$ is selected from Gly, Ala, Val, Leu, Ile, Phe, Pro, Trp, Met (either with L- or D-configuration), a polar neutral amino acid and a basic amino acid;

$X_3$ is an amino acid selected from Gly, Val, Leu, Ile, Phe, Pro, Trp, Met (either with L- or D-configuration), an acid and a basic amino acid;

$X_5$ is a nonpolar amino acid; and $X_2$ and $X_4$ represent conservative amino acids with respect to L-Phe and L-Lys, respectively; or, alternatively, $R_1$ is hydrogen;

one of $R_2$ and $R_2'$ is hydrogen and the other is —C(=O) OH;

$X_1$ is selected from Gly, Val, Leu, Ile, Phe, Pro, Trp, Met (either with L- or D-configuration), a polar neutral amino acid and a basic amino acid;

$X_3$ is an amino acid selected from Gly, Ala, Val, Leu, Ile, Phe, Pro, Trp, Met (either with L- or D-configuration), an acid and a basic amino acid;

$X_5$ is a nonpolar amino acid; and $X_2$ and $X_4$ represent conservative amino acids with respect to L-Phe and L-Lys, respectively.

In another embodiment of the first aspect of the invention, optionally in combination with any one of the embodiments provided above or below, at least one of $X_1$ to $X_5$ is a D-amino acid residue.

In another embodiment of the first aspect of the invention, optionally in combination with any one of the embodiments provided above or below, the linker birradical is selected from the group consisting of: C(=O), $(C_1$-$C_{10})$alkyl-$NR_5$—C(=O), $(C_2$-$C_{10})$alkenyl-$NR_6$—C(=O), $(C_2$-$C_{10})$alkynyl-$NR_7$—C(=O), $(C_1$-$C_{10})$alkyl-$NR_8$—C(=O)—$(C_1$-$C_{10})$alkyl-$NR_9$—C(=O), $(C_1$-$C_{10})$alkyl-C(=O)—$(C_1$-$C_{10})$alkyl $NR_{10}$—C(=O), $(C_1$-$C_{10})$alkyl-C(=O)—$NR_{12}$—$(C_1$-$C_{10})$alkyl-$NR_{13}$—C(=O), $(C_1$-$C_{10})$alkyl-O—$(C_1$-$C_{10})$alkyl-$NR_{11}$—C(=O), $(C_1$-$C_{10})$alkyl-$NR_{14}R_{15}$—$(C_1$-$C_{10})$alkyl-$NR_{16}$—C(=O), $(C_1$-$C_{10})$alkyl-C(=O)—O—$(C_1$-$C_{10})$alkyl-$NR_{17}$—C(=O), $(C_1$-$C_{10})$alkyl-O—C(=O)—$(C_1$-$C_{10})$alkyl-$NR_{18}$—C(=O), being $R_5$ to $R_{18}$ as defined above.

In another embodiment of the first aspect of the invention, optionally in combination with any one of the embodiments provided above or below, the linker birradical is selected from the group consisting of C(=O), $(C_1$-$C_5)$alkyl-$NR_5$—C(=O), $(C_2$-$C_5)$alkenyl-$NR_6$—C(=O), $(C_2$-$C_5)$alkynyl-$NR_7$—C(=O), $(C_1$-$C_5)$alkyl-$NR_8$—C(=O)—$(C_1$-$C_5)$alkyl-$NR_9$—C(=O), $(C_1$-$C_5)$alkyl-C(=O)—$(C_1$-$C_5)$alkyl $NR_{10}$—C(=O), $(C_1$-$C_5)$alkyl-C(=O)—$NR_{12}$—$(C_1$-$C_5)$alkyl-$NR_{13}$—C(=O), $(C_1$-$C_5)$alkyl-O—$(C_1$-$C_5)$alkyl-$NR_{11}$—C(=O), $(C_1$-$C_5)$alkyl-$NR_{14}R_{15}$—$(C_1$-$C_5)$alkyl-$NR_{16}$—C(=O), $(C_1$-$C_5)$alkyl-C(=O)—O—$(C_1$-$C_5)$alkyl-$NR_{17}$—C(=O), $(C_1$-$C_5)$alkyl-O—C(=O)—$(C_1$-$C_5)$alkyl-$NR_{18}$—C(=O), being $R_5$ to $R_{18}$ as defined above.

In another embodiment of the first aspect of the invention, $R_5$ to $R_{22}$ represent hydrogen.

In another embodiment of the first aspect of the invention, optionally in combination with any one of the embodiments provided above or below, the linker birradical is selected from the group consisting of: C(=O), $(C_1$-$C_{10})$alkyl-NH—C(=O), $(C_2$-$C_{10})$alkenyl-NH—C(=O), $(C_2$-$C_{10})$alkynyl-NH—C(=O), $(C_1$-$C_{10})$alkyl-NH—C(=O)—$(C_1$-$C_{10})$alkyl-NH—C(=O), $(C_1$-$C_{10})$alkyl-O—$(C_1$-$C_{10})$alkyl-NH—C(=O), $(C_1$-$C_5)$alkyl-NH—C(=O), $(C_2$-$C_5)$alkenyl-NH—C(=O), $(C_2$-$C_5)$alkynyl-NH—C(=O), $(C_1$-$C_5)$alkyl-NH—C(=O)—$(C_1$-$C_5)$alkyl-NH—C(=O), $(C_1$-$C_5)$alkyl-O—$(C_1$-$C_5)$alkyl-NH—C(=O), $(C_1$-$C_5)$alkyl-NH—C(=O), $(C_1$-$C_{10})$alkyl-N(CH$_3$)—C(=O), $(C_2$-$C_{10})$alkenyl-N(CH$_3$)—C(=O), $(C_2$-$C_{10})$alkynyl-N(CH$_3$)—C(=O), $(C_1$-$C_{10})$alkyl-N(CH$_3$)—C(=O)—$(C_1$-$C_{10})$alkyl-N(CH$_3$)—C(=O), $(C_1$-$C_{10})$alkyl-O—$(C_1$-$C_{10})$alkyl-N(CH$_3$)—C(=O), $(C_1$-$C_5)$alkyl-N(CH$_3$)—C(=O), $(C_2$-$C_5)$alkenyl-N(CH$_3$)—C(=O), $(C_2$-$C_5)$alkynyl-N(CH$_3$)—C(=O), $(C_1$-$C_5)$alkyl-N(CH$_3$)—C(=O)—$(C_1$-$C_5)$alkyl-N(CH$_3$)—C(=O), and $(C_1$-$C_5)$alkyl-O—$(C_1$-$C_5)$alkyl-N(CH$_3$)—C(=O).

In another embodiment of the first aspect of the invention, optionally in combination with any one of the embodiments provided above or below, the linker birradical is selected from the group consisting of: —C(=O)—, —(CH$_2$)$_3$—NH—CO—, —(CH$_2$)$_2$—NH—C(=O)—(CH$_2$)—NH—C(=O)—, and —(CH$_2$)$_2$—O—(CH$_2$)$_2$—NH—C(=O)—.

In a particular embodiment of the first aspect of the invention, optionally in combination with any one of the embodiments provided above or below, $R_1$ is —C(=O)—CH$_2$—NH—C(=O)—CH$_3$.

In another embodiment of the first aspect of the invention, optionally in combination with any one of the embodiments provided above or below, one of $R_3$ and $R_4$ is hydrogen and the other is $(C_1$-$C_{10})$alkyl. In another embodiment of the invention, optionally in combination with any one of the embodiments provided above or below, $R_3$ and $R_4$ are the same or different and represent hydrogen. In another embodiment of the invention, optionally in combination with any one of the embodiments provided above or below, $R_3$ and $R_4$ are the same or different and represent $(C_1$-$C_{10})$alkyl. In another embodiment of the first aspect of the invention, optionally in combination with any one of the embodiments provided above or below, $R_3$ is hydrogen and $R_4$ is $(C_1$-$C_5)$alkyl. In another embodiment of the first aspect of the invention, optionally in combination with any one of the embodiments provided above or below, $R_3$ and $R_4$ are the same $(C_1$-$C_{10})$alkyl. In another embodiment of the first aspect of the invention, optionally in combination with any one of the embodiments provided above or below, $R_3$ and $R_4$ are the same $(C_1$-$C_5)$alkyl. In another embodiment of the first aspect of the invention, optionally in combination with any one of the embodiments provided above or below, $R_3$ is hydrogen an $R_4$ is —CH$_3$. In another embodiment of the first aspect of the invention, optionally in combination with any one of the embodiments provided above or below, $R_3$ and $R_4$ are the same and represent —CH$_3$.

In an embodiment of the peptide of the first aspect of the invention, "substituted $(C_1$-$C_{10})$alkyl" means that the $(C_1$-$C_{10})$alkyl is substituted by one or two radicals, the same or different, selected from halogen, $(C_1$-$C_5)$alkyl, and a $(C_3$-$C_6)$cycloakyl radical.

In another embodiment of the peptide of the first aspect of the invention, "substituted $(C_2$-$C_{10})$alkenyl" means that the $(C_2$-$C_{10})$alkenyl is substituted by one or two radicals selected from the group consisting of: halogen, $(C_1$-$C_5)$alkyl, and a $(C_3$-$C_6)$cycloakyl.

In a last embodiment of the peptide of the first aspect of the invention, "substituted $(C_2$-$C_{10})$alkynyl" means that the $(C_2$-$C_{10})$alkynyl is substituted by one or two radicals selected from the group consisting of: halogen, $(C_1$-$C_5)$alkyl, and a $(C_3$-$C_6)$cycloakyl.

In an embodiment of the first aspect of the invention, the peptide is selected from the group consisting of SEQ ID NO: 2 to SEQ ID NO: 54:

TABLE 3

| SEQ. ID.NO. | Sequence | Features |
|---|---|---|
| 1 | RDFQSFRKMWPFFAM | |
| 2 | RDFQSFRKMWPFFAM | Acetylated; Amidated |
| 3 | RDFQSFRKMWPFFAM | D-Asp2 |
| 4 | RDFQSFRKMWPFFAM | Acetylated; Amidated; D-Asp2 |
| 5 | RAFQSFRKMWPFFAM | |
| 6 | RAFQSFRKMWPFFAM | D-Ala2 |
| 7 | RSFQSFRKMWPFFAM | |
| 8 | RYFQSFRKMWPFFAM | |
| 9 | RWFQSFRKMWPFFAM | |
| 10 | REFQSFRKMWPFFAM | |
| 11 | RNFQSFRKMWPFFAM | |
| 12 | RKFQSFRKMWPFFAM | |
| 13 | RAFQSFRKMWPFFAM | Acetylated; Amidated |
| 14 | RAFQSFRKMWPFFAM | Acetylated; Amidated; D-Ala2 |
| 15 | RDAQSFRKMWPFFAM | |
| 16 | RDWQSFRKMWPFFAM | |
| 17 | RDYQSFRKMWPFFAM | |
| 18 | RDLQSFRKMWPFFAM | |
| 19 | RDFQAFRKMWPFFAM | |
| 20 | RDFQRFRKMWPFFAM | |
| 21 | RDFQNFRKMWPFFAM | |
| 22 | RDFQWFRKMWPFFAM | |
| 23 | RDFQEFRKMWPFFAM | |
| 24 | RDFQYFRKMWPFFAM | |
| 25 | RDFQKFRKMWPFFAM | |
| 26 | RDFQSFRAMWPFFAM | |
| 27 | RDFQSFREMWPFFAM | |
| 28 | RDFQSFRHMWPFFAM | |
| 29 | RDFQSFRRMWPFFAM | |
| 30 | RDFQSFRKMWAFFAM | |
| 31 | RDFQSFRKMWRFFAM | |
| 32 | RDFQSFRKMWNFFAM | |
| 33 | RDFQSFRKMWVFFAM | |
| 34 | RDFQSFRKMWEFFAM | |
| 35 | RDFQSFRKMWYFFAM | |
| 36 | RDFQSFRKMWGFFAM | |
| 37 | RDFQSFRKMWKFFAM | |
| 38 | RDFQSFRKMWAFFAM | Acetylated; Amidated; D-Met15 |
| 39 | RDFQAFRKMWPFFAM | Acetylated; Amidated; D-Ala5 |
| 40 | RDFQSFRKMWAFFAM | Acetylated; Amidated; D-Ala11 |
| 41 | RAFQAFRKMWPFFAM | Acetylated; Amidated; |
| 42 | RAFQAFRKMWPFFAM | Lineal (non-acetylated, non-amidated) |
| 43 | RAFQAFRKMWPFFAM | Acetylated; Amidated; D-Ala2; D-Ala5 |
| 44 | RAFQSFRKMWAFFAM | Acetylated; Amidated |
| 45 | RAFQAFRKMWAFFAM | Acetylated; Amidated |
| 46 | RAFQSFRKMWPFFAM | D-Arg1 |
| 47 | RAFQSFRKMWPFFAM | D-Met15 |
| 48 | RAFQSFRKMWPFFAM | D-Arg1; D-Met15 |
| 49 | RDFQSFRKMWPFFAM | L is C(=O) |
| 50 | RAFQAFRKMWPFFAM | L is C(=O) |
| 51 | RAFQAFRKMWPFFAM | D-Ala2; L is C(=O) |
| 52 | RAFQAFRKMWPFFAM | D-Ala2; and L is —(CH$_2$)$_3$—NH—C(=O)— |
| 53 | RAFQAFRKMWPFFAM | D-Ala2; L is —(CH$_2$)$_2$—NH—C(=O)—(CH$_2$)—NH—C(=O)— |
| 54 | RAFQAFRKMWPFFAM | D-Ala2; L is —(CH$_2$)$_2$—O—(CH$_2$)$_2$—NH—C(=O)—, |

"Acetylated" means that R$_1$ means —C(=O) CH$_2$ NH C(=O) CH$_3$;
"Amidated" means that one of R$_2$ and R$_2$' is hydrogen and the other is C(=O)NH$_2$
"L" means the linker as defined in the present invention In another embodiment of the first aspect of the invention, the peptide is selected from the group consisting of: SEQ ID NO: 2, SEQ ID NO: 3, SEQ ID NO: 13, SEQ ID NO: 14, SEQ ID NO: 38, SEQ ID NO: 41, SEQ ID NO: 43 to SEQ ID NO: 45, and SEQ ID NO: 49 to SEQ ID NO: 54.

In another embodiment of the first aspect of the invention, the peptide is selected from the group consisting of: SEQ ID NO: 6 to 12, SEQ ID No: 15 to 37, SEQ ID NO: 46 and SEQ ID NO: 47.

In a twelfth aspect, the present invention provides a peptide of formula (I) as defined above, wherein X$_1$ represents a D-amino acid or, alternatively, X$_1$ is a non-conservative amino acid with respect to L-Asp, the non-conservative amino acid being selected from non-polar, neutral polar and basic polar amino acid residues. All the embodiments provided above regarding the meaning of $R_1$ to $R_{40}$ and $X_2$ to $X_5$ under the first aspect of the invention, are also embodiments of the peptide of twelfth aspect of the invention.

In an embodiment of the twelfth aspect of the invention, $X_1$ represents a non-conservative amino acid with respect to L-Asp; and $X_2$ to $X_5$ represent amino acid residues, the same or different.

In another embodiment of the twelfth aspect of the invention, optionally in combination with any one of the embodiments provided above or below, $X_1$ is an amino acid residue, either in L or D-configuration, selected from the group consisting of: Ala, Ser, Tyr, Trp, Asn and Lys.

In another embodiment of the twelfth aspect of the invention, optionally in combination with any one of the embodiments provided above or below, $X_2$ and $X_5$ represent non-polar amino acid residues, the same or different; $X_3$ represents a neutral polar amino acid residue; and $X_4$ represents a basic amino acid residue. In another embodiment of the twelfth aspect of the invention, optionally in combination with any one of the embodiments provided above or below, $X_2$ is L- or D-Phe, $X_3$ is L- or D-Ser, $X_4$ is L- or D-Lys, and $X_5$ is L- or D-Pro. In another embodiment of the twelfth aspect of the invention, optionally in combination with any one of the embodiments provided above or below, $X_2$ is L-Phe, $X_3$ is L-Ser, $X_4$ is L-Lys, and $X_5$ is L-Pro.

In another embodiment of the twelfth aspect of the invention, optionally in combination with any one of the embodiments provided above or below, $X_1$ is an amino acid residue, either in L or D-configuration, selected from the group consisting of: Ala, Ser, Tyr, Trp, Asn and Lys, $X_2$ and $X_5$ represent non-polar amino acid residues, the same or different; $X_3$ represents a neutral polar amino acid residue; and $X_4$ represents a basic amino acid residue. In another embodiment of the twelfth aspect of the invention, optionally in combination with any one of the embodiments provided above or below, $X_1$ is an amino acid residue, either in L or D-configuration, selected from the group consisting of: Ala, Ser, Tyr, Trp, Asn and Lys, $X_2$ is L- or D-Phe, $X_3$ is L- or D-Ser, $X_4$ is L- or D-Lys, and $X_5$ is L- or D-Pro. In another embodiment of the twelfth aspect of the invention, optionally in combination with any one of the embodiments provided above or below, $X_1$ is an amino acid residue, either in L or D-configuration, selected from the group consisting of: Ala, Ser, Tyr, Trp, Asn and Lys, $X_2$ is L-Phe, $X_3$ is L-Ser, $X_4$ is L-Lys, and $X_5$ is L-Pro.

In one embodiment of the twelfth aspect of the invention, optionally in combination with any one of the embodiments provided above or below, $R_1$ is hydrogen, one of $R_2$ and $R'_2$ is hydrogen and the other is —C(=O)OH. In another embodiment of the twelfth aspect of the invention, optionally in combination with any one of the embodiments provided above or below, when $R_1$ is H; one of $R_2$ and $R_2'$ is hydrogen and the other is —C(=O)H; $X_2$ represents L-Phe; $X_3$ represents L-Ser, $X_4$ represents L-Lys; $X_5$ represents L-Pro; and $X_1$ represents a non-polar amino acid, then $X_1$ is selected from: Gly, Val, Leu, Ile, Pro, Phe, Trp, and Met (either with D- or L-configuration).

In another embodiment of the twelfth aspect of the invention, optionally in combination with any one of the embodiments provided above or below, $R_1$ is C(=O)—CH$_2$—NH—C(=O)—(C$_1$-C$_5$)alkyl, one of $R_2$ and $R'_2$ is hydrogen and the other is —C(=O)NR$_3$R$_4$, wherein $R_3$ and $R_4$ are as defined in the first aspect of the invention or in any one of the embodiments of the first aspect of the invention.

In another embodiment of the twelfth aspect of the invention, optionally in combination with any one of the embodiments provided above or below, the amino acid residue at N(t) and/or the amino acid residue at C(t) has D-configuration.

In a last embodiment of the twelfth aspect of the invention, the peptide of formula (I) is selected from the group consisting of: SEQ ID NO: 5 to 9, 11 to 14, and 46 to 48.

In a thirteenth aspect, the present invention provides a peptide of formula (I) as defined in the first aspect of the invention, wherein $X_2$ represents a D-amino acid or, alternatively, $X_2$ represents a non-conservative amino acid with respect to L-Phe, the non-conservative amino acid being selected from a neutral polar amino acid, an acidic polar amino acid and a basic polar amino acid. All the embodiments provided above regarding the meaning of $R_1$ to $R_{40}$, $X_1$, and $X_3$ to $X_5$ under the first aspect of the invention, are also embodiments of the peptide of thirteenth aspect of the invention.

In an embodiment of the thirteenth aspect of the invention, $X_2$ represents a non-conservative amino acid with respect to L-Phe, and $X_1$, and $X_3$ to $X_5$ represent amino acid residues, the same or different.

In another embodiment of the thirteenth aspect of the invention, optionally in combination with any one of the embodiments provided above or below, $X_2$ represents a neutral polar amino acid. In another embodiment of the thirteenth aspect of the invention, wherein $X_2$ is L- or D-Tyr.

In another embodiment of the thirteenth aspect of the invention, optionally in combination with any one of the embodiments provided above or below, $X_1$ represents an acidic amino acid residue, $X_3$ represents a neutral polar amino acid residue; $X_4$ represents a basic amino acid residue; and $X_5$ represents a non-polar amino acid residue.

In another embodiment of the thirteenth aspect of the invention, optionally in combination with any one of the embodiments provided above or below, $X_1$ represents an acidic amino acid residue, $X_2$ represents a neutral polar amino acid, $X_3$ represents a neutral polar amino acid residue; $X_4$ represents a basic amino acid residue; and $X_5$ represents a non-polar amino acid residue.

In another embodiment of the thirteenth aspect of the invention, optionally in combination with any one of the embodiments provided above or below, $X_1$ represents an acidic amino acid residue, $X_2$ represents L- or D-Tyr, $X_3$ represents a neutral polar amino acid residue; $X_4$ represents a basic amino acid residue; and $X_5$ represents a non-polar amino acid residue.

In another embodiment of the thirteenth aspect of the invention, optionally in combination with any one of the embodiments provided above or below, $X_1$ is L- or D-Asp; $X_2$ represents a neutral polar amino acid; $X_3$ is L- or D-Ser, $X_4$ is L- or D-Lys, and $X_5$ is L- or D-Pro.

In another embodiment of the thirteenth aspect of the invention, optionally in combination with any one of the embodiments provided above or below, $X_1$ is L- or D-Asp; $X_2$ represents L- or D-Tyr; $X_3$ is L- or D-Ser, $X_4$ is L- or D-Lys, and $X_5$ is L- or D-Pro.

In another embodiment of the thirteenth aspect of the invention, optionally in combination with any one of the embodiments provided above or below, $X_1$ is L-Asp; $X_3$ is L-Ser; $X_4$ is L-Lys, and $X_5$ is L-Pro.

In another embodiment of the thirteenth aspect of the invention, optionally in combination with any one of the embodiments provided above or below, $X_1$ is L-Asp; $X_2$ represents a neutral polar amino acid; $X_3$ is L-Ser; $X_4$ is L-Lys, and $X_5$ is L-Pro.

In another embodiment of the thirteenth aspect of the invention, optionally in combination with any one of the embodiments provided above or below, $X_1$ is L-Asp; $X_2$ represents L- or D-Tyr; $X_3$ is L-Ser; $X_4$ is L-Lys, and $X_5$ is L-Pro.

In another embodiment of the thirteenth aspect of the invention, optionally in combination with any one of the embodiments provided above or below, $R_1$ is hydrogen, one of $R_2$ and $R'_2$ is hydrogen and the other is —C(=O)OH.

In another embodiment of the thirteenth aspect of the invention, optionally in combination with any one of the embodiments provided above or below, the amino acid residue at N(t) and/or the amino acid residue at C(t) has D-configuration.

In another embodiment of the thirteenth aspect of the invention, optionally in combination with any one of the embodiments provided above, the peptide of formula (I) which is SEQ ID NO: 17.

In a fourteenth aspect, the present invention provides a peptide wherein $X_3$ represents a D-amino acid or, alternatively, $X_3$ represents a non-conservative amino acid with respect to L-Ser which is selected from non-polar, acidic polar and basic polar amino acid residues. All the embodiments provided above regarding the meaning of $R_1$ to $R_{40}$, $X_1$, $X_2$, $X_4$, and $X_5$ under the first aspect of the invention, are also embodiments of the peptide of fourteenth aspect of the invention.

In an embodiment of the fourteenth aspect of the invention, optionally in combination with any one of the embodiments provided above or below, $X_3$ represents a non-conservative amino acid with respect to L-Ser; and $X_1$, $X_2$, $X_4$, and $X_5$ represent amino acid residues, the same or different.

In an embodiment of the fourteenth aspect of the invention, optionally in combination with any one of the embodiments provided above or below, $X_3$ represents a non-conservative amino acid with respect to L-Ser selected from a non-polar amino acid and a basic polar amino acid;

In an embodiment of the fourteenth aspect of the invention, optionally in combination with any one of the embodiments provided above or below, $X_3$ is an amino acid residue, either in L or D-configuration, selected from the group consisting of: Ala, Arg, Trp, Glu, and Lys.

In an embodiment of the fourteenth aspect of the invention, optionally in combination with any one of the embodiments provided above or below, $X_1$ represents an acidic amino acid residue, $X_2$ represents a non-polar amino acid residue; $X_4$ represents a basic amino acid residue; and $X_5$ represents a non-polar amino acid residue.

In an embodiment of the fourteenth aspect of the invention, optionally in combination with any one of the embodiments provided above or below, $X_1$ represents an acidic amino acid residue, $X_2$ represents a non-polar amino acid residue, $X_3$ is selected from the group consisting of: Ala, Arg, Trp, Glu, and Lys, $X_4$ represents a basic amino acid residue, and $X_5$ represents a non-polar amino acid residue.

In an embodiment of the fourteenth aspect of the invention, optionally in combination with any one of the embodiments provided above or below, $X_1$ is L- or D-Asp; $X_2$ is L- or D-Phe; $X_4$ is L- or D-Lys; and $X_5$ is L- or D-Pro.

In an embodiment of the fourteenth aspect of the invention, optionally in combination with any one of the embodiments provided above or below, $X_1$ is L- or D-Asp; $X_2$ is L- or D-Phe; $X_3$ is selected from the group consisting of: Ala, Arg, Trp, Glu, and Lys; $X_4$ is L- or D-Lys; and $X_5$ is L- or D-Pro.

In an embodiment of the fourteenth aspect of the invention, optionally in combination with any one of the embodiments provided above or below, $X_1$ is L-Asp; $X_2$ is L-Phe; $X_3$ is selected from the group consisting of: Ala, Arg, Trp, Glu, and Lys; $X_4$ is L-Lys; and $X_5$ is L-Pro.

In an embodiment of the fourteenth aspect of the invention, optionally in combination with any one of the embodiments provided above or below, $R_1$ is hydrogen, one of $R_2$ and $R'_2$ is hydrogen and the other is —C(=O)OH.

In an embodiment of the fourteenth aspect of the invention, optionally in combination with any one of the embodiments provided above or below, $R_1$ is —C(=O)—CH$_2$—NH—C(=O)—(C$_1$-C$_5$)alkyl, one of $R_2$ and $R_2$' is hydrogen and the other is —C(=O)NR$_3$R$_4$, R$_3$ and R$_4$ being as defined above. In an embodiment of the fourteenth aspect of the invention, optionally in combination with any one of the embodiments provided above or below, $R_1$ is —C(=O)—CH$_2$—NH—C(=O)—CH$_3$.

In an embodiment of the fourteenth aspect of the invention, optionally in combination with any one of the embodiments provided above or below, the amino acid residue at N(t) and/or the amino acid residue at C(t) has D-configuration.

In a last embodiment of the fourteenth aspect of the invention, the peptide is one of sequence SEQ ID NO: 19 to 20, 22 to 23, 25, or 39.

In a fifteenth aspect the present invention provides a peptide of formula (I) wherein $X_4$ represents a D-amino acid or, alternatively, $X_4$ represents a L-basic polar amino acid. All the embodiments provided above regarding the meaning of $R_1$ to $R_{40}$ and $X_1$ to $X_3$ and $X_5$ under the first aspect of the invention, are also embodiments of the peptide of the fifteenth aspect of the invention.

In an embodiment of the fifteenth aspect of the invention, optionally in combination with any one of the embodiments provided above or below, wherein $X_4$ is selected from His and Arg, either in L- or D-configuration.

In an embodiment of the fifteenth aspect of the invention, optionally in combination with any one of the embodiments provided above or below, $X_4$ is L-His or L-Arg.

In an embodiment of the fifteenth aspect of the invention, optionally in combination with any one of the embodiments provided above or below, $X_1$ represents an acidic amino acid residue, $X_2$ represents a non-polar amino acid residue, $X_3$ represents a neutral polar amino acid residue, and $X_5$ represents a non-polar amino acid residue.

In an embodiment of the fifteenth aspect of the invention, optionally in combination with any one of the embodiments provided above or below, $X_1$ represents an acidic amino acid residue, $X_2$ represents a non-polar amino acid residue, $X_3$ represents a neutral polar amino acid residue, $X_4$ is selected from His and Arg, either in L- or D-configuration, and $X_5$ represents a non-polar amino acid residue.

In an embodiment of the fifteenth aspect of the invention, optionally in combination with any one of the embodiments provided above or below, $X_1$ represents an acidic amino acid residue, $X_2$ represents a non-polar amino acid residue, $X_3$ represents a neutral polar amino acid residue, $X_4$ is L-His or L-Arg, and $X_5$ represents a non-polar amino acid residue.

In an embodiment of the fifteenth aspect of the invention, optionally in combination with any one of the embodiments provided above or below, $X_1$ is L- or D-Asp; $X_2$ is L- or D-Phe; $X_3$ is L- or D-Ser; and $X_5$ is L- or D-Pro.

In an embodiment of the fifteenth aspect of the invention, optionally in combination with any one of the embodiments provided above or below, $X_1$ is L- or D-Asp; $X_2$ is L- or D-Phe; $X_3$ is L- or D-Ser; $X_4$ is selected from His and Arg, either in L- or D-configuration; and $X_5$ is L- or D-Pro.

In an embodiment of the fifteenth aspect of the invention, optionally in combination with any one of the embodiments provided above or below, $X_1$ is L- or D-Asp; $X_2$ is L- or D-Phe; $X_3$ is L- or D-Ser; $X_4$ is L-His or L-Arg; and $X_5$ is L- or D-Pro.

In an embodiment of the fifteenth aspect of the invention, optionally in combination with any one of the embodiments provided above or below, $X_1$ is L-Asp; $X_2$ is L-Phe; $X_3$ is L-Ser; and $X_5$ is L-Pro.

In an embodiment of the fifteenth aspect of the invention, optionally in combination with any one of the embodiments provided above or below, $X_1$ is L-Asp; $X_2$ is L-Phe; $X_3$ is L-Ser; $X_4$ is selected from His and Arg, either in L- or D-configuration; and $X_5$ is L-Pro.

In an embodiment of the fifteenth aspect of the invention, optionally in combination with any one of the embodiments provided above or below, $X_1$ is L-Asp; $X_2$ is L-Phe; $X_3$ is L-Ser; $X_4$ is L-His or L-Arg; and $X_5$ is L-Pro.

In an embodiment of the fifteenth aspect of the invention, optionally in combination with any one of the embodiments provided above or below, $R_1$ is hydrogen, one of $R_2$ and $R_2'$ is hydrogen and the other is —C(=O)OH.

In a last embodiment of the fifteenth aspect of the invention, optionally in combination with any one of the embodiments provided above or below, the peptide is one of sequence SEQ ID NO: 28 or 29.

In a sixteenth aspect the present invention provides a peptide of formula (I) wherein $X_5$ represents a D-amino acid or, alternatively, $X_5$ represents a non-conservative amino acid with respect to L-Pro which is selected from a neutral polar amino acid and a basic polar amino acid. All the embodiments provided above regarding the meaning of $R_1$ to $R_{40}$ and $X_1$ to $X_4$ under the first aspect of the invention, are also embodiments of the peptide of the sixteenth aspect of the invention.

In one embodiment of the sixteenth aspect of the invention, optionally in combination with any one of the embodiments provided above or below, $X_5$ represents a non-conservative amino acid with respect to L-Pro; and $X_1$ to $X_4$ represent amino acid residues, the same or different.

In another embodiment of the sixteenth aspect of the invention, optionally in combination with any one of the embodiments provided above or below, $X_5$ is a L- or D-basic amino acid.

In another embodiment of the sixteenth aspect of the invention, optionally in combination with any one of the embodiments provided above or below, $X_5$ is an amino acid residue, either in L- or D-configuration, selected from the group consisting of: Arg, Asn, Tyr, and Lys.

In another embodiment of the sixteenth aspect of the invention, optionally in combination with any one of the embodiments provided above or below, $X_1$ represents an acidic polar amino acid; $X_2$ represents a non-polar amino acid residue; $X_3$ represents a neutral polar amino acid residue; and $X_4$ represents a basic amino acid residue.

In another embodiment of the sixteenth aspect of the invention, optionally in combination with any one of the embodiments provided above or below, $X_1$ represents an acidic polar amino acid; $X_2$ represents a non-polar amino acid residue; $X_3$ represents a neutral polar amino acid residue; $X_4$ represents a basic amino acid residue; and $X_5$ is a L- or D-basic amino acid.

In another embodiment of the sixteenth aspect of the invention, optionally in combination with any one of the embodiments provided above or below, $X_1$ represents an acidic polar amino acid; $X_2$ represents a non-polar amino acid residue; $X_3$ represents a neutral polar amino acid residue; $X_4$ represents a basic amino acid residue; and $X_5$ is an amino acid residue, either in L- or D-configuration, selected from the group consisting of: Arg, Asn, Tyr, and Lys.

In another embodiment of the sixteenth aspect of the invention, optionally in combination with any one of the embodiments provided above or below, $X_1$ is L- or D-Asp, $X_2$ is L- or D-Phe, $X_3$ is L- or D-Ser, and $X_4$ is L- or D-Lys.

In another embodiment of the sixteenth aspect of the invention, optionally in combination with any one of the embodiments provided above or below, $X_1$ is L- or D-Asp, $X_2$ is L- or D-Phe, $X_3$ is L- or D-Ser, $X_4$ is L- or D-Lys; and $X_5$ is a L- or D-basic amino acid.

In another embodiment of the sixteenth aspect of the invention, optionally in combination with any one of the embodiments provided above or below, $X_1$ is L- or D-Asp, $X_2$ is L- or D-Phe, $X_3$ is L- or D-Ser, $X_4$ is L- or D-Lys; and $X_5$ is an amino acid residue, either in L- or D-configuration, selected from the group consisting of: Arg, Asn, Tyr, and Lys.

In another embodiment of the sixteenth aspect of the invention, optionally in combination with any one of the embodiments provided above or below, $X_1$ is L-Asp, $X_2$ is L-Phe, $X_3$ is L-Ser, and $X_4$ is L-Lys.

In another embodiment of the sixteenth aspect of the invention, optionally in combination with any one of the embodiments provided above or below, $X_1$ is L-Asp, $X_2$ is L-Phe, $X_3$ is L-Ser, $X_4$ is L-Lys; and $X_5$ is a L- or D-basic amino acid.

In another embodiment of the sixteenth aspect of the invention, optionally in combination with any one of the embodiments provided above or below, $X_1$ is L-Asp, $X_2$ is L-Phe, $X_3$ is L-Ser, $X_4$ is L-Lys; and $X_5$ is an amino acid residue, either in L- or D-configuration, selected from the group consisting of: Arg, Asn, Tyr, and Lys.

In another embodiment of the sixteenth aspect of the invention, optionally in combination with any one of the embodiments provided above or below, $R_1$ and $R_2$ are hydrogen, and $R_2'$ is —C(=O)OH.

In another embodiment of the sixteenth aspect of the invention, optionally in combination with any one of the embodiments provided above or below, $R_1$ is —C(=O)—CH$_2$—NH—C(=O)—(C$_1$-C$_5$)alkyl, one of $R_2$ and $R_2'$ is hydrogen and the other is —C(=O)NR$_3$R$_4$, and $R_3$ and $R_4$ are as defined above.

In another embodiment of the sixteenth aspect of the invention, optionally in combination with any one of the embodiments provided above or below, $R_1$ is —C(=O)—CH$_2$—NH—C(=O)—CH$_3$, one of $R_2$ and $R_2'$ is hydrogen and the other is —C(=O)NR$_3$R$_4$, and $R_3$ and $R_4$ are as defined above.

In another embodiment of the sixteenth aspect of the invention, optionally in combination with any one of the embodiments provided above or below, the amino acid residue at N(t) and/or the amino acid residue at C(t) has D-configuration.

In a last embodiment of the sixteenth aspect of the invention, the peptide is selected from the group consisting of SEQ ID NO: 31, 32, 34, 35, 37, and 38.

In a seventeenth aspect, the present invention provides a peptide of formula (I) as defined in the first aspect of the invention, wherein $X_1$ and $X_3$ are the same or different and represent a D- or L-non-polar amino acid. All the embodiments provided above regarding the meaning of $R_1$ to $R_{40}$, $X_2$ and $X_4$ to $X_5$ under the first aspect of the invention, are also embodiments of the peptide of seventeenth aspect of the invention.

In one embodiment of the seventeenth aspect of the invention, wherein $X_1$ and $X_3$ are L-Ala or D-Ala.

In another embodiment of the seventeenth aspect of the invention, optionally in combination with any one of the embodiments provided above or below, when $R_1$ is H; one of $R_2$ and $R_2'$ is hydrogen and the other is —C(=O)OH; $X_2$ represents L-Phe; $X_4$ represents L-Lys; $X_5$ represents L-Pro; and both $X_1$ and $X_3$ represent the same non-polar amino acid with the same configuration, then $X_1$ and $X_3$ are selected from the group consisting of: D- or L-Gly, D- or L-Val, D- or L-Leu, D- or L-Ile, D- or L-Phe, D- or L-Pro, D- or L-Trp, D- and L-Met.

In one embodiment of the seventeenth aspect of the invention, optionally in combination with any one of the embodiments provided above or below, $R_1$ and $R_2$ form a linker birradical as defined above.

In one embodiment of the seventeenth aspect of the invention, optionally in combination with any one of the embodiments provided above or below $R_1$ is hydrogen, and one of $R_2$ and $R_2'$ is hydrogen and the other is —COOH.

In one embodiment of the seventeenth aspect of the invention, optionally in combination with any one of the embodiments provided above or below, $R_1$ is —C(=O)—CH$_2$—NH—C(=O)—(C$_1$-C$_5$)alkyl; one of $R_2$ and $R_2'$ is hydrogen and the other is —C(=O)NR$_3$R$_4$; and $R_3$ and $R_4$ being as defined in the first aspect of the invention.

In one embodiment of the seventeenth aspect of the invention, optionally in combination with any one of the embodiments provided above or below, wherein one or more of the non-conservative amino acids are D-amino acid(s).

In an embodiment of the seventeenth aspect of the invention, optionally in combination with any one of the embodiments provided above or below, $X_2$ represents a non-polar amino acid residue; $X_4$ represents a basic amino acid residue; and $X_5$ represents a non-polar amino acid residue.

In an embodiment of the seventeenth aspect of the invention, optionally in combination with any one of the embodiments provided above or below, $X_1$ and $X_3$ represent L- or D-Ala; $X_2$ represents a non-polar amino acid residue; $X_4$ represents a basic amino acid residue; and $X_5$ represents a non-polar amino acid residue.

In an embodiment of the seventeenth aspect of the invention, optionally in combination with any one of the embodiments provided above or below, $X_2$ is L- or D-Phe, $X_4$ is L- or D-Lys, and $X_5$ is L- or D-Pro.

In an embodiment of the seventeenth aspect of the invention, optionally in combination with any one of the embodiments provided above or below, $X_1$ and $X_3$ represent L- or D-Ala, $X_2$ is L- or D-Phe, $X_4$ is L- or D-Lys, and $X_5$ is L- or D-Pro.

In an embodiment of the seventeenth aspect of the invention, optionally in combination with any one of the embodiments provided above or below, $X_2$ is L-Phe, $X_4$ is L-Lys, and $X_5$ is L-Pro.

In an embodiment of the seventeenth aspect of the invention, optionally in combination with any one of the embodiments provided above or below, $X_1$ and $X_3$ represent L- or D-Ala, $X_2$ is L-Phe, $X_4$ is L-Lys, and $X_5$ is L-Pro.

In an eighteenth aspect, the present invention provides a peptide of formula (I) as defined in the first aspect of the invention, wherein $X_1$ represents a non-conservative amino acid with respect to L-Asp, and $X_5$ represents a non-polar amino acid residue. All the embodiments provided above regarding the meaning of $R_1$ to $R_{40}$ and $X_2$ to $X_4$ under the first aspect of the invention, are also embodiments of the peptide of eighteenth aspect of the invention.

In an embodiment of the eighteenth aspect of the invention, optionally in combination with any one of the embodiments provided above or below, $X_1$ and $X_5$ are the same or different and represent a D- or L-non-polar amino acid.

In an embodiment of the eighteenth aspect of the invention, optionally in combination with any one of the embodiments provided above or below, $X_1$ and $X_5$ represent D- or L-Ala.

In an embodiment of the eighteenth aspect of the invention, optionally in combination with any one of the embodiments provided above or below, $X_1$ and $X_5$ represent D-Ala.

In an embodiment of the eighteenth aspect of the invention, optionally in combination with any one of the embodiments provided above or below, $X_2$ represents a non-polar amino acid residue; $X_3$ represents a neutral polar amino acid residue; and $X_4$ represents a basic amino acid residue.

In an embodiment of the eighteenth aspect of the invention, optionally in combination with any one of the embodiments provided above or below, $X_1$ and $X_5$ represent the same or different and represent a D- or L-non-polar amino acid, $X_2$ represents a non-polar amino acid residue; $X_3$ represents a neutral polar amino acid residue; and $X_4$ represents a basic amino acid residue.

In an embodiment of the eighteenth aspect of the invention, optionally in combination with any one of the embodiments provided above or below, $X_1$ and $X_5$ represent D- or L-Ala, $X_2$ represents a non-polar amino acid residue; $X_3$ represents a neutral polar amino acid residue; and $X_4$ represents a basic amino acid residue.

In an embodiment of the eighteenth aspect of the invention, optionally in combination with any one of the embodiments provided above or below, $X_1$ and $X_5$ represent D-Ala, $X_2$ represents a non-polar amino acid residue; $X_3$ represents a neutral polar amino acid residue; and $X_4$ represents a basic amino acid residue.

In an embodiment of the eighteenth aspect of the invention, optionally in combination with any one of the embodiments provided above or below, $X_2$ is L- or D-Phe, $X_3$ is L- or D-Ser, and $X_4$ is L- or D-Lys.

In an embodiment of the eighteenth aspect of the invention, optionally in combination with any one of the embodiments provided above or below, $X_1$ and $X_5$ are the same or different and represent a D- or L-non-polar amino acid, $X_2$ is L- or D-Phe, $X_3$ is L- or D-Ser, and $X_4$ is L- or D-Lys.

In an embodiment of the eighteenth aspect of the invention, optionally in combination with any one of the embodiments provided above or below, $X_1$ and $X_5$ represent D- or L-Ala, $X_2$ is L- or D-Phe, $X_3$ is L- or D-Ser, and $X_4$ is L- or D-Lys.

In an embodiment of the eighteenth aspect of the invention, optionally in combination with any one of the embodiments provided above or below, $X_1$ and $X_5$ represent D-Ala, $X_2$ is L- or D-Phe, $X_3$ is L- or D-Ser, and $X_4$ is L- or D-Lys.

In an embodiment of the eighteenth aspect of the invention, optionally in combination with any one of the embodiments provided above or below, $X_1$ and $X_5$ are the same or different and represent a D- or L-non-polar amino acid, $X_2$ is L-Phe, $X_3$ is L-Ser, and $X_4$ is L-Lys.

In an embodiment of the eighteenth aspect of the invention, optionally in combination with any one of the embodiments provided above or below, $X_1$ and $X_5$ represent D- or L-Ala, $X_2$ is L-Phe, $X_3$ is L-Ser, and $X_4$ is L-Lys.

In an embodiment of the eighteenth aspect of the invention, optionally in combination with any one of the embodiments provided above or below, $X_1$ and $X_5$ represent D-Ala, $X_2$ is L-Phe, $X_3$ is L-Ser, and $X_4$ is L-Lys.

In one embodiment of the eighteenth aspect of the invention, optionally in combination with any one of the embodiments provided above or below $R_1$ is hydrogen, and one of $R_2$ and $R_2'$ is hydrogen and the other is —COOH.

In one embodiment of the eighteenth aspect of the invention, optionally in combination with any one of the embodiments provided above or below, $R_1$ is —C(=O)—CH$_2$—NH—C(=O)—(C$_1$-C$_5$)alkyl; one of $R_2$ and $R_2'$ is hydrogen and the other is —C(=O)NR$_3$R$_4$; and $R_3$ and $R_4$ being as defined in the first aspect of the invention.

In a nineteenth aspect the present invention provides a peptide of formula (I) as defined in the first aspect of the invention, wherein two or more of $X_1$, $X_3$, and $X_5$ are non-conservative amino acids with respect to L-Asp, L-Ser, and L-Pro, respectively. All the embodiments provided above regarding the meaning of $R_1$ to $R_{40}$, $X_2$ and $X_4$ under the first aspect of the invention, are also embodiments of the peptide of nineteenth aspect of the invention.

In a twentieth aspect the present invention provides a peptide of formula (I) as defined in the first aspect of the invention, wherein $X_1$ and $X_3$ represent non-conservative amino acids with respect to L-Asp, and L-Ser respectively, and $X_5$ represents a non-polar amino acid residue. All the embodiments provided above regarding the meaning of $R_1$ to $R_4$ and $X_2$ and $X_4$ under the first aspect of the invention, are also embodiments of the peptide of twentieth aspect of the invention.

In an embodiment of the twentieth aspect of the invention, optionally in combination with any one of the embodiments provided above or below, $X_1$ and $X_3$ are the same or different and represent a D- or L-non-polar amino acid.

In an embodiment of the twentieth aspect of the invention, optionally in combination with any one of the embodiments provided above or below, wherein $X_1$, $X_3$, and $X_5$ are D-Ala.

In an embodiment of the twentieth aspect of the invention, optionally in combination with any one of the embodiments provided above or below, $X_2$ represents a non-polar amino acid residue; and $X_4$ represents a basic amino acid residue.

In an embodiment of the twentieth aspect of the invention, optionally in combination with any one of the embodiments provided above or below, $X_1$, $X_3$, and $X_5$ represent D-Ala, $X_2$ represents a non-polar amino acid residue; and $X_4$ represents a basic amino acid residue.

In an embodiment of the twentieth aspect of the invention, optionally in combination with any one of the embodiments provided above or below, $X_2$ is L- or D-Phe, and $X_4$ is L- or D-Lys.

In an embodiment of the twentieth aspect of the invention, optionally in combination with any one of the embodiments provided above or below, $X_1$, $X_3$, and $X_5$ represent D-Ala, $X_2$ is L- or D-Phe, and $X_4$ is L- or D-Lys.

In an embodiment of the twentieth aspect of the invention, optionally in combination with any one of the embodiments provided above or below, $X_2$ is L-Phe, and $X_4$ is L-Lys.

In an embodiment of the twentieth aspect of the invention, optionally in combination with any one of the embodiments provided above or below, $X_1$, $X_3$, and $X_5$ are D-Ala, $X_2$ is L-Phe, and $X_4$ is L-Lys.

In another embodiment of the peptide of formula (I) as defined in any one of the aspects seventeen to twentieth, $R_1$ and $R_2$ form a linker birradical as defined in the first aspect of the invention.

In another embodiment of the peptide of formula (I) as defined in any one of the aspects seventeen to twentieth, wherein $R_1$ is —C(=O)—CH$_2$—NH—C(=O)—(C$_1$-C$_5$) alkyl, one of $R_2$ and $R_2'$ is hydrogen and the other is —C(=O)NR$_3$R$_4$; wherein $R_3$ and $R_4$ are as defined above.

The peptide of formula (I) as defined in any one of the aspects seventeen to twentieth which is selected form the group consisting of SEQ ID NO: 41 to 45, and 50 to 54.

The peptides of the present invention can be prepared following routine protocols such as by solid phase synthesis, wherein successive steps of (a) deprotecting the amino acid to be bound, and (b) protected-amino acid coupling cycles are performed.

The protecting group can be a N-protecting group, C-protecting group or a side-chain protecting group. There are commercially available protecting groups belonging to all three categories.

Illustrative non-limitative examples of amino acid protecting groups are the N-protecting groups t-Boc (or Boc) and Fmoc. When t-Boc or Fmoc is used in the synthesis of a peptide, the main four steps are: (a) protecting group is removed from the trailing amino acids (commercially available) in a deprotection reaction; (b) deprotection reagents are washed away to provide a clean coupling environment, (c) protected amino acids dissolved in a solvent such as dimethylformamide (DMF) combined with coupling reagents are pumped through the synthesis column, and (d) coupling reagents are washed away to provide clean deprotection environment. Depending on the particular N-protecting group, the deprotection reagent and the coupling reagent is one or another. The skilled person in the art, based on his general knowledge, and by routine methods, can optimize the particular conditions, if necessary.

In the particular case that the peptide of formula (I) is one of formula (Ia)

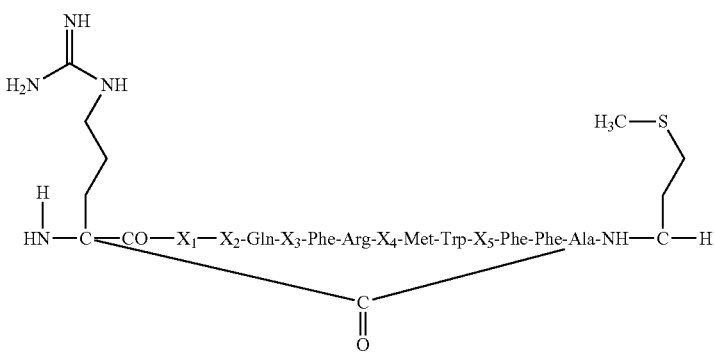

(Ia)

the process comprises, in a first stage, the synthesis of the peptide sequence for example by solid phase synthesis and, in a second stage, a cyclization reaction between the free amino and carboxy terminal groups of the peptide resulting from the synthesis. The conditions and reagents to be used in the cyclization step can be routinely determined.

In another particular case, when the peptide of formula (I) is one wherein $R_1$ and $R_2$ form a birradical which comprises an amide, ester, ketone, or ether, the process for preparing the peptide comprises a step of reacting: an amine with a carboxylic group (in case of the amide), a carboxylic acid with and alcohol (in case of an ester), by oxidation of a secondary alcohol (in case of a ketone) or by dehydration of an alcohol (in case of an ether). This kind of reactions is well-known in the state of the art and the skilled person can prepare the peptides with these linkers using routine methods.

Figure 4:
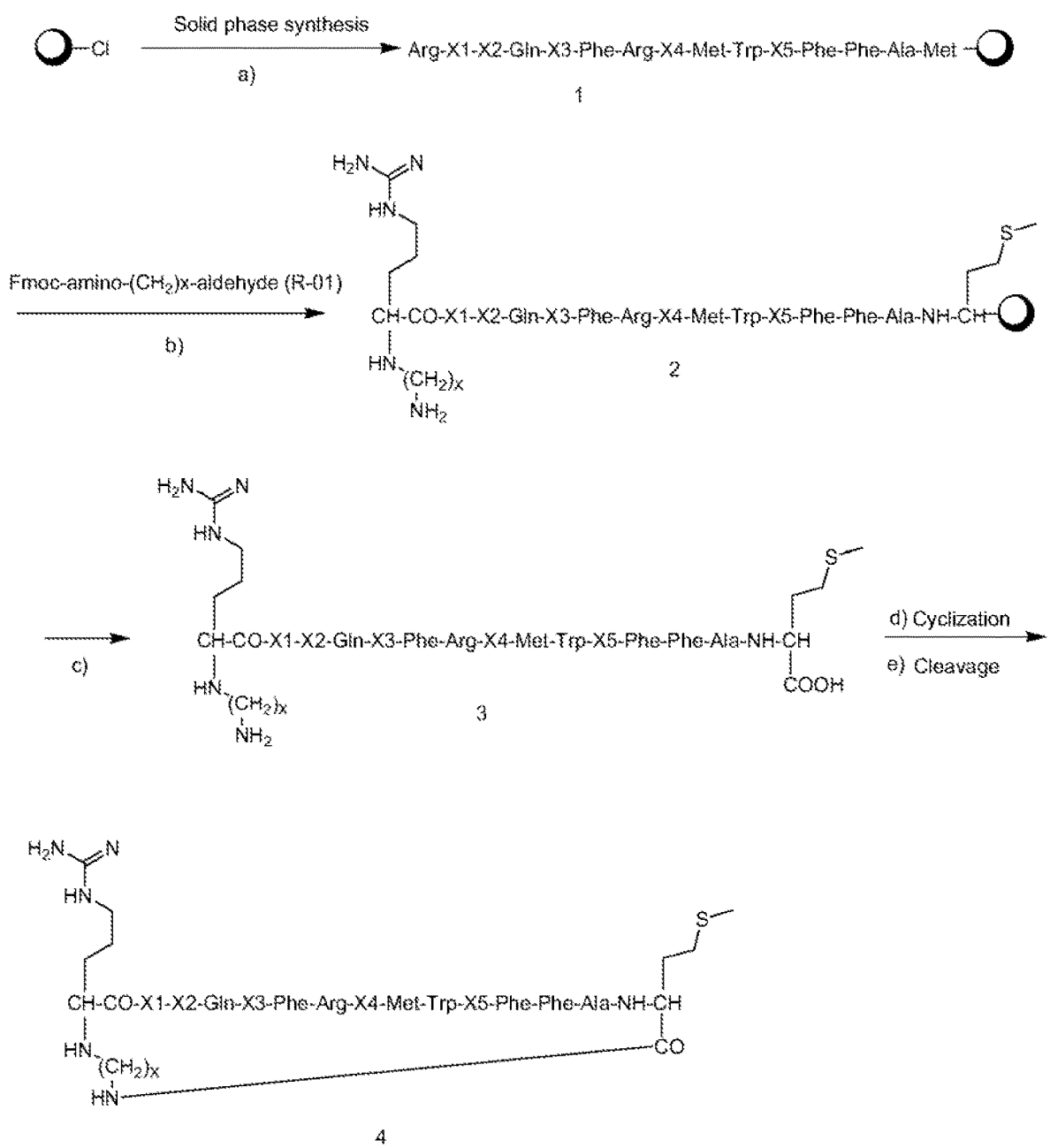
FIG. 4 illustrative example of synthesis of the peptides of the invention (Scheme 1). Conditions a) Fmoc-Met-OH (0.8 eq), DIEA (4 eq), DCM (5 mL), 2 h; then MeOH, 30 min; Coupling of other Fmoc-protected amino acids with HBTU (2.85 eq) and DIEA (6 eq), 1 h; and deblocking with 20% piperidine/DMF, 30 min; b) Fmoc-amino-$(CH_2)_x$-aldehyde (R-01) (1.5 eq), trimethoxymethane (6 eq), $CH_3COOH$ (6 eq), 10 min and $NaBH_3CN$ (4.5 eq), 1 h; c) 1% TFA/DCM, 5 min; d) HATU (1.5 eq) in DCM and pH>7 with DIEA; e) 90% TFA/5% EDT/2.5% TIS/2.5% $H_2O$, 2 h.
Figure 5:
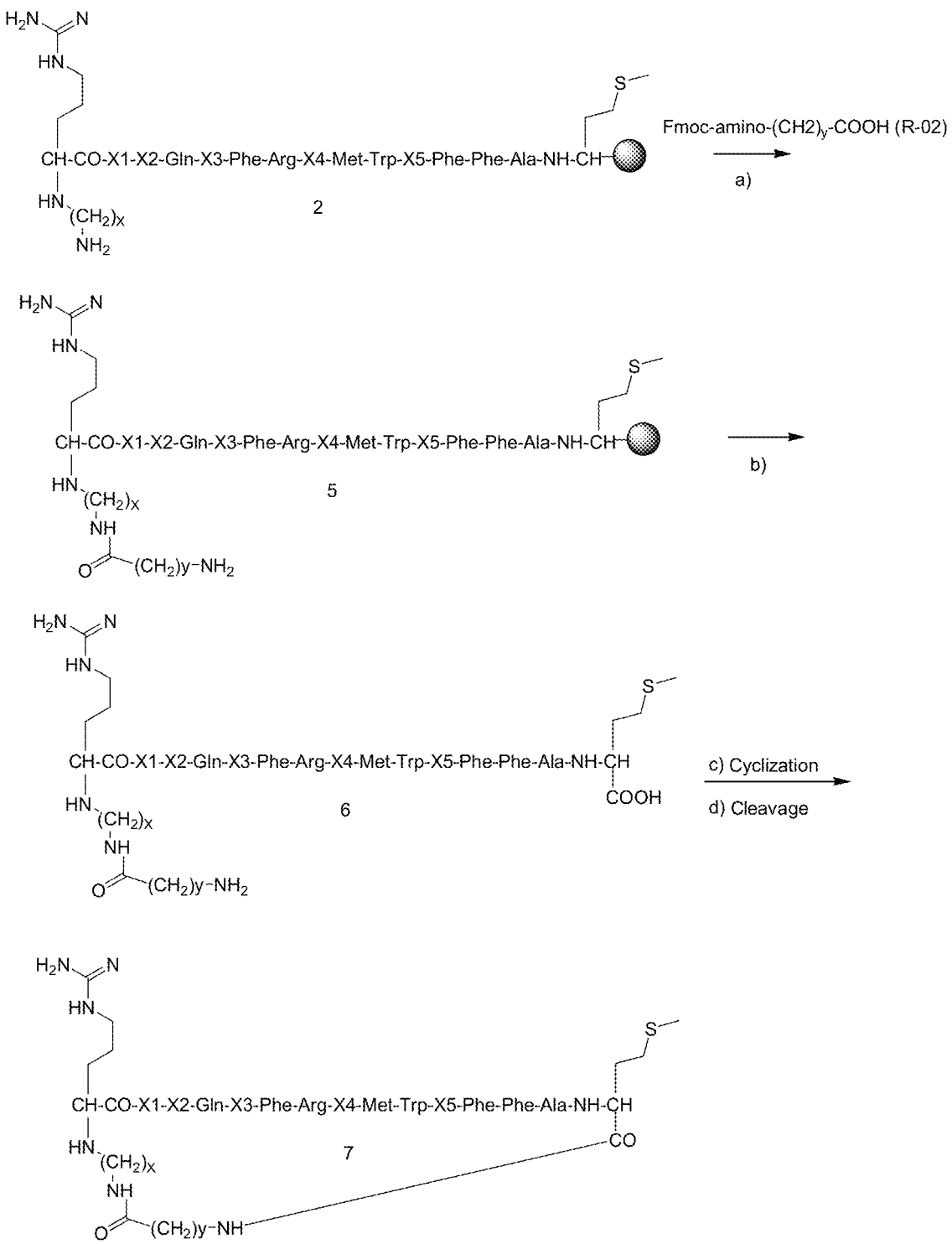
FIG. 5 illustrative example of synthesis of the peptides of the invention (Scheme II). Conditions a) Fmoc-amino-$(CH_2)$y-COOH (R-02) (3 eq), HBTU (2.85 eq), DIEA (6 eq); b) 1% TFA/DCM, 5 min; c) HATU (1.5 eq) in DCM and pH>7 with DIEA; d) 90% TFA/5% EDT/2.5% TIS/2.5% $H_2O$, 2 h.
Figure 6:
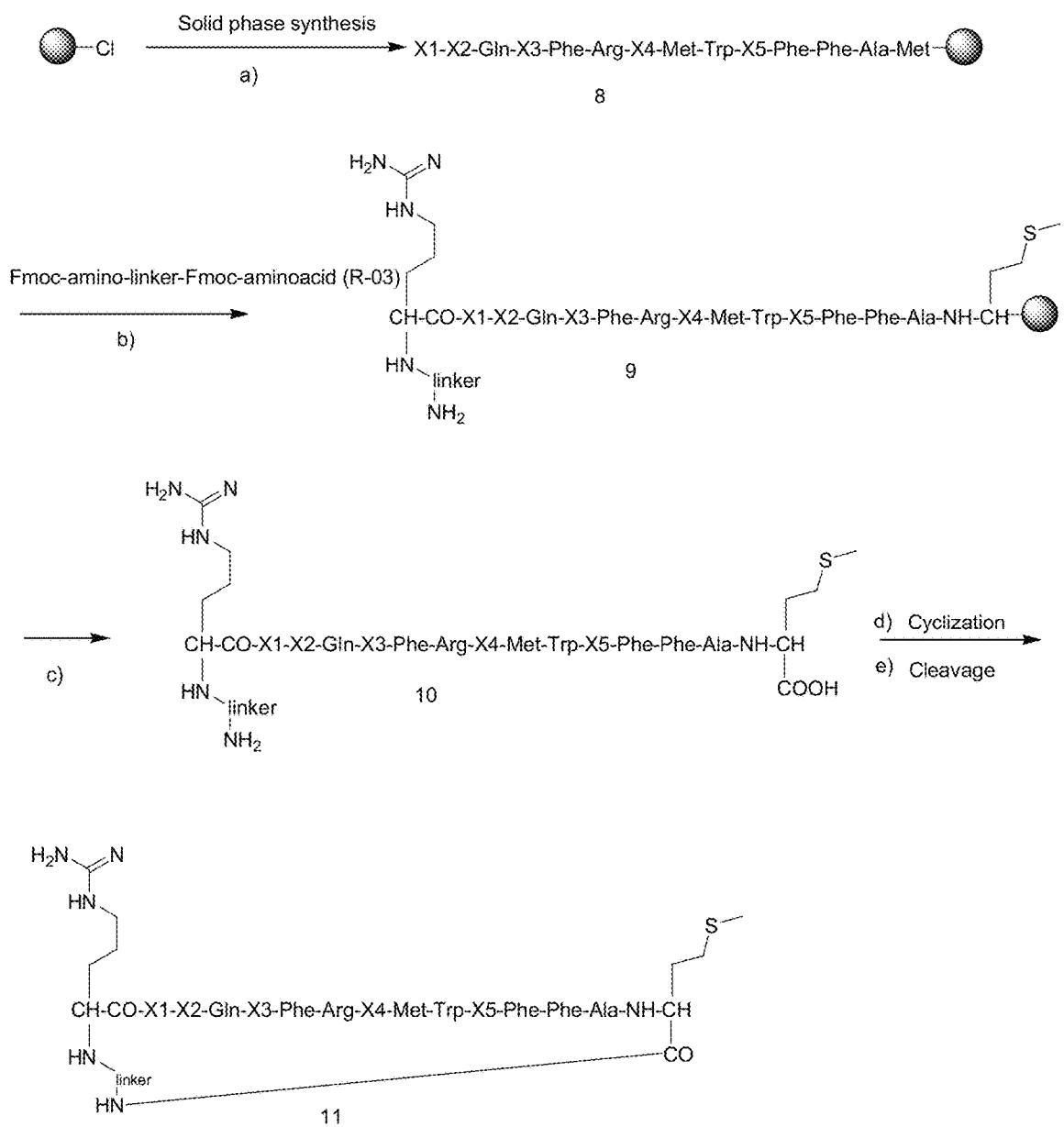
FIG. 6 illustrative example of synthesis of the peptides of the invention (Scheme III). Conditions a) Fmoc-amino-$(CH_2)$y-COOH (R-02) (3 eq), HBTU (2.85 eq), DIEA (6 eq); b) 1% TFA/DCM, 5 min; c) HATU (1.5 eq) in DCM and pH>7 with DIEA; d) 90% TFA/5% EDT/2.5% TIS/2.5% $H_2O$, 2 h.

Illustrative non-limitative examples of synthesis of the peptides of the invention are provided in Schemes I, II and III as set forth in FIGS. 4, 5, and 6. Starting from this information, the skilled person can prepare other linkers comprising either terminal amide groups (such as $(C_1-C_{10})$alkyl-$NR_5$—C(=O), $(C_2-C_{10})$alkenyl-$NR_6$—C(=O), $(C_2-C_{10})$alkynyl-$NR_7$—C(=O)), intermolecular amide groups (such as $(C_1-C_{10})$alkyl-$NR_8$—C(=O)—$(C_1-C_{10})$alkyl-$NR_9$C(=O) or $(C_1-C_{10})$alkyl-C(=O)—$NR_{12}$—$(C_1-C_{10})$alkyl-$NR_{13}$C(=O)), intermolecular amines (such $(C_1-C_{10})$alkyl-$NR_{14}R_{15}$—$(C_1-C_{10})$alkyl-$NR_{16}$—C(=O), esters (such as $C_1-C_{10}$)alkyl-C(=O)—O—$(C_1-C_{10})$alkyl-$NR_{17}$—C(=O), $(C_1-C_{10})$alkyl-O—C(=O)—$(C_1-C_{10})$alkyl-$NR_{18}$—C(=O)), ketones (such as $(C_1-C_{10})$alkyl-C(=O)—$(C_1-C_{10})$alkyl-$NR_{10}$—C(=O)) or ethers (($(C_1-C_{10})$alkyl-O—$(C_1-C_{10})$alkyl-$NR_{11}$—C(=O)).

With reference to Scheme I in FIG. 4, the conditions for this reaction scheme include: a) Fmoc-Met-OH (0.8 eq), DIEA (4 eq), DCM (5 mL), 2 h; then MeOH, 30 min; Coupling of other Fmoc-protected amino acids with HBTU (2.85 eq) and DIEA (6 eq), 1 h; and deblocking with 20% piperidine/DMF, 30 min; b) Fmoc-amino-$(CH_2)_x$-aldehyde (R-01) (1.5 eq), trimethoxymethane (6 eq), $CH_3COOH$ (6 eq), 10 min and $NaBH_3CN$ (4.5 eq), 1 h; c) 1% TFA/DCM, 5 min; d) HATU (1.5 eq) in DCM and pH>7 with DIEA; e) 90% TFA/5% EDT/2.5% TIS/2.5% $H_2O$, 2 h.

With reference to Scheme II in FIG. 5, the conditions for this reaction scheme include: a) Fmoc-amino-$(CH_2)_y$—COOH (R-02) (3 eq), HBTU (2.85 eq), DIEA (6 eq); b) 1% TFA/DCM, 5 min; c) HATU (1.5 eq) in DCM and pH>7 with DIEA; d) 90% TFA/5% EDT/2.5% TIS/2.5% $H_2O$, 2 h.

With reference to Scheme III in FIG. 6, the conditions for this reaction scheme include: a) Fmoc-Met-OH (0.8 eq), DIEA (4 eq), DCM (5 mL), 2 h; then MeOH, 30 min; Coupling of other Fmoc-protected amino acids with HBTU (2.85 eq) and DIEA (6 eq), 1 h; and deblocking with 20% piperidine/DMF, 30 min; b) Fmoc-amino-linker-Fmoc-amino acid (R-03) (1.5 eq), HATU (1.9 eq), DIEA (3 eq), 2 h; c) 1% TFA/DCM, 5 min; d) HATU (1.5 eq) in DCM and pH>7 with DIEA. e) 90% TFA/5% EDT/2.5% TIS/2.5% $H_2O$, 2 h.

In a second aspect, the present invention provides a construct.

In the present invention, the term "cell-penetrating agent" comprises any agent that facilitates the delivery of the peptide of the invention across a cell membrane without negatively affecting the ability of the peptide to bind and inhibit FoxP3.

In one embodiment of the second aspect of the invention, the cell-penetrating agent is a cell penetrating peptide. In this embodiment, the construct corresponds to a fusion protein.

In the present invention the term "cell penetrating peptide" ("CPP") refers to short peptides that facilitate cellular uptake of various molecular cargos (from nanosize particles to small chemical molecules and large fragments of DNA). The "cargo" is associated to peptides via the C(t) or N(t), either through chemical linkage via covalent bonds or through non-covalent interactions. The function of the CPPs are to deliver the cargo into cells, a process that commonly occurs through endocytosis with the cargo delivered to delivery vectors for use in research and medicine. Current use is limited by a lack of cell specificity in CPP-mediated cargo delivery and insufficient understanding of the modes of their uptake. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only nonpolar residues, with low net charge or have hydrophobic amino acid groups that are crucial for cellular uptake. The conjugation of the CPP to the peptide provided in the present invention can be performed following well-known routine protocols, such as solid phase synthesis or solution selective capping. (cf. Copolovici D. M. et al., "Cell-Penetrating Peptides: Design, Synthesis, and Applications", 2014, ACS Nano, 2014, 8 (3), pp 1972-1994).

Virtually any cell penetrating peptide with capacity to internalize a peptide in a cell can be used; nevertheless, in a particular embodiment, said carrier peptide is a peptide comprising a "PTD" ("protein transduction domain") segment. Illustrative non-limiting examples of proteins comprising protein transduction domains (PTDs) include the human immunodeficiency virus 1 (HIV-1) TAT ("transacting translational protein") protein, the *Drosophila* antennapedia homeotic transcription factor (Antp) and the herpesvirus simplex 1 (HSV-1) VP22 DNA-binding protein, although it has also been suggested that other proteins have this property of internalizing peptides in cells, such as influenza virus hemagglutinin, lactoferrin, fibroblast growth factor-1, fibroblast growth factor-2 and the Hoxa-5, Hoxb-4 and Hoxc-8 proteins (Ford K. G. et al., Gene Therapy, 2001; 8:1-4).

The peptide of the invention can be bound to any one of the (amino or carboxyl) terminal ends of the carrier peptide with capacity to internalize a peptide of the invention in a cell. Therefore, in a particular embodiment, the carboxyl-terminal end of the peptide of the invention is bound to the amino-terminal end of said carrier peptide, whereas in another particular embodiment, the amino-terminal end of the peptide of the invention is bound to the carboxyl-terminal end of said carrier peptide.

The peptide of the invention may or may not be directly bound to the cell penetrating peptide. Therefore, in a particular embodiment, optionally in combination with any one of the embodiments provided above or below, the peptide of the invention is directly bound to the cell penetrating peptide. In another embodiment, optionally in combination with any one of the embodiments provided above or below, the construct of the second aspect of the invention further comprises a spacer peptide located between the peptide as defined in the first aspect of the invention and the cell penetrating peptide. Said spacer peptide is advantageously a peptide with structural flexibility, such as a peptide giving rise to a non-structured domain. Virtually any peptide with structural flexibility can be used as a spacer peptide; nevertheless, illustrative non-limiting examples of said spacer peptides include peptides containing repeats of amino acid moieties, e.g., of Gly and/or Ser, or any other suitable repeat of amino acid moieties.

In another embodiment of the second aspect of the invention, the cell-penetrating agent is a nanoparticle delivery system, which is known to be biocompatible and protect the active ingredient from degradation.

The term "nanoparticle" as used herein, refers to a particle with at least two dimensions at the nanoscale, particularly with all three dimensions at the nanoscale, where the nanoscale is the range about 1 nm to about 300 nm. Particularly, when the nanoparticle is substantially rod-shaped with a substantially circular cross-section, such as a nanowire or a nanotube, the "nanoparticle" refers to a particle with at least two dimensions at the nanoscale, these two dimensions being the cross-section of the nanoparticle.

Biodegradable nanoparticle delivery systems that increase intracellular uptake, e.g., polymeric and surface modified nanoparticles as described in US 2009/0136585 and, can also be used. Examples include poly DL-lactide-co-glycolide (PLGA) nanoparticles, e.g., surface-modified with known surface-modifying agents, such as heparin, dodecylmethylammonium bromide (DMAB), DEAE-Dextran, lipofectin, and fibrinogen, among others The term "lipidic nanoparticle" as used herein, refers to a nanoparticle whose membrane is totally made of lipids. Suitable lipids include, without limitation, phospholipids such as phosphatidylcholines ("PC's"), phosphatidylethanolamines ("PE's"), phosphatidyilserines ("PS's"), phosphatidylglycerols ("PG's"), phosphatidylinositols ("PI's") and phosphatidic acids ("PA's"). Such phospholipids generally have two acyl chains, these being either both saturated, both unsaturated or one saturated and one unsaturated; said chains include, without limitation: myristate, palmitate, stearate, oleate, linoleate, linolenate, arachidate, arachidonate, behenate and lignocerate chains. Phospholipids can also be derivatized, by the attachment thereto of a suitable reactive group. Such a group is generally an amino group, and hence, derivatized phospholipids are typically phosphatidylethanolamines. The different moieties suited to attachment to PE's include, without limitation: acyl chains, useful for enhancing the fusability of liposomes to biological membranes; peptides, useful for destabilizing liposomes in the vicinity of target cells; biotin and maleimido moieties, useful for linking targeting moieties such as antibodies to liposomes; and various molecules such as gangliosides, polyalkylethers, polyethylene glycols and organic dicarboxylic acids. Other lipids which can constitute the membrane of the nanoparticle include, but are not limited to, cholesterol and DOPC.

In one embodiment, the lipidic nanoparticle is selected from the group consisting of liposomes and solid-lipid nanoparticle. In another embodiment, the lipidic nanoparticle is a liposome.

The term "solid lipid nanoparticle" refers to particles, typically spherical, with an average diameter between 10 to 1000 nanometers. Solid lipid nanoparticles possess a solid lipid core matrix that can solubilize lipophilic molecules. The lipid core is stabilized by surfactants (emulsifiers). The term lipid is used here in a broader sense and includes triglycerides (e.g. tristearin), diglycerides (e.g. glycerol bahenate), monoglycerides (e.g. glycerol monostearate), fatty acids (e.g. stearic acid), steroids (e.g. cholesterol), and waxes (e.g. cetyl palmitate). All classes of emulsifiers (with respect to charge and molecular weight) have been used to stabilize the lipid dispersion.

In the present invention, the term "liposome" is to be understood as a self-assembling structure comprising one or more lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

Liposomes can have a single lipid bilayer (unilamellar liposomes, "ULVs"), or multiple lipid bilayers (multilamellar liposomes, "MLVs" or "SPLVs"). Each bilayer surrounds, or encapsulates, an aqueous compartment. Given this encapsulation of aqueous volume within a protective barrier of lipid molecules, liposomes are able to sequester encapsulated molecules, e. g., nucleic acids, away from the degrading effects of factors, e. g., nuclease enzymes, present in the external environment.

Liposomes can have a variety of sizes, e. g., an average diameter as low as 25 nm or as high as 10,000 nm or more. Liposome's size is affected by a number of factors, e. g., lipid composition and method of preparation, well within the purview of ordinarily skilled artisans to determine and account for, and is determined by a number of techniques, such as quasi-elastic light scattering, also within the skilled person in the art knowledge.

Various methodologies, also well-known to those skilled in the art, such as sonication, or homogenization, and milling, can be used to prepare liposomes of a smaller size from larger liposomes. Extrusion can be used to size reduce liposomes, that is to produce liposomes having a predetermined mean size by forcing the liposomes, under pressure, through filter pores of a defined, selected size. Tangential flow filtration can also be used to regularize the size of liposomes, that is, to produce a population of liposomes having less size heterogeneity, and a more homogeneous, defined size distribution.

The peptide of the invention can be encapsulated within the particle using well-known methods in the state of the art, such as those disclosed in Tandrup Schmidt S. et al., "Liposome-Based Adjuvants for Subunit Vaccines: Formulation Strategies for Subunit Antigens and Immunostimulators", Pharmaceutics, 2016 Mar. 10; 8(1).

The cell-penetrating agents can be further functionalized by conjugating molecules with the ability of recognizing and binding to molecules on Treg cells' surface.

In one embodiment, the cell-penetrating agent also protects peptides of the invention against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

If desired, the fusion protein of the invention can optionally include an amino acid sequence useful for the isolation or purification of the fusion protein of the invention. Said sequence will be located in a region of the fusion protein of the invention which does not adversely affect the functionality of the peptide of the invention. Virtually any amino acid sequence which can be used to isolate or purify a fusion protein (generically called tag peptides) can be present in said fusion protein of the invention. By way of a non-limiting illustration, said amino acid sequence useful for isolating or purifying a fusion protein can be, for example, an arginine tag (Arg-tag), a histidine tag (His-tag), FLAG-tag, Strep-tag, an epitope which can be recognized by an antibody, such as c-myc-tag, SBP-tag, S-tag, calmodulin-binding peptide, cellulose-binding domain, chitin-binding domain, glutathione S-transferase-tag, maltose-binding protein, NusA, TrxA, DsbA, Avi-tag or β-galactosidase, among others.

The fusion protein of the invention can be obtained by means of a coupling reaction of the peptide of the invention and of the cell penetrating peptide with capacity to internalize a peptide of the invention in a cell, which may have been obtained by conventional synthetic methods, such as those which have been previously mentioned (e.g., solid phase chemical synthesis), or by means of recombinant techniques.

In a third aspect, the present invention provides a combination comprising (a) the peptide of the invention or the construct as defined in the second aspect of the invention or both the peptide and the construct, and (b) one or more immunomodulatory compounds.

In the present invention the term "immunomodulatory compound" refers to a compound which induces, enhances, or suppresses an immune response.

In one embodiment, the one or more immunomodulatory compounds have an effect on cancer cells, i.e., the compound(s) are cancer immunomodulatory compounds. Cancer immunotherapies can be categorized as active, passive or hybrid (active and passive). These approaches exploit the fact that cancer cells often have molecules on their surface that can be detected by the immune system, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Merghoub T. and colleagues provide a complete review about the cancer immunomodulatory compounds in the state of the art (Khalil D. N. et al., "The New Era of Cancer Immunotherapy: Manipulating T-Cell Activity to Overcome Malignancy" Advances in Cancer Research, 2015, vol. 128, pages 1-68. In one embodiment of the third aspect of the invention, the immunomodulatory compound(s) inhibit(s) or regulate(s) the immunosuppressive activity of different Treg lymphocytes. Virtually any compound inhibiting or regulating the immunosuppressive activity of Treg lymphocytes, independently of its mechanism of action (e.g., through the inhibition of scurfin or through other mechanisms), different from the peptides and constructs of the invention, can be present, if desired, in the combination of the third aspect of the invention. Illustrative non-limiting examples of alternative compounds inhibiting or regulating the activity of Treg lymphocytes, different from the peptides and constructs of the invention, which can be used together with the peptides and constructs of the invention include, although they are not limited to, anti-CD25, anti-CTLA4, anti-GITR antibodies, anti-PD-1, anti-PD-L1, anti-LAG3, anti-OX40, compounds inhibiting cytokines TGF-beta, IL-10 or IL-9, chemotherapeutic compounds such as cyclophosphamide fludarabine, or inhibitors of chemokines CCL17 or CCL22, among others.

In a fourth aspect, the present invention provides a veterinary or pharmaceutical composition comprising a therapeutically effective amount of the peptide of the invention or of the construct of the second aspect of the invention or of the combination of the third aspect of the invention, together with at least one veterinary or pharmaceutically acceptable excipient.

The expression "therapeutically effective amount" as used herein, refers to the amount of the peptide or construct or combination that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans without excessive toxicity, irritation, allergic response, immunogenicity or other problems or complications commensurate with a reasonable benefit/risk ratio. Likewise, the term "veterinary acceptable" means suitable for use in contact with a non-human animal.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically or veterinary acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as colouring agents, coating agents, sweetening, and flavouring agents can be present in the composition, according to the judgment of the formulator.

The pharmaceutical compositions containing the peptide or the construct or the combination of the invention can be presented in any dosage form, for example, solid or liquid, and can be administered by any suitable route, for example, oral, parenteral, rectal or topical route, for which they will include the pharmaceutically acceptable excipients necessary for the formulation of the desired dosage form, for example, ointments (lipogels, hydrogels, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminium silicate (Veegum), sodium lauryl sulfate, quaternary ammonium compounds, and combinations thereof.

Exemplary binding agents include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminium hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

In a fifth aspect, the present invention provides the peptide of the first aspect of the invention, or the construct of the second aspect of the invention, or of the combination of the third aspect of the invention for use as a medicament.

When the combination of the third aspect of the invention is administered as a medicament, the administration of each one of the components (the peptide and/or the construct, and the one or more immunomodulatory compound) can be performed sequentially, separately or simultaneously.

Generally, any infectious or neoplastic process in which Treg lymphocytes play an immunosuppressive role can be treated with the peptide of the invention.

Likewise, the peptides and constructs of the invention can be used to enhance antiviral or antitumor vaccines, since their administration after the vaccination, and the subsequent blocking of Treg lymphocytes by the peptides of the invention during their administration, would allow enhancing the response to the components of the vaccine.

It additionally seems that Treg lymphocytes can play a central role in the oral tolerance to an antigen (Huibregtse, I. L. et al., "Induction of ovalbumin-specific tolerance by oral administration of *Lactococcus lactis* secreting ovalbumin", Gastroenterology, 2007, vol. 133, pages 517-528), therefore the peptides of the invention could be used in situations in which this tolerance to orally administered antigens is to be broken.

Illustrative examples of the pathologies which can be potentially treated with the peptides, constructs and combinations of the invention include neoplastic diseases and infectious diseases.

As used herein, the term "neoplastic diseases" includes both tumors (i.e., tissue disorders which cause an increase in volume, particularly, lumps due to an increase in the number of cells forming it, independently of whether they are benign or malignant), and cancer (a disease which is characterized by an uncontrolled proliferation of abnormal cells capable of invading adjacent tissues and disseminating to distant organs). Likewise, the term "infectious diseases" generally relates to diseases caused by infectious agents e.g., viruses, bacteria, fungi, parasites, etc. In this type of infectious or neoplastic (cancerous) process, Treg lymphocytes exert a negative effect, since they are capable of inhibiting the activation of immune responses against infectious or neoplastic processes which would favour the cure.

Figure 2:
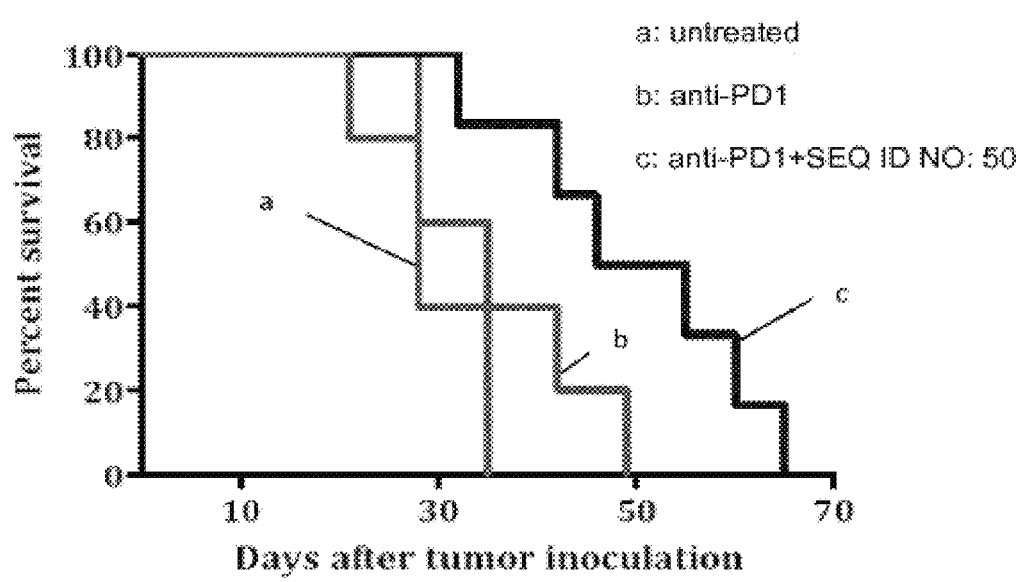
FIG. 2 Kaplan-Meier plots of liver cancer mouse survival. The group of mice treated with anti-PD+SEQ ID NO: 50 was compared with the rest of the groups with the log-rank test. *, P<0.05.
Figure 3:
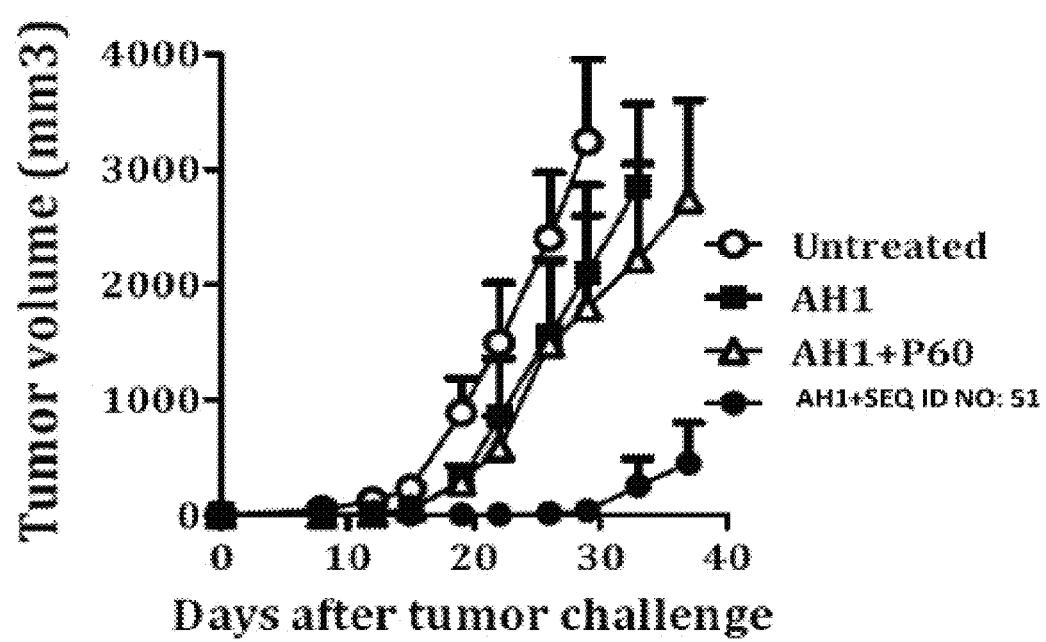
FIG. 3 represents the mean tumor volume for a group of mice treated with AH1 peptide emulsified in IFA and treated with saline, or with p60 (SEQ ID NO: 1) or with the peptide SEQ ID NO: 51 during 10 days, 10 days before the challenge to colon cancer cells.

As it is shown in FIGS. 1 and 2 the peptides of the invention show antitumor activity against liver cancer cells and in FIG. 3 it is shown that the peptides of the invention are effective in preventing colon cancer cell's growth.

Thus, in one embodiment, the peptide of the invention, the construct of the second aspect of the invention, the combination of the third aspect of the invention and/or the pharmaceutical or veterinary composition of the fourth aspect of the invention is used in the treatment of colon cancer or liver cancer.

Illustrative non-limiting examples of viral infections which can be treated with the peptides and constructs of the invention include virtually any infection of viral origin, for example, infections caused by hepatitis B virus, hepatitis C virus, HIV, human papillomavirus, herpes viruses, for example, human herpesviruses such as herpes simplex virus type 1 (HSV-1), herpes simplex virus type 2 (HSV-2), varicella zoster virus (VZV), cytomegalovirus (CMV), human herpesvirus 6 (HHV-6), human herpesvirus 7 (HHV-7), Epstein-Barr virus (EBV), Kaposi's herpesvirus (HHV-8), etc. Illustrative non-limiting examples of bacterial infections which can be treated with the peptides and constructs of the invention include, although they are not limited to, infections caused by *Mycobacterium leprae*, infections caused by *Mycobacterium tuberculosis*, infections caused by *Yersinia pestis*, gastric infection caused by *Helicobacter pylori*, etc.

Illustrative non-limiting examples of fungal infections which can be treated with the peptides and constructs of the invention include, although they are not limited to, infections caused by *Candida albicans*, infections caused by *Trichophyton rubrum*, infections caused by *Aspergillus* sp., etc. Illustrative non-limiting examples of parasitic infections which can be treated with the peptides and constructs of the invention include, although they are not limited to, leishmaniasis, e.g., visceral leishmaniasis, infections such as malaria caused by *Plasmodium* parasites, toxoplasmosis, etc.

Illustrative non-limiting examples of neoplastic diseases which can be treated with the peptides and constructs of the invention include, although they are not limited to, papillomas, adenomas, lipomas, osteomas, myomas, angiomas, nevi, mature teratomas, carcinomas, sarcomas or immature teratomas, for example, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocarcinoma, head and neck cancer, etc.

Alternatively, the peptide of the invention and the construct of the second aspect of the invention can be obtained by means of recombinant DNA technology. Therefore, in another aspect, the invention provides a DNA sequence encoding a peptide or a construct of the invention. Said DNA sequence can be easily deduced from the amino acid sequence of the peptide or of the construct of the invention.

Said DNA sequence can be contained in a DNA construct. Therefore, in another aspect, the invention provides a DNA construct comprising a DNA sequence encoding a peptide or construct of the invention. Said DNA construct can contain, operatively bound, a sequence regulating the expression of the DNA sequence encoding the peptide or construct of the invention. Control sequences are sequences controlling and regulating the transcription and, where appropriate, the translation of the peptide or construct of the invention, and include promoter, terminator sequences etc., functional in transformed host cells comprising said DNA sequence or construct. In a particular embodiment, said expression control sequence is functional in bacteria. Said DNA construct advantageously further comprises a marker or gene encoding a motif or a phenotype which allows selecting the transformed host cell with said DNA construct. The DNA construct provided by this invention can be obtained by means of using techniques that are widely known in the state of the art (Sambrook et al., "Molecular cloning, a Laboratory Manual", 4th ed., Cold Spring Harbor Laboratory Press, N.Y., 2012 Vol 1-3) Chapter 3 from Vol 1: Cloning and Transformation with Plasmid Vectors).

The DNA sequence or the DNA construct provided by this invention can be inserted in a suitable vector. Therefore, in another aspect, the invention relates to a vector, such as an expression vector, comprising said DNA sequence or construct. The choice of the vector will depend on the host cell in which it will be subsequently introduced. By way of example, the vector wherein said DNA sequence is introduced can be a plasmid or a vector which, when it is introduced in a host cell, is or is not integrated in the genome of said cell. Said vector can be obtained by conventional methods known by persons skilled in the art (Sambrook et al., 2012, mentioned above).

In another aspect, the invention relates to a host cell, such as a transformed host cell, comprising a DNA sequence or a DNA construct provided by this invention or a vector as has been previously mentioned. Said cell can be a prokaryotic or eukaryotic cell.

Likewise, in another aspect, the invention relates to a process for producing a peptide of the invention or a construct of the invention comprising growing a host cell comprising the sequence, DNA construct or vector provided by this invention under conditions allowing the production of said peptide or construct of the invention and, if desired, recovering said peptide or construct of the invention. The conditions for optimizing the culture of said host cell will depend on the host cell used. If desired, the process for producing the peptide or the construct of the invention further includes the isolation and purification of said peptide or construct.

In addition, said DNA sequences and DNA constructs provided by this invention can be used in the preparation of vectors and cells for treating a pathology in which it is suitable or necessary to transiently regulate or block the immunosuppressive activity of Treg lymphocytes. Therefore, in another aspect, the invention relates to the use of said DNA sequences and DNA constructs in the preparation of vectors and cells for the treatment of a pathology in which it is suitable or necessary to transiently regulate or block the immunosuppressive activity of Treg lymphocytes, for example, viral, bacterial, fungal, parasitic infections, etc., and neoplastic diseases. According to this aspect of the invention, said DNA sequence or construct can be put in contact with a gene transfer vector, such as a viral or non-viral vector. Suitable viral vectors for putting this embodiment of the invention into practice include, but are not limited to, adenoviral vectors, adeno-associated vectors, retroviral vectors, lentiviral vectors, alphaviral vectors, herspesviral vectors, coronavirus-derived vectors, etc. Suitable non-viral type vectors for putting this embodiment of the invention into practice include, but are not limited to naked DNA, liposomes, polyamines, dendrimers, cationic glycopolymers, liposome-polycation complexes, proteins, receptor-mediated gene transfer systems, etc.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention.

Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

1. General Procedure for Preparative HPLC Purification Method

The HPLC measurement was performed using Gilson GX-281 from 233 pump (binary), an autosampler, and a UV detector (wave length=214 or 215 & 254 nm). Solvent A: water with 0.075% TFA; Solvent B: acetonitrile. Different columns and gradients at room temperature depending on the methods (table below).

3. General Procedure for LCMS Analysis:

LCMS analysis was performed using a HPLC Agilent 1200 apparatus coupled to a triple quadrupole mass spectrometer (6410). UV detection at 220 nm. Solvent A: water with TFA at 0.1%; solvent B: acetonitrile with TFA at 0.1%. Xbridge C18 Column (2.1×30 mm, 3.5 µm) at room temperature. Gradient: from 10% to 80% of B in 0.9 min at 1.0 ml/min; then to 90% of B for 0.6 min at 1.0 ml/min and then maintained at 10% of B for 0.5 min at 1.0 ml/min.

The following abbreviations have been used in the examples:

HPLC: High-performance liquid chromatography; TLC: thin layer chromatography; MW: microwaves; calc.: calculated; rt: room temperature; Rt: Retention time; min: minute; Prep: Preparative; eq: equivalent; rpm: revolutions per minute; UV: ultraviolet; PG: protective group; TFA: trifluoroacetic acid; CTC: chlorotrityl chloride; Boc: tert-butoxycarbonyl; DCM: dichloromethane; DIPEA or DIEA: N,N-diisopropylethylamine; MeOH: methanol; DMF: dimethylformamide; HATU: 1-[Bis(dimethylamino)methylene]-1H-1,2,3-triazolo[4,5-b]pyridinium 3-oxid hexafluorophosphate; HBTU: N,N,N',N'-Tetramethyl-O-(1H-benzotriazol-1-yl)uronium hexafluorophosphate; EDT: ethanedithiol; TIS: thioanisole; HOBt Hydroxybenzotriazole; DIC: N,N'-Diisopropylcarbodiimide; THF: tetrahydrofuran; DEAD: diethyl azodicarboxylate; Pbf: 2,2,4,6,7-pentamethyldihydrobenzofurane; PPh3: triphenylphosphine;

| Method | Gradient (at room temperature) | Reverse Phase HPLC Column |
|---|---|---|
| 1 | 20% of B to 50% of B within 60 min at 20 mL/min | Agilent SB-phenyl prep HT (250 × 30 mm; 7 µm) |
| 2 | 13% of B to 43% of B within 60 min at 20 mL/min | Agilent SB-phenyl prep HT (250 × 30 mm; 7 µm) |
| 3 | 8% of B to 38% of B within 60 min at 20 mL/min | Agilent SB-phenyl prep HT (250 × 30 mm; 7 µm) |
| 4 | 9% of B to 39% of B within 60 min at 25 mL/min; then 90% B at 25 mL/min over 48 min | Luna C18 (200 × 25 mm; 10 µm) and Gemini C18 (150*30 mm; 5 µm) in series |
| 5 | 8% of B to 38% of B within 60 min at 25 mL/min; then 90% B at 25 mL/min over 48 min | Luna C18 (200 × 25 mm; 10 µm) and Gemini C18 (150*30 mm; 5 µm) in series |
| 6 | 14% of B to 39% of B within 60 min at 25 mL/min; then 90% B at 25 mL/min over 45 min | Luna C18 (200 × 25 mm; 10 µm) and Gemini C18 (150*30 mm; 5 µm) in series |
| 7 | 15% of B to 45% of B within 60 min at 20 mL/min | Agilent SB-phenyl prep HT (250 × 30 mm; 7 µm) |
| 8 | 15% of B to 45% of B within 60 min at 20 mL/min | Agilent SB-phenyl prep HT (250 × 30 mm; 7 µm) |

2. General Procedure for HPLC Analysis

HPLC-analysis was performed using a Shimadzu LC-20AB or LC-20AD or Agilent 1100 Series HPLC and UV detection (210/220/254 nm). Solvent A: water with 0.1% TFA; Solvent B: acetonitrile with 0.1% TFA. Different columns and gradients depending on the methods (table below).

EtOAc or EA: ethyl acetate; Ns: nitrobenzenesulfonyl; NsCl: 2-nitrobenzenesulfonyl chloride; Fmoc: fluorenylmethyloxycarbonyl; Fmoc-Cl: 9-Fluorenylmethoxycarbonyl chloride; Fmoc-OSu: 9-Fluorenylmethyl N-succinimidyl carbonate; Trt: trityl.

Table of protected amino acids used in the examples of peptide synthesis provided below:

| Method | Reverse phase HPLC Column | Gradient, Temperature |
|---|---|---|
| 1 | Zorbax Eclipse XDB-C18 column (4.6 × 150 mm, 5 µm) | 10% of B to 60% of B within 27 min at 1 mL/min, 35° C. |
| 2 | Gemini-NX (C18, 5 µm, 110 Å) column 150 × 4.6 mm, 5 µm) | 25% of B to 55% of B within 20 min at 1 mL/min, 30° C. |
| 3 | Gemini-NX (C18, 5 µm, 110 Å) column (150 × 4.6 mm, 5 µm) | 20% of B to 50% of B within 20 min at 1 mL/min, 30° C. |
| 4 | Gemini-NX (C18, 5 µm, 110 Å) column (150 × 4.6 mm, 5 µm) | 25% of B to 55% of B within 20 min at 1 mL/min; then 3 min of B. 30° C. |
| 5 | Symmetry C18 column (4.6 × 150 mm, 5 µm) | 20% of B to 80% of B within 30 min at 1 mL/min, 25° C. |

| Chemical name | | CAS |
|---|---|---|
| Fmoc-Met-OH | Fmoc-L-methionine | 71989-28-1 |
| Fmoc-Ala-OH | Fmoc-L-alanine | 35661-39-3 |
| Fmoc-Phe-OH | Fmoc-L-phenylalanine | 35661-40-6 |
| Fmoc-Pro-OH | Fmoc-L-proline | 71989-31-6 |
| Fmoc-Trp(Boc)-OH | $N_{(in)}$-Boc-$N_\alpha$-Fmoc-L-tryptophan | 143824-78-6 |
| Fmoc-Lys(Boc)-OH | $N_\alpha$-Fmoc-Nε-Boc-L-lysine | 71989-26-9 |
| Fmoc-Arg(Pbf)-OH | $N_\alpha$-Fmoc-$N_\omega$-Pbf-L-arginine | 154445-77-9 |
| Fmoc-Gln(Trt)-OH | $N_\alpha$-Fmoc-$N_\delta$-trityl-L-glutamine | 132327-80-1 |
| Fmoc-D-Ala-OH | Fmoc-D-alanine | 79990-15-1 |
| Fmoc-Gly-OH | Fmoc-glycine | 29022-11-5 |
| Fmoc-Ser(tBu)-OH | Fmoc-O-tert-butyl-L-serin | 71989-33-8 |
| Fmoc-Asp(tBu)-OH | Fmoc-L-aspartic acid 4-tert-butyl ester | 71989-14-5 |
| Fmoc-D-Asp(tBu)-OH | Fmoc-D-aspartic acid 4-tert-butyl ester | 112883-39-3 |
| Ac-Gly-OH | N-Acetylglycine | 543-24-8 |

All of them bought from Novabiochem, Merck Millipore or Sigma-Aldrich.

Synthesis of Linear Peptides

Synthesis of Peptide with SEQ ID NO: 3

To a mixture containing CTC Resin (0.2 mmol, 0.17 g, 1.2 mmol/g) and Fmoc-Met-OH (74.3 mg, 0.2 mmol, 1.0 eq) was added DCM (2.00 mL), then DIEA (6.00 eq) was added and mixed for 2 hours. And then MeOH (0.2 mL) was added and mixed for 30 min for capping. 20% piperidine in DMF was used for deblocking. And the others amino acids were coupled with 3 eq using activator reagents, HATU (2.85 eq) and DIPEA (6.0 eq) in DMF (2 mL). The reaction was monitored by ninhydrin color reaction or Tetrachloro-p-benzoquinone test. After synthesis completion, the peptide resin was washed with DMF×3, MeOH×3, and then dried under $N_2$ bubbling overnight. After that the peptide resin was treated with 2.5% EDT/2.5% $H_2O$/95% TFA for 3 h for 2 times. The peptide solution was precipitated with cold tert-butyl methyl ether (8 mL) and centrifuged (2 min at 3000 rpm). The supernatant was decanted and the precipitate was washed twice with tert-butyl methyl ether (100 mL). The crude peptide was collected and dried under vacuum for 2 hours, then purified by prep-HPLC (General procedure, method 4) and then lyophilized to give the final product SEQ ID NO: 3 (175 mg, 3.1% yield). ESI-MS (M+1): 1993.9 calc. for $C_{95}H_{132}N_{24}O_{20}S_2$: 1992.9, m/z found 997.5 [M/2+H]+ 665.4 [M/3+H]+. HPLC analytical method 4, Rt=9.78 min.

Following the same protocol as the one provided above for SEQ ID NO: 3, the remaining lineal peptides of this section were analogously prepared.

In those cases wherein the C(t) of the peptide was amidated (being one of $R_2'$ or $R_2$—C(=O)$NH_2$) a Rink Amide MBHA resin (Novabiochem, Cat No 431041-83-79) was used to perform the solid phase synthesis instead of the CTC Resin; and when the N(t) of the peptide was acetylated, an acetylated Gly residue ($CH_3$—C(=O)—NH—$CH_2$—C(=O)OH) was incorporated as the last amino acid in the solid phase synthesis).

TABLE 4

| SEQ. ID. NO. | Method Prep-HPLC | [M/2 + H]+ | [M/3 + H]+ | Method Analytical HPLC | Rt (min) |
|---|---|---|---|---|---|
| 5 | 5 | 975.6 | 650.8 | 4 | 9.27 |
| 6 | 6 | 975.7 | 650.7 | 4 | 10.19 |
| 42 | 3 | 967.5 | 645.4 | 3 | 11.61 |
| 2 | | | | 1 | 15.9 |
| 4 | | | | 1 | 16.8 |

TABLE 4-continued

| SEQ. ID. NO. | Method Prep-HPLC | [M/2 + H]+ | [M/3 + H]+ | Method Analytical HPLC | Rt (min) |
|---|---|---|---|---|---|
| 7 | | | | 1 | 15.5 |
| 8 | | | | 1 | 20.6 |
| 9 | | | | 1 | 17.3 |
| 10 | | | | 1 | 15.0 |
| 11 | | | | 1 | 19.09 |
| 12 | | | | 1 | 20.06 |
| 13 | | | | 1 | 17.9 |
| 15 | | | | 1 | 15.4 |
| 16 | | | | 1 | 16.8 |
| 17 | | | | 1 | 15.9 |
| 18 | | | | 1 | 16.3 |
| 19 | | | | 1 | 14.4 |
| 20 | | | | 1 | 15.5 |
| 21 | | | | 1 | 16.3 |
| 22 | | | | 1 | 18.2 |
| 23 | | | | 1 | 16.7 |
| 24 | | | | 1 | 17.1 |
| 25 | | | | 1 | 19.0 |
| 26 | | | | 1 | 15.9 |
| 27 | | | | 1 | 17.7 |
| 28 | | | | 1 | 16.1 |
| 29 | | | | 1 | 16.1 |
| 30 | | | | 1 | 14.7 |
| 31 | | | | 1 | 16.1 |
| 32 | | | | 1 | 15.1 |
| 33 | | | | 1 | 17.8 |
| 34 | | | | 1 | 17.9 |
| 35 | | | | 1 | 17.3 |
| 36 | | | | 1 | 16.5 |
| 37 | | | | 1 | 15.7 |
| 38 | | | | 1 | 16.4 |
| 39 | | | | 1 | 16.5 |
| 40 | | | | 1 | 16.4 |
| 41 | | | | 1 | 15.9 |
| 43 | | | | 1 | 16.4 |
| 44 | | | | 1 | 18.0 |
| 45 | | | | 1 | 19.5 |
| 3 | | | | 5 | 14.72 |
| 14 | | | | 5 | 15.36 |
| 46 | | | | 5 | 14.49 |
| 47 | | | | 5 | 14.30 |
| 48 | | | | 5 | 14.78 |

Empty cells in the column "Preparative HPLC purification method" means that no particular HPLC purification method was performed.

Synthesis of Head-to-Tail Cyclic Peptides

Synthesis of Peptide with SEQ ID NO: 51

The peptide was synthesized by solid phase synthesis using Fmoc-Met-CTC Resin (0.3 mmol, 0.5 mmol/g). The other amino acids were coupled with HBTU (0.324 g, 2.85 eq) and DIEA (0.32 mL, 6.0 eq) for 1 hour. 20% piperidine in DMF was used for deblocking. The coupling reaction was monitored by ninhydrin color reaction. After washing with MeOH (3×), the resin was dried under vacuum for 2 hours. The resin was treated with 1% TFA/DCM (10 mL) for 5 min and filtered, the TFA-mixture was adjusted to pH of 7 with DIEA, the TFA-mixture was added into 300 mL DCM, it was treated with DIC (2.0 eq) and HOBt (2.0 eq) for 16 hours. Evaporated to give the crude protecting peptide, the peptide was treated with 95% TFA/2.5% TIS/2.5% $H_2O$ (100 mL) for 2 hours. The TFA mixture was precipitated with cold methyl tert-butyl ether (100 mL) and centrifuged (5000 rpm, 2 min). The supernatant was decanted and the precipitate was washed one more time (50 mL). The crude peptide was dried under vacuum for 2 hours, then purified by prep-HPLC (General procedure, method 7) and then lyophilized to give the final product SEQ ID NO: 51 (16.1 mg, 2.81%). ESI-MS (M+1): 1915.9 calc. for $C_{94}H_{130}N_{24}O_{16}S_2$: 1914.9, m/z found 958.4 [M/2+H]+639.3 [M/3+H]+. HPLC analytical method 2, Rt=12.65 min.

Analogously, the peptide of sequence SEQ ID NO: 50 was obtained:

TABLE 5

| SEQ. ID. NO. | Method Prep-HPLC | $[M/2 + H]^+$ | $[M/3 + H]+$ | Method Analytical HPLC | Rt (min) |
|---|---|---|---|---|---|
| 50 | 8 | 958.7 | 639.4 | 2 | 11.56 |

Synthesis of Peptide with SEQ ID NO: 52

To a mixture containing CTC resin (0.2 mmol, sub=1.0 mmol/g, 200 mg) and Fmoc-Met-OH (59.36 mg, 0.16 mmol, 0.8 eq) was added DCM (5 mL), DIEA (4.0 eq) was added dropwise. The resin was mixed 2 hours. MeOH was added (0.5 mL) and mixed for 30 min. The other amino acids were coupled with HBTU (2.85 eq) and DIEA (6.0 eq) for 1 hour. In the last step, to a mixture containing Fmoc-3-amino propanal (R-01a) (1.5 eq) and trimethoxymethane (6 eq) and $CH_3COOH$ (6 eq), 10 min later $NaBH_3CN$ (4.5 eq) was added, react about 1 hour. 20% piperidine in DMF was used for deblocking. The coupling reaction was monitored by ninhydrin color reaction. After washing with MeOH, the resin was dried under vacuum for 2 hours. The resin was treated with 1% TFA/DCM (10 mL) for 5 min, evaporated to give the crude peptide and lyophilized to give the crude product, the crude was added into 100 mL DCM, adjust pH>7 by DIEA, and then HATU (1.5 eq) was added. Evaporated to give the crude cyclized peptide. The crude cyclized peptide was treated with 90% TFA/5% EDT/2.5% Tis/2.5% $H_2O$ for 2 hours. The TFA mixture was precipitated with cold methyl tert-butyl ether (100 mL) and centrifuged (5000 rpm, 2 min). The supernatant was decanted and the precipitate was washed one more time (50 mL). The crude peptide was dried under vacuum for 2 hours, then purified by prep-HPLC (General procedure, method 1) and then lyophilized to give the final product SEQ ID NO: 52 (16.4 mg). ESI-MS (M+1): 1973.02 calc. for $C_{97}H_{137}N_{25}O_{12}$: 1972.01, m/z found 986.9 [M/2+H]+658.3 [M/3+H]+. HPLC analytical method 1, Rt=9.48 min.

Synthesis of the Peptide SEQ ID NO: 53

To a mixture containing CTC resin (0.2 mmol, sub=1.0 mmol/g, 200 mg) and Fmoc-Met-OH (59.36 mg, 0.16 mmol, 0.8 eq) was added DCM (5 mL), DIEA (4.0 eq) was added dropwise. The resin was mixed 2 hours. MeOH was added (0.5 mL) and mixed for 30 min. The other amino acids were coupled with HBTU (2.85 eq) and DIEA (6.0 eq) for 1 hour. In the last step, to a mixture containing Fmoc-2-aminoacetaldehyde (R-01b) (1.5 eq) and trimethoxymethane (6 eq) and $CH_3COOH$ (6 eq), 10 min later $NaBH_3CN$ (4.5 eq) was added, react about 1 hour. 20% piperidine in DMF was used for deblocking. Fmoc-Gly-OH (R-02) (3 eq) was coupled with HBTU (2.85 eq) and DIEA (6 eq). The coupling reaction was monitored by ninhydrin color reaction. After washing with MeOH, the resin was dried under vacuum for 2 hours and hereafter the same procedure for cyclation, cleavage and purification (prep-HPLC General procedure, method 1) as for SEQ ID NO: 52 was followed to give the final product SEQ ID NO: 53 (16.8 mg). ESI-MS (M+1): 2016.02 calc. for $C_{98}H_{138}N_{26}O_{17}S_2$: 2015.01, m/z found 1008.5 [M/2+H]+672.6 [M/3+H]+. HPLC analytical method 1, Rt=8.56 min.

Synthesis of the Peptide with SEQ ID NO: 54

To a mixture containing CTC resin (0.2 mmol, sub=1.0 mmol/g, 200 mg) and Fmoc-Met-OH (59.36 mg, 0.16 mmol, 0.8 eq) was added DCM (5 mL), DIEA (4.0 eq) was added dropwise. The resin was mixed 2 hours. MeOH was added (0.5 mL) and mixed for 30 min. The other amino acids were coupled with HBTU (2.85 eq) and DIEA (6.0 eq) for 1 hour. Reactant (S)-10-(((9H-fluoren-9-yl)methoxy)carbonyl)-1-(9H-fluoren-9-yl)-3-oxo-11-(3-(3-((2,2,4,6,7-pentamethyl-2,3-dihydrobenzofuran-5-yl)sulfonyl)guanidino)propyl)-2,7-dioxa-4,10-diazadodecan-12-oic acid (R-03a) (1.5 eq) was coupled with HATU (1.9 eq) and DIEA (3.0 eq) for 1 hour. 20% piperidine in DMF was used for deblocking. The coupling reaction was monitored by ninhydrin color reaction. After washing with MeOH, the resin was dried under vacuum for 2 hours. The resin was treated with 1% TFA/DCM (10 mL) for 5 min, evaporated to give the crude peptide and lyophilized to give the crude product, the crude was added into 100 mL DCM, adjust pH>7 by DIEA, and then HATU (1.5 eq) added. Evaporated to give the crude peptide. The crude was treated with 90% TFA/5% EDT/2.5% Tis/2.5% $H_2O$ for 2 hours. The TFA mixture was precipitated with cold methyl tert-butyl ether (100 mL) and centrifuged (5000 rpm, 2 min). The supernatant was decanted and the precipitate was washed one more time (50 mL). The crude peptide was dried under vacuum for 2 hours, then purified by prep-HPLC (General procedure, method 2) and then lyophilized to give the final product SEQ ID NO: 54 (15.1 mg). ESI-MS (M+1): 2003.03 calc. for $C_{98}H_{139}N_{25}O_{17}S_2$: 2002.03, m/z found 1002.1 [M/2+H]+ 668.3 [M/3+H]+. HPLC analytical method 2, Rt=12.65 min.

Preparation of Intermediate I-14a: (S)-11-(((9H-fluoren-9-yl)methoxy)carbonyl)-2,2-dimethyl-4-oxo-12-(3-(3-((2,2,4,6,7-pentamethyl-2,3-dihydrobenzofuran-5-yl)sulfonyl)guanidino)propyl)-3,8-dioxa-5,11-diazatridecan-13-oic acid To a mixture containing CTC resin (5 mmol, sub=1.0 mmol/g, 5.0 g) and Fmoc-Arg(Pbf)-OH (3.24 g, 5.0 mmol, 1.0 eq) was added DCM (50 mL), DIEA (4.0 eq) was added dropwise. The resin was mixed 2 hours. MeOH was added (5 mL) and mixed for 30 min. The Fmoc protecting peptide resin (9, methyl $N_2$-(((9H-fluoren-9-yl)methoxy)carbonyl)-$N^w$-((2,2,4,6,7-pentamethyl-2,3-dihydrobenzofuran-5-yl)sulfonyl)-L-argininate) CTC resin), was treated with 20% piperidine in DMF for 30 min. After deblocking, the resin was washed with DMF (20 mL) for 5 times. The resin was treated with NsCl (2.0 eq) and DIEA (4.0 eq) in THE (50 mL) for 1 hour, then washed with DMF (5×), the resin was treated with tert-butyl (2-(2-hydroxyethoxy)ethyl)carbamate (2.0 eq) and $PPh_3$ (2.0 eq), DEAD (2.0 eq) was added dropwise in THE (100 mL), the resin was bubbling for 1 hour, the resin was washed with DMF (5×), the resin was treated with sodium benzenethiolate (2.0 eq) in DMF (100 mL) for 1 hour, the resin was washed with DMF (5×), the resin was treated with Fmoc-Cl (2.0 eq) and DIEA (4.0 eq) in DMF (50 mL) for 30 min. The coupling reaction was monitored by ninhydrin color reaction. The resin was washed with DMF (3×) and MeOH (3×), dried under vacuum for 2 hours. Then the resin was treated with 1% TFA/DCM (50 mL) for 5 min, evaporated to give the crude.

Preparation of Intermediate I-15a: $N^2$-(((9H-fluoren-9-yl)methoxy)carbonyl)-$N^2$-(2-(2-aminoethoxy)ethyl)-$N^w$-((2,2,4,6,7-pentamethyl-2,3-dihydrobenzofuran-5-yl)sulfonyl)-L-arginine A solution of I-14a (2.00 g, 2.39 mmol, 1.00 eq) in HCl/EtOAc (4 M, 20 mL) was stirred at 15° C. for 1 h. TLC showed that the reaction was completed. The mixture was filtered and the filtrate was concentrated under reduced pressure to get compound I-15a (900 mg, crude) as a white solid.

Preparation of reactant R-03a: (S)-10-(((9H-fluoren-9-yl)methoxy)carbonyl)-1-(9H-fluoren-9-yl)-3-oxo-11-(3-(3-((2,2,4,6,7-pentamethyl-2,3-dihydrobenzofuran-5-yl)sulfonyl)guanidino)propyl)-2,7-dioxa-4,10-diazadodecan-12-oic acid A mixture of compound I-15a (900 mg, 1.22 mmol, 1.00 eq), Fmoc-OSu (452.70 mg, 1.34 mmol, 1.10 eq), NaHCO$_3$ (408 mg, 1.22 mmol, 4.00 eq) in acetone (5 mL), H$_2$O (5 mL) was stirred at 15° C. for 3 h. TLC showed that the reaction was completed. The acetone was removed under reduced pressure and the residue was diluted with H$_2$O (10 mL), acidified with 1 M HCl to pH=3, extracted with EA (50 mL), washed with H$_2$O (20 mL), brine (20 mL), dried over anhydrous Na$_2$SO$_4$, concentrated under reduced pressure. The residue was purified by silica gel column (DCM:MeCOH=20:1) to obtain compound R-03a (800 mg, 54.75% yield) as a white solid. ESI-MS (M+1): 958.4 found for $C_{53}H_{59}N_5O_{10}S$: 957.4. LCMS procedure as defined above.

Biological Tests

1. Preparation of the Recombinant Proteins

Plasmid pET20b FOXP3-His was generated to produce the human FOXP3 tagged with 6 histidines at the C terminus of the protein. Briefly, plasmid pDEST15-FOXP3 (provided by Dr. Casal, Madrid, Spain) was used as template to amplify FOXP3 by PCR using the primers Upper FOXP3 NdeI catatgcccaaccccaggc (SEQ ID NO: 55) and Lower FOXP3 gcggccgcggggccaggtgtagggtt (SEQ ID NO: 56). The resulting fragment was subcloned in pET20b at NdeI and NotI sites. pET45b His-Runx1 was obtained by PCR of activated human CD4 T cells obtained from healthy volunteers (after the signature of an informed consent) using the primers Upper Runx1 atgcgtatccccgtagatg (SEQ ID NO: 57) and Lower Runx1 gtagggcctccacacggcctc (SEQ ID NO: 58) and the fragment was cloned in pcDNA3.1. Then, pET45b and pcDNA3.1-Runx1 were digested with BamHI and NotI and ligated to obtain pET45b-Runx1. Plasmids were used to transform BL21 cells (DE3; Novagen, Schwalbach, Germany) for the expression of the recombinant protein. The transformed BL21 cells were grown in LB medium at 37° C. (1 liter of final culture medium) (with ampicilin 0.1 mg/ml). Once the OD of the culture was between 0.5 and 1.0, IPTG (0.4 mM, final concentration) was added. Bacteria were then cultured overnight in agitation and centrifuged for 10 min at 8000 rpm. Cell pellet was then resuspended in 4 ml Tris-HCl 0.1 M and frozen at −80° C. Cell pellet was then thawed and incubated with lisozyme (25 KU) and a protease inhibitor cocktail for 15 min at 30° C. before cell lysis induced with a French-press. The resultant pool was then centrifuged during 20 min at 11.000 rpm). The recombinant protein was purified from the soluble fraction of French-press cell extracts by affinity chromatography (Histrap, Pharmacia) following manufacturer's instructions and using an FPLC platform (AKTA, Pharmacia). Plasmid pDEST15-FOXP3 encoding the fusion protein GST-FOXP3 (GST fused to the isoform A from human FOXP3 gene), was transformed into BL21 cells for the expression of the recombinant protein. GST-FOXP3 protein was purified from the soluble fraction of cell extracts obtained, as described above, by affinity chromatography (GSTrap; Amersham, Piscataway, N.J.) using a fast protein liquid chromatography platform (AKTA; Amersham) following manufacturer's instructions. The eluted proteins were desalted using Hitrap desalting columns (Pharmacia) and analyzed by SDS-PAGE using Coomassie blue (Bio-Safe Coomassie reagent; Bio-Rad, Hercules, Calif.) and by Western blot.

2. Biomolecular Interaction Analysis by Surface Plasmon Resonance and by Alphascreen Technology Screening of peptide binding to FOXP3 was performed by surface plasmon resonance (SPR) using ProteOn XPR36 (Bio-Rad, Hercules Calif., USA) optical biosensor. Recombinant protein FOXP3-6His was produced and purified from E-coli as disclosed in previous section and was immobilized covalently onto a GLM sensor chip (176-5012, Bio-Rad) using sulfo-NHS and EDC (Bio-Rad) coupling reagents and the manufacturer's instructions. After protein immobilization, chip surface was treated with ethanolamine to deactivate the excess of reactive esters.

Individual solutions of the peptides to be tested (1-20 μM) were injected by triplicate in running buffer (Phosphate buffered saline, 0.005% (v/v) Tween 20, pH 7.4) at a flow of 30 μl/min. The interspot signal (obtained in the chip surface not immobilized with protein) was used as reference.

The results are summarized in Table 6 below as the ratio Peptide of the invention/p60. It has been described that dimerization of FOXP3 is required for its function as a transcriptional regulator. Moreover, interaction between FOXP3 and the transcription factor Runx1, is crucially required for normal hematopoiesis including thymic T-cell development, but also for Treg suppressor activity (Reviewed in Lozano et al, Front Oncol. 2013, 3:294). Both activities are mediated by the intermediate region of Foxp3, which is the area of interaction between P60 and Foxp3. Thus, we studied the effect of P60 and their mutants on the FOXP3/Runx1 heterodimerization, as well as FOXP3/FOXP3 homodimerization by Alphascreen technology according to the manufacturer's instructions (Perkin Elmer, Benelux). AlphaScreen™ is a bead-based technology that is designed to measure the proximity of donor and acceptor beads conjugated to biomolecules of interest.

To measure FOXP3/FOXP3 homodimerization, recombinant Foxp3 was expressed with a Histine tag as disclosed in section (1) above, and captured by Nickel chelate Acceptor beads (Cat. AL108 Perkin Elmer) following manufacturer's instructions. The other version of recombinant FOXP3, expressing a GST tag (prepared as disclosed in section (1) above), was captured by Glutathione Donor beads (Perkin Elmer Cat. 6765300), following manufacturer's instructions. When the two proteins interacted together, the Donor and Acceptor beads come into proximity. Excitation of the Donor beads results in emission of light from the Acceptor beads. The signal generated was proportional to the amount of proteins. Reactions were performed in a 40 μl final volume in 96-well Optiwell microtiter plates (Perkin Elmer Cat. 6005560). The reaction buffer contained 20 mM HEPES, pH 7.9, 200 mM KCl, 1 mM MgCl2 and 0.05% BSA.

To measure Foxp3-Runx1 interactions, Foxp3-GST and NFAT-6His proteins were used.

Recombinant Runx1 expressed in E. coli with a hexa-histidine tag (obtained as disclosed in section (1) above) was captured by nickel chelate acceptor beads following manufacturer's instructions, whereas the recombinant FOXP3 expressed with a GST tag was captured by glutathione donor beads (Perkin Elmer) following manufacturer's instructions. His-tagged Runx1 (46 nM final concentration) was incubated with 100 nM GST-FOXP3 and the peptides to be tested (added at different concentrations from 1 to 100 μM) for 1 h at room temperature.

Subsequently, nickel chelate-coated acceptor beads and glutathione donor beads were added to a final concentration of 20 µg/ml of each bead. Proteins and beads were incubated for 1 h at room temperature to allow association to occur.

GST-tagged FOXP3 (40 nM) and His-tagged FOXP3 (400 nM) were co-cultured in the presence or absence of indicated peptides (20 µM) for 1 h. Then, donor and acceptor beads were added as described above and incubated for 2 h.

Exposure of the reaction to direct light was avoided as much as possible and the emission of light from the acceptor beads was measured in the EnVision plate reader after the indicated incubation period (Perkin Elmer, Benelux). The data provided in tables below provides the fold change, i.e., the ratio of binding units of the tested peptide with respect to p60 (SEQ ID NO: 1)

TABLE 6

Binding to FoxP3 (FOXP3/FOXP3 homodimerization)

| SEQ. ID. NO. | Binding to Foxp3 Ratio binding Peptide/p60 (fold change) |
|---|---|
| 1 | 1, 0 |
| 2 | 2, 4 |
| 3 | 2, 8 |
| 4 | 4, 2 |
| 5 | 4, 1 |
| 6 | 3, 3 |
| 7 | 1, 4 |
| 8 | 1, 4 |
| 9 | 1, 4 |
| 11 | 1, 4 |
| 12 | 2, 2 |
| 13 | 3, 2 |
| 14 | 3, 6 |
| 15 | 1, 1 |
| 16 | 3, 7 |
| 17 | 3, 3 |
| 18 | 1, 9 |
| 19 | 1, 1 |
| 20 | 3, 7 |
| 21 | 3, 2 |
| 22 | 2, 4 |
| 23 | 1, 3 |
| 24 | 4, 6 |
| 25 | 4, 0 |
| 28 | 2, 6 |
| 29 | 1, 4 |
| 30 | 1, 1 |
| 31 | 2, 8 |
| 32 | 1, 4 |
| 33 | 1, 3 |
| 35 | 1, 3 |
| 37 | 4, 1 |
| 38 | 1, 1 |
| 39 | 3, 3 |
| 40 | 2, 2 |
| 41 | 3, 7 |
| 42 | 4, 1 |
| 43 | 4, 9 |
| 44 | 3, 0 |
| 45 | 8, 0 |
| 46 | 2, 7 |
| 47 | 1, 7 |
| 48 | 2, 5 |
| 49 | 5, 0 |
| 50 | 21, 4 |
| 51 | 21, 4 |
| 52 | 13, 0 |
| 53 | 2, 2 |
| 54 | 25, 3 |

TABLE 7

FoxP3 inhibition (FOXP3/RunX1 heterodimerization)

| SEQ. ID. NO. | Foxp3-Runx1 Inhibition % inhibition (100 µM) |
|---|---|
| 1 | 54, 5 |
| 5 | 76, 0 |
| 14 | 80 (2, 5 µM) |
| 15 | 55, 6 |
| 19 | 74, 7 |
| 30 | 73, 9 |
| 46 | 95 (2, 5 µM) |
| 47 | 75 (2, 5 µM) |
| 48 | 70 (2, 5 µM) |
| 50 | 60 (2, 5 µM) |

3. In Vitro Treg Suppression Assay
3.1. Purification of Murine Tconv/Treg

Spleen was harvested from BALB/c mice (Harlan Laboratories) and homogenized with a 1-ml syringe through a 100-µm cell strainer into a 50-ml conical tube and rinsed two times with PBS (Calcium free) to recover all cells. Cell homogenate was centrifuged at 300×g for 10 min and resuspended homogenate in 1 ml ACK Lysis buffer solution per spleen. Gently swirled for 2 min and then the reaction was quenched by adding 12 ml of PBS.

Cells were centrifuged at 300×g for 10 min and purification of CD25− and CD25+ cells was carried out using magnetic beads (Miltenyi, CD25 microbead kit MOUSE, Ref 130-091-072)), following manufacturer's instructions. After labelling the cells, they were purified using AutomacsPro device following manufacturer's instructions. Negative fraction corresponded to CD25− cells, which was used as effector Tconv cells. Positive fraction corresponded to CD25+ T cells that was used as Treg cells. Flow cytometry using anti-CD25-APC labeled and anti-CD4-FITC labelled antibodies was used to confirm the purity of isolated cells. Foxp3 expression was analyzed using the anti-Foxp3 staining antibody labelled with APC according to manufacturer's instructions (eBioscience).

Purified cells were washed, resuspended in culture medium and diluted in T-cell culture medium (RPMI 1640, supplemented with 10% Fetal bovine serum and antibiotics) at a concentration of $2 \times 10^5$/ml (for Tregs) and $2 \times 10^6$/ml (for Tconv), for the assay (See below)

3.2. Treg Suppressor Assay.

The first in vitro assays to measure regulatory T-cell (Treg) function were described by two groups over a decade ago. The observation that a CD25+ T-cell population possessed regulatory activity enabled isolation of natural Tregs cells from mice and humans. With this knowledge, it was shown that CD4+CD25+ T cells could potently suppress the proliferation of activated CD4+CD25− and CD8+ T cells when the populations were cocultured in vitro. The following protocol describes a basic type of in vitro Treg suppression assay where Treg function is measured in the absence of antigen-presenting cells (APCs). In this protocol, activation is mediated by anti-CD3 antibodies and includes only two cell types, the target Tconv and Tregs. In this protocol, the experiment is setup in a 96-well round-bottom plate in a total volume of 200 µl. All reagents are prepared at four times their desired final concentration and added to assay in 50 µl such that the total volume is 200 µl, thus obtaining the desired final concentration of reactives. Purified Tregs and Tconv prepared as described above were diluted and adjusted in T-cell culture medium to $2 \times 10^5$/ml and $2 \times 10^6$/ ml, respectively. In round-bottom 96-well plate, Tregs and Tconv were added in 50 μl of culture media each (RPMI 1640, supplemented with 10% Fetal bovine serum, and antibiotics). Anti-CD3 antibody was added in 50 μl (final concentration will be 2.5 μg/ml) as a stimulus to induce T cell proliferation. 50 μL of each one of the peptides to be tested were added in the corresponding wells at a concentration of 100 μM and those which provided the best results were tested again at lower concentrations to determine the IC$_{50}$ value. The final volume was 200 μl in all wells. Tconv alone, Tconv plus anti-CD3, Tconv+anti-CD3+Treg or Tconv+anti-CD3+Treg+peptides were tested by quadruplicate. Tconv plus anti-CD3 with no Treg was used to determine maximum proliferation of Tconv whereas Tconv+anti-CD3+Treg was used to determine Treg inhibition. Plates were incubated at 37° C., 5% CO$_2$ for 72 h and then pulsed with 0.1 μCi [$^3$H$_1$]-thymidine (in 25 μl of culture medium per well). After 8 h of incubation, cell cultures were harvested with a cell harvester (Perkin Elmer) and using unifilter plates. Plates were then dried at 50° C., and scintillation reagent (25 μl)(Microscint, Perkin Elmer) was added to each well. Counts per minute (cpm) were determined with a direct beta counter (TopCount, Perkin Elmer).

The results of in vitro Treg suppression assays are most commonly reported as cpm when [$^3$H]-thymidine is incorporated into proliferating cells. Wells containing both Tconv and Tregs will have lower cpm than wells containing Tconv cells alone because coculture of Tregs with Tconv cells reduces the proliferative capacity of Tconv cells. In addition, as the ratio of Tconv cells to Treg increases, the cpm values will increase proportionately. As Tregs proliferate very poorly in vitro, they do not contribute significantly to cpm values. Due to day to day or sample to sample variability, experimental replicates will often not result in identical cpm values. For this reason, a percent suppression (% supp) calculation assay can be calculated in order to depict many experiments with slightly (or significantly) different cpm values. Percent suppression is calculated using the following formula: ((cpm of Tconv cells alone–cpm of Tconv cells treated with Treg)/cpm of Tconv cells alone)*100. Alternatively, a representative experiment can be depicted with cpm. It is expected that if a peptide is able to inhibit Treg activity, a restoration on Tcell proliferation of Tconv in response to anti-CD3 stimulation should be expected. Thus, calculation of the % of inhibition of Treg activity using the following formula: 100*((cpm of Tconv cells plus anti-CD3 plus Treg plus peptide)–(cpm of Tconv cells plus anti-CD3 plus Treg))/((cpm of Tconv cells plus anti-CD3)–(cpm of Tconv cells plus anti-CD3 plus Treg)) was performed. For screening purposes, most of the peptides were tested at 100 μM. In some cases, optimized peptides were tested at different concentration to calculate the peptide concentration able to inhibit 50% of Treg activity (IC$_{50}$)

The results are summarized in Tables 8 to 10 below:

TABLE 8

| SEQ. ID. NO. | IC$_{50}$ (μM) |
| --- | --- |
| 1 | 38, 3 |
| 3 | 27, 2 |
| 4 | 13, 4 |
| 13 | 12, 5 |
| 14 | 12, 5 |
| 41 | 1, 9 |
| 45 | 3, 0 |

TABLE 8-continued

| SEQ. ID. NO. | IC$_{50}$ (μM) |
| --- | --- |
| 46 | 12, 5 |
| 47 | 35, 0 |
| 48 | 20, 0 |
| 50 | 0, 8 |

From the data provided in Table 8 in can be concluded that an inhibitory effect on Treg activity is achieved, remarkably reducing the amount of the peptide to be added to inhibit in a 50% the Treg activity (in comparison with the one used for p60).

TABLE 9

Treg inhibition - % inhibition (100 μM)

| SEQ. ID. NO. | % inhibition (100 μM) |
| --- | --- |
| 1 | 115, 6 |
| 3 | |
| 4 | |
| 5 | 347, 1 |
| 9 | 210, 0 |
| 19 | 159, 5 |
| 30 | 170, 3 |

From the data provided in Table 9 in can be concluded that an increased inhibitory effect on Treg activity is achieved by peptides of the invention compared to p60.

TABLE 10

Dimerization inhibition results

| SEQ. ID. NO. | % inhibition (100 μM)* |
| --- | --- |
| 1 | 59, 7 |
| 2 | 80 (20 μM) |
| 5 | 74, 3 |
| 14 | 90 (20 μM) |
| 19 | 89, 0 |
| 30 | 81, 3 |
| 46 | 90 (20 μM) |

4. In Vivo Experiments 4.1 Tumor Rejection Experiments.

For tumor rejection experiments, Hepa-129 cells (10$^6$ cells/mouse), were injected subcutaneously (sc) in C$_3$H/HeN mice (n=6). Ten days later, when the tumor reached 5 mm in diameter, mice were randomly divided into different experimental groups. A group of mice were treated i.p. with anti-PD1 antibodies (BE0146, BioXcell) (50 μg/mouse). Antibody administration was repeated one week after this first administration. A group of mice treated with anti-PD1 also received the cyclic peptide SEQ ID NO: 50 from days 10 to 20 (50 μg/mice/day). Tumor size, presented as the average of two perpendicular diameters (millimeters), was measured at regular intervals. Mice were sacrificed when the mean tumor diameter was greater than 20 mm. Mice were housed in appropriated animal care facilities during the experimental period and handled following the international guidelines required for experimentation with animals. The experiments were approved by institutional ethical committee.

The results are provided in FIGS. 1 and 2: anti-PD1 administration at the tested doses did not show a significant antitumor effect. But importantly, when anti-PD1 antibodies administration was combined with the administration of the peptide of sequence SEQ ID NO: 50, a remarkable antitumor activity was detected.

For anti-tumor vaccination experiments, BALB/c animals immunized with 50 nanomol/mice of peptide AH1 emulsified in incomplete Freund adjuvant (IFA) (Casares et al., 2010, supra), were treated intraperitoneally with 10 nanomol/mice of the indicated Treg inhibitory peptide SEQ ID NO: 51 of the invention or with saline daily during 10 days. At day 10, mice were injected s.c. with $10^6$ CT26 tumor cells. Tumor size was monitored twice a week with a caliper and it was expressed according to the formula V=(length× width2)/2. Mice were sacrificed when tumor size reached a volume greater than 4 $cm^3$.

The results are provided in FIG. 3: the peptide of the invention shows a remarkably effect in preventing the growth of colon cancer cells. In fact, at day 30 after injection of CT26 tumor cells, the peptide of the invention prevents the growth of tumor, p60 was not efficient, giving rise to a tumor volume of about 2000 $mm^3$.

5. Statistical Analysis

Normality was assessed with Shapiro-Wilk W test. Statistical analyses were performed using parametric (Student's t test and one-way ANOVA) and non-parametric (Kruskal-Wallis and Mann-Whitney U) tests. For all tests a p value<0.05 was considered statistically significant. Descriptive data for continuous variables are reported as means±SEM. GraphPad Prism for Windows was used for statistical analysis.

6. Human and Mouse Liver Microsomal Stability

The data collected were analyzed to calculate a half-life ($t_{1/2}$, min) for tested peptides at a final concentration of 1 µM. Briefly, 5 µL of stock solution of tested peptide (10 mM) were diluted in 495 µL of 1:1 Methanol/Water (final concentration of 100 µM, 50% MeOH). Then, 50 µL of this intermediate solution were diluted in 450 µL of 100 mM potassium phosphate buffer to a concentration of 10 µM (working solution, 5% MeOH). The NADPH regenerating system contains β-Nicotinamide adenine dinucleotide phosphate (Sigma, Cat. #$N_{0505}$), Isocitric acid (Sigma, Cat. #11252) and Isocitric dehydrogenase (Sigma, Cat. #12002) at a final concentration of 1 unit/mL at incubation.

Human liver microsomes were obtained from BD Gentest (Cat. #452117) and mouse liver microsomes from Xenotech (Cat. #M1000), to a final concentration of 0.7 mg protein/ mL. A volume of 10 µL of peptide solution and 80 µL of microsome solution were added to a 96-well plate and incubated for 10 min at 37° C. The reaction was started by the addition of 10 µL of NADPH regenerating system and stopped by the addition of 300 µL of stop solution (ACN at 4° C., including 100 ng/mL Tolbutamide and 100 ng/mL of Labetalol as internal standard) at different incubation times (0, 5, 10, 20, 30 and 60 min). Concentrations of test compound were quantified by LC-MS/MS methodologies (Shimadzu LC 20-AD/API4000) using peak area ratio of analyte/internal standard and the percent loss of parent compound was calculated under each time point to determine the half-life.

Tables 11 and 12 show the estimated half-life ($t_{1/2}$, min) and percentage (%) of peptide remaining after 20 and 60 min of incubation with human liver microsomes (HLM) and mouse liver microsomes (MLM).

TABLE 11

| SEQ ID NO | Human Liver Microsomes | | |
|---|---|---|---|
| | $t_{1/2}$ (min) | % Remaining after 20 min | % Remaining after 60 min |
| p60 (1) | <2.5 | 0 | 0 |
| 3 | <2.5 | 0 | 0 |
| 50 | 5.30 | 6.20 | 0 |
| 51 | 61.7 | 48.7 | 46.1 |
| 52 | 41.4 | 76.9 | 40.1 |
| 53 | 11.1 | 32.9 | 2.8 |
| 54 | 18.4 | 55.7 | 11.0 |

TABLE 12

| SEQ ID NO | Mouse Liver Microsomes | | |
|---|---|---|---|
| | $t_{1/2}$ (min) | % Remaining after 20 min | % Remaining after 60 min |
| p60 (1) | <2.5 | 0 | 0 |
| 3 | <2.5 | 0 | 0 |
| 50 | 8 | 12 | 0 |
| 51 | 63.8 | 62.7 | 47.7 |
| 52 | 46.9 | 98.9 | 48.0 |
| 53 | 12.3 | 57.0 | 3.7 |
| 54 | 30.9 | 97.3 | 30.1 |

Cyclic peptides of the invention have a remarkably increased stability compared to p60.

CITATION LIST

Altschul et al., "Basic local alignment search tool", 1990, J. Mol. Biol, v. 215, pages 403-410;

Casares N. et al., "A peptide inhibitor of FOXP3 impairs regulatory T cell activity and improves vaccine efficacy in mice", 2010, J. Immunol., vol. 185(9), pages 5150-5159;

Copolovici D. M. et al., "Cell-Penetrating Peptides: Design, Synthesis, and Applications", 2014, ACS Nano, 8 (3), pp 1972-1994;

Ford K. G. et al., Protein transduction: an alternative to genetic intervention? Gene Therapy, 2001; 8:1-4;

Frassanito M. A. et al. "Myeloma cells act as tolerogenic antigen-presenting cells and induce regulatory T cells in vitro", 2015, Eur J Haematol., vol. 95(1), pages 65-74

Higgins et al., "CLUSTAL V: improved software for multiple sequence alignment", 1992, CABIOS, 8(2), pages 189-191;

Huibregtse, I. L. et al., "Induction of ovalbumin-specific tolerance by oral administration of *Lactococcus lactis* secreting ovalbumin", 2007, Gastroenterology, vol. 133, pages 517-528;

Joosten S. A. et al., "Human CD4 and CD8 regulatory T cells in infectious diseases and vaccination", 2008, Hum. Immunol., vol. 69(11), pages 760-70;

Lozano T. et al., "Searching for the Achilles Heel of FOXP3", 2013, Front. Oncol., vol. 3, page 294;

Khalil D N et al., "The New Era of Cancer Immunotherapy: Manipulating T-Cell Activity to Overcome Malignancy" Advances in Cancer Research, 2015, vol. 128, pages 1-68;

Nishikawa H. et al., "Regulatory T cells in tumor immunity", 2010, Int. J. Cancer, vol. 127, pages 759-767;

Ono M. et al., "Foxp3 controls regulatory T-cell function by interacting with AML1/Runx1", 2007, Nature, vol. 446 (7136), pages 685-689;

Sambrook et al., "Molecular cloning, a Laboratory Manual", 4th ed., Cold Spring Harbor Laboratory Press, N.Y., 2012 Vol 1-3) Chapter 3 from Vol 1: Cloning and Transformation with Plasmid Vectors;

Son X. et al., "Structural and biological features of FOXP3 dimerization relevant to regulatory T cell function", 2012, Cell Rep., vol. 1(6), pages 665-675;

Tandrup Schmidt S. et al., "Liposome-Based Adjuvants for Subunit Vaccines: Formulation Strategies for Subunit Antigens and Immunostimulators", Pharmaceutics, 2016 Mar. 10; 8(1); and Williams L. M. and Rudensky A. Y., "Maintenance of the Foxp3-dependent developmental program in mature regulatory T cells requires continued expression of Foxp3", 2007, Nat. Immunol., vol. 8, pages 277-284.

The invention claimed is:

1. A nucleic acid encoding a peptide, wherein the peptide is selected from the group consisting of:
   (a) a peptide represented by Arg-X1-X2-Gln-X3-Phe-Arg-X4-Met-Trp-X5-Phe-Phe-Ala-Met        (I)

wherein:
   $X_1$ and $X_3$ are the same or different and represent D- or L-non polar amino acids; and
   $X_2$, $X_4$, and $X_5$ represent amino acid residues, the same or different;
   (b) a peptide having at least 80% of sequence identity with the peptide defined in (a) and which maintains the ability to bind FoxP3 and inhibit FoxP3 activity in vitro and/or in vivo; and
   (c) a fragment of the peptide defined in (a) or in (b), wherein said fragment comprises:
   a portion of at least 11 consecutive amino acids of the peptide defined in (a) or in (b), wherein the fragment further comprises $X_1$ and $X_2$ as defined above in (a); and wherein the peptide maintains the ability to bind FoxP3 and inhibit FoxP3 activity in vitro and/or in vivo.

2. The nucleic acid of claim 1, which further comprises a nucleic acid codifying a cell-penetrating peptide with the capacity of internalize the peptide in a cell.

3. The nucleic acid of claim 1 which is operatively bound to an expression regulatory sequence.

4. A vector comprising the nucleic acid of claim 1.

5. A host cell comprising the nucleic acid of claim 1.

6. The nucleic acid of claim 2 is operatively bound to an expression regulatory sequence.

7. A vector comprising the nucleic acid of claim 2.

8. A host cell comprising the nucleic acid of claim 2.

9. A host cell comprising the vector of claim 4.

10. The nucleic acid of claim 1, which encodes a peptide selected from the group consisting of the peptides encoded by a sequence selected from the group consisting of SEQ ID NOS: 41-43, 45, and 50-54.

* * * * *

SEQUENCE LISTING

```
<160> NUMBER OF SEQ ID NOS: 58

<210> SEQ ID NO 1
<211> LENGTH: 15
<212> TYPE: PRT
<213> ORGANISM: Artificial Sequence
<220> FEATURE:
<223> OTHER INFORMATION: peptide p60

<400> SEQUENCE: 1

Arg Asp Phe Gln Ser Phe Arg Lys Met Trp Pro Phe Phe Ala Met
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 2

Arg Asp Phe Gln Ser Phe Arg Lys Met Trp Pro Phe Phe Ala Met
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<222> LOCATION: (2)..(2)
<223> OTHER INFORMATION: D-Asp

<400> SEQUENCE: 3

Arg Asp Phe Gln Ser Phe Arg Lys Met Trp Pro Phe Phe Ala
1               5                   10

<210> SEQ ID NO 4
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: D-Asp
<220> FEATURE:
```

```
<221> NAME/KEY: MOD_RES
<222> LOCATION: (15)..(15)
<223> OTHER INFORMATION: AMIDATION

<400> SEQUENCE: 4

Arg Asp Phe Gln Ser Phe Arg Lys Met Trp Pro Phe Phe Ala Met
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: PEPTIDE

<400> SEQUENCE: 5

Arg Ala Phe Gln Ser Phe Arg Lys Met Trp Pro Phe Phe Ala Met
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<222> LOCATION: (2)..(2)
<223> OTHER INFORMATION: D-Ala

<400> SEQUENCE: 6

Arg Ala Phe Gln Ser Phe Arg Lys Met Trp Pro Phe Phe Ala Met
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: PEPTIDE

<400> SEQUENCE: 7

Arg Ser Phe Gln Ser Phe Arg Lys Met Trp Pro Phe Phe Ala Met
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: PEPTIDE

<400> SEQUENCE: 8

Arg Tyr Phe Gln Ser Phe Arg Lys Met Trp Pro Phe Phe Ala Met
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: PEPTIDE

<400> SEQUENCE: 9

Arg Trp Phe Gln Ser Phe Arg Lys Met Trp Pro Phe Phe Ala Met
1               5                   10                  15
```

```
<210> SEQ ID NO 10
<211> LENGTH: 15
<212> TYPE: PRT
<213> ORGANISM: Artificial Sequence
<220> FEATURE:
<223> OTHER INFORMATION: PEPTIDE

<400> SEQUENCE: 10

Arg Glu Phe Gln Ser Phe Arg Lys Met Trp Pro Phe Phe Ala Met
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: PEPTIDE

<400> SEQUENCE: 11

Arg Asn Phe Gln Ser Phe Arg Lys Met Trp Pro Phe Phe Ala Met
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: PEPTIDE

<400> SEQUENCE: 12

Arg Lys Phe Gln Ser Phe Arg Lys Met Trp Pro Phe Phe Ala Met
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 13

Arg Ala Phe Gln Ser Phe Arg Lys Met Trp Pro Phe Phe Ala Met
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: D-Ala
<220> FEATURE:
<221> NAME/KEY: MOD_RES
<222> LOCATION: (15)..(15)
<223> OTHER INFORMATION: AMIDATION
```

```
<400> SEQUENCE: 14

Arg Ala Phe Gln Ser Phe Arg Lys Met Trp Pro Phe Phe Ala Met
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: PEPTIDE

<400> SEQUENCE: 15

Arg Asp Ala Gln Ser Phe Arg Lys Met Trp Pro Phe Phe Ala Met
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: PEPTIDE

<400> SEQUENCE: 16

Arg Asp Trp Gln Ser Phe Arg Lys Met Trp Pro Phe Phe Ala Met
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: PEPTIDE

<400> SEQUENCE: 17

Arg Asp Tyr Gln Ser Phe Arg Lys Met Trp Pro Phe Phe Ala Met
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: PEPTIDE

<400> SEQUENCE: 18

Arg Asp Leu Gln Ser Phe Arg Lys Met Trp Pro Phe Phe Ala Met
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: PEPTIDE

<400> SEQUENCE: 19

Arg Asp Phe Gln Ala Phe Arg Lys Met Trp Pro Phe Phe Ala Met
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: PEPTIDE

<400> SEQUENCE: 20
```

```
Arg Asp Phe Gln Arg Phe Arg Lys Met Trp Pro Phe Phe Ala Met
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: PEPTIDE

<400> SEQUENCE: 21

Arg Asp Phe Gln Asn Phe Arg Lys Met Trp Pro Phe Phe Ala Met
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: PEPTIDE

<400> SEQUENCE: 22

Arg Asp Phe Gln Trp Phe Arg Lys Met Trp Pro Phe Phe Ala Met
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: PEPTIDE

<400> SEQUENCE: 23

Arg Asp Phe Gln Glu Phe Arg Lys Met Trp Pro Phe Phe Ala Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: PEPTIDE

<400> SEQUENCE: 24

Arg Asp Phe Gln Tyr Phe Arg Lys Met Trp Pro Phe Phe Ala Met
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: PEPTIDE

<400> SEQUENCE: 25

Arg Asp Phe Gln Lys Phe Arg Lys Met Trp Pro Phe Phe Ala Met
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: PEPTIDE

<400> SEQUENCE: 26
```

```
Arg Asp Phe Gln Ser Phe Arg Ala Met Trp Pro Phe Phe Ala Met
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: PEPTIDE

<400> SEQUENCE: 27

Arg Asp Phe Gln Ser Phe Arg Glu Met Trp Pro Phe Phe Ala Met
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: PEPTIDE

<400> SEQUENCE: 28

Arg Asp Phe Gln Ser Phe Arg His Met Trp Pro Phe Phe Ala Met
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: PEPTIDE

<400> SEQUENCE: 29

Arg Asp Phe Gln Ser Phe Arg Arg Met Trp Pro Phe Phe Ala Met
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: PEPTIDE

<400> SEQUENCE: 30

Arg Asp Phe Gln Ser Phe Arg Lys Met Trp Ala Phe Phe Ala Met
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: PEPTIDE

<400> SEQUENCE: 31

Arg Asp Phe Gln Ser Phe Arg Lys Met Trp Arg Phe Phe Ala Met
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: PEPTIDE

<400> SEQUENCE: 32

Arg Asp Phe Gln Ser Phe Arg Lys Met Trp Asn Phe Phe Ala Met
```

<210> SEQ ID NO 33
<211> LENGTH: 15
<212> TYPE: PRT
<213> ORGANISM: Artificial Sequence
<220> FEATURE:
<223> OTHER INFORMATION: PEPTIDE

<400> SEQUENCE: 33

Arg Asp Phe Gln Ser Phe Arg Lys Met Trp Val Phe Phe Ala Met
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: PEPTIDE

<400> SEQUENCE: 34

Arg Asp Phe Gln Ser Phe Arg Lys Met Trp Glu Phe Phe Ala Met
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: PEPTIDE

<400> SEQUENCE: 35

Arg Asp Phe Gln Ser Phe Arg Lys Met Trp Tyr Phe Phe Ala Met
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: PEPTIDE

<400> SEQUENCE: 36

Arg Asp Phe Gln Ser Phe Arg Lys Met Trp Gly Phe Phe Ala Met
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: PEPTIDE

<400> SEQUENCE: 37

Arg Asp Phe Gln Ser Phe Arg Lys Met Trp Lys Phe Phe Ala Met
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (15)..(15)
<223> OTHER INFORMATION: AMIDATION
<220> FEATURE:
<221> NAME/KEY: misc_feature
<222> LOCATION: (15)..(15)
<223> OTHER INFORMATION: D-Met

<400> SEQUENCE: 38

Arg Asp Phe Gln Ser Phe Arg Lys Met Trp Ala Phe Phe Ala Met
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (5)..(5)
<223> OTHER INFORMATION: D-Ala
<220> FEATURE:
<221> NAME/KEY: MOD_RES
<222> LOCATION: (15)..(15)
<223> OTHER INFORMATION: AMIDATION

<400> SEQUENCE: 39

Arg Asp Phe Gln Ala Phe Arg Lys Met Trp Pro Phe Phe Ala Met
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (11)..(11)
<223> OTHER INFORMATION: D-Ala
<220> FEATURE:
<221> NAME/KEY: MOD_RES
<222> LOCATION: (15)..(15)
<223> OTHER INFORMATION: AMIDATION

<400> SEQUENCE: 40

Arg Asp Phe Gln Ser Phe Arg Lys Met Trp Ala Phe Phe Ala Met
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION
```

```
<400> SEQUENCE: 41

Arg Ala Phe Gln Ala Phe Arg Lys Met Trp Pro Phe Phe Ala Met
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: PEPTIDE

<400> SEQUENCE: 42

Arg Ala Phe Gln Ala Phe Arg Lys Met Trp Pro Phe Phe Ala Met
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: D-Ala
<220> FEATURE:
<221> NAME/KEY: misc_feature
<222> LOCATION: (5)..(5)
<223> OTHER INFORMATION: D-Ala
<220> FEATURE:
<221> NAME/KEY: MOD_RES
<222> LOCATION: (15)..(15)
<223> OTHER INFORMATION: AMIDATION

<400> SEQUENCE: 43

Arg Ala Phe Gln Ala Phe Arg Lys Met Trp Pro Phe Phe Ala Met
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 44

Arg Ala Phe Gln Ser Phe Arg Lys Met Trp Ala Phe Phe Ala Met
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (15)..(15)
<223> OTHER INFORMATION: AMIDATION

<400> SEQUENCE: 45

Arg Ala Phe Gln Ala Phe Arg Lys Met Trp Ala Phe Phe Ala Met
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<222> LOCATION: (1)..(1)
<223> OTHER INFORMATION: D-Arg

<400> SEQUENCE: 46

Arg Ala Phe Gln Ser Phe Arg Lys Met Trp Pro Phe Phe Ala Met
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<222> LOCATION: (15)..(15)
<223> OTHER INFORMATION: D-Met

<400> SEQUENCE: 47

Arg Ala Phe Gln Ser Phe Arg Lys Met Trp Pro Phe Phe Ala Met
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<222> LOCATION: (1)..(1)
<223> OTHER INFORMATION: D-Arg
<220> FEATURE:
<221> NAME/KEY: misc_feature
<222> LOCATION: (15)..(15)
<223> OTHER INFORMATION: D-Met

<400> SEQUENCE: 48

Arg Ala Phe Gln Ser Phe Arg Lys Met Trp Pro Phe Phe Ala Met
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a linker birradical which is
      -C(=O)-

<400> SEQUENCE: 49
```

Arg Asp Phe Gln Ser Phe Arg Lys Met Trp Pro Phe Phe Ala Met
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a linker birradical which is
      -C(=O)-

<400> SEQUENCE: 50

Arg Ala Phe Gln Ala Phe Arg Lys Met Trp Pro Phe Phe Ala Met
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a birradical linker which is
      -C(=O)-
<220> FEATURE:
<221> NAME/KEY: misc_feature
<222> LOCATION: (2)..(2)
<223> OTHER INFORMATION: D-Ala

<400> SEQUENCE: 51

Arg Ala Phe Gln Ala Phe Arg Lys Met Trp Pro Phe Phe Ala Met
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a birradical linker which is
      -(CH2)3-NH-CO-
<220> FEATURE:
<221> NAME/KEY: misc_feature
<222> LOCATION: (2)..(2)
<223> OTHER INFORMATION: D-Ala

<400> SEQUENCE: 52

Arg Ala Phe Gln Ala Phe Arg Lys Met Trp Pro Phe Phe Ala Met
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a birradical which is
      -(CH2)2-NH-C(=O)-(CH2)-NH-C(=O)-
<220> FEATURE:
<221> NAME/KEY: misc_feature
<222> LOCATION: (2)..(2)
<223> OTHER INFORMATION: D-Ala

<400> SEQUENCE: 53

```
Arg Ala Phe Gln Ala Phe Arg Lys Met Trp Pro Phe Phe Ala Met
1               5                   10                  15
```

<210> SEQ ID NO 54
<211> LENGTH: 15
<212> TYPE: PRT
<213> ORGANISM: Artificial Sequence
<220> FEATURE:
<223> OTHER INFORMATION: PEPTIDE
<220> FEATURE:
<221> NAME/KEY: misc_feature
<223> OTHER INFORMATION: R1 and R2 form a birradical which is
      -(CH2)2-O-(CH2)2-NH-C(=O)-
<220> FEATURE:
<221> NAME/KEY: misc_feature
<222> LOCATION: (2)..(2)
<223> OTHER INFORMATION: D-Ala

<400> SEQUENCE: 54

```
Arg Ala Phe Gln Ala Phe Arg Lys Met Trp Pro Phe Phe Ala Met
1               5                   10                  15
```

<210> SEQ ID NO 55
<211> LENGTH: 19
<212> TYPE: DNA
<213> ORGANISM: Artificial Sequence
<220> FEATURE:
<223> OTHER INFORMATION: PRIMER

<400> SEQUENCE: 55
catatgccca accccaggc                                                    19

<210> SEQ ID NO 56
<211> LENGTH: 26
<212> TYPE: DNA
<213> ORGANISM: Artificial Sequence
<220> FEATURE:
<223> OTHER INFORMATION: PRIMER

<400> SEQUENCE: 56
gcggccgcgg ggccaggtgt agggtt                                            26

<210> SEQ ID NO 57
<211> LENGTH: 19
<212> TYPE: DNA
<213> ORGANISM: Artificial Sequence
<220> FEATURE:
<223> OTHER INFORMATION: PRIMER

<400> SEQUENCE: 57
atgcgtatcc ccgtagatg                                                    19

<210> SEQ ID NO 58
<211> LENGTH: 21
<212> TYPE: DNA
<213> ORGANISM: Artificial Sequence
<220> FEATURE:
<223> OTHER INFORMATION: PRIMER

<400> SEQUENCE: 58
gtagggcctc cacacggcct c                                                 21